(12) United States Patent
Reed et al.

(10) Patent No.: US 6,312,695 B1
(45) Date of Patent: Nov. 6, 2001

(54) COMPOUNDS AND METHODS FOR THERAPY OF LUNG CANCER

(75) Inventors: Steven G. Reed, Bellevue; Tong Tong Wang, Medina, both of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/123,912

(22) Filed: Jul. 27, 1998

Related U.S. Application Data

(63) Continuation-in-part of application No. 09/040,802, filed on Mar. 18, 1998.
(51) Int. Cl.[7] .................. A61K 39/00; C07K 14/435
(52) U.S. Cl. .................. 424/185.1; 530/350; 424/192.1; 424/277.1
(58) Field of Search .................. 536/23.1, 23.4, 536/23.5; 530/350; 424/184.1, 185.1, 192.1, 277.1

(56) References Cited

U.S. PATENT DOCUMENTS 5,783,422 * 7/1998 Suminami et al. .

FOREIGN PATENT DOCUMENTS

| | | |
|---|---|---|
| 0695760A1 | 2/1996 | (EP) . |
| WO 91/18926 | 12/1991 | (WO) . |
| WO 94/06929 | 3/1994 | (WO) . |
| WO 95/21862 | 8/1995 | (WO) . |
| WO 96/02552 | 2/1996 | (WO) . |
| WO 96/28473 | 9/1996 | (WO) . |
| WO 96/30389 | 10/1996 | (WO) . |
| WO 97/07244 | 2/1997 | (WO) . |
| WO 98/35985 | 8/1998 | (WO) . |
| WO 98/46788 | 10/1998 | (WO) . |
| WO 99/38973 | 8/1999 | (WO) . |
| WO 99/47674 | 9/1999 | (WO) . |

OTHER PUBLICATIONS

Wells et al., *J. Leukocyte Biology*, 61:545–550, 1997.*
Russell et al., *J. Mol. Biol.*, 244:332–350, 1994.*
Gerhold et al., *Bioessays*, 18(12):973–981, 1996.*
Database EMBLest17 Accession No. W22264:Human retina cDNA Tsp509I–cleaved Homo sapiens cDNA not directional, May 9, 1996.
Database EMBLest17 Accession No. AA340797: EST46165 Fetal Kidney II Homo Sapiens cDNA 3' end, Apr. 18, 1997.
Brass et al., "Translation initiation factor eIF–4gamma is encoded by an amplified gene and induces an immune response in squamous cell lung carcinoma," *Human Molecular Genetics* 6(1):33–39, 1997.

Finch et al., "Identification of a cloned sequence activated during multi–stage carcinogenesis in mouse skin," *Carcinogenesis* 12(8):1519–1522, 1991.
Baldi et al., "Differential expression of Rb2/p130 and p107 in normal human tissues and in primary lung cancer," *Clinical Cancer Research* 3(10):1691–1697, Oct. 1997.
Database EMBL Nucleotide and Protein Sequence, Accession No. AI468638, Mar. 17, 1999.
Hara et al., "Characterization of cell phenotype by a novel cDNA library subtraction system: expression of CD8α in a mast cell–derived interleukin–4–dependent cell line," *Blood* 84(1):189–199, Jul. 1, 1994.
Henderson et al., "Identification of lung tumor antigens for cancer immunotherapy: immunological and molecular approaches," *Immunological Investigation* 29(2):87–91, May 2000.
Hogan et al., "The peptide recognized by HLA–A68.2–restricted, squamous cell carcinoma of the lung–specific cytotoxic T lymphocytes is derived from a mutated elongation factor 2 gene," *Cancer Research* 58(22):5144–5150, Nov. 15, 1998.
Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.
Marshall and Hodgson, "DNA chips: an array of possibilities," *Nature Biotechnology* 16:27–31, Jan. 1998.
Ramsay, G., "DNA chips: state–of–the art," *Nature Biotechnology* 16:40–44, Jan. 1998.
Visseren et al., "Identification of HLA–A *0201–restricted CTL epitopes encoded by the tumor–specific MAGE–2 gene product," *International Journal of Cancer* 73(1):125–130, 1997.
Wang et al., "Identification of genes differentially over–expressed in lung squamous cell carcinoma using combination of cDNA subtraction and microarray analysis," *Oncogene* 19(12):1519–1528, Mar. 16, 2000.

* cited by examiner

Primary Examiner—Marianne P. Allen
(74) Attorney, Agent, or Firm—Seed Intellectual Property Law Group PLLC

(57) ABSTRACT

Compounds and methods for treating lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

9 Claims, No Drawings

SEQUENCE LISTING

```
<160> NUMBER OF SEQ ID NOS: 114

<210> SEQ ID NO 1
<211> LENGTH: 315
<212> TYPE: DNA
<213> ORGANISM: Homo sapiens
<220> FEATURE:
<221> NAME/KEY: modified_base
<222> LOCATION: (236)
<223> OTHER INFORMATION: Where n is a, c, g or t
<221> NAME/KEY: modified_base
<222> LOCATION: (241)
<223> OTHER INFORMATION: Where n is a, c, g or t

<400> SEQUENCE: 1
gcagagacag actggtggtt gaacctggag gtgccaaaaa agccagctgc gggcccagga      60
cagctgccgt gagactcccg atgtcacagg cagtctgtgt ggttacagcg cccctcagtg     120
ttcatctcca gcagagacaa cggaggaggc tcccaccagg acggttctca ttatttatat     180
gttaatatgt ttgtaaactc atgtacagtt tttttggggg gggaagcaat gggaanggta     240
naaattacaa atagaatcat ttgctgtaat ccttaaatgg caaacggtca ggccacgtga     300
aaaaaaaaaa aaaaa                                                      315

<210> SEQ ID NO 2
<211> LENGTH: 380
<212> TYPE: DNA
<213> ORGANISM: Homo sapiens

<400> SEQUENCE: 2
atttaggctt aagattttgt ttaccttgt tactaaggag caaattagta ttaaagtata       60
atatatataa acaaatacaa aaagtttga gtggttcagc tttttttattt tttttaatgg     120 cataactttt aacaacactg ctctgtaatg ggttgaactg tggtactcag actgagataa     180
ctgaaatgag tggatgtata gtgttattgc ataattatcc cactatgaag caaagggact    240 ggataaaattc ccagtctaga ttattagcct ttgttaacca tcaagcacct agaagaagaa    300
ttattggaaa ttttgtcctc tgtaactggc actttggggt gtgacttatc ttttgccttt    360
gtaaaaaaaa aaaaaaaaa                                                  380

<210> SEQ ID NO 3
<211> LENGTH: 346
<212> TYPE: DNA
```

```
<213> ORGANISM: Homo sapiens
<220> FEATURE:
<221> NAME/KEY: modified_base
<222> LOCATION: (316)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (318)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (323)
<223> OTHER INFORMATION: Where n is a, c, g or t
<221> NAME/KEY: modified_base
<222> LOCATION: (326)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (330)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (336)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (339)
<223> OTHER INFORMATION: Where n is a, c, g or t
<221> NAME/KEY: modified_base
<222> LOCATION: (340)
<223> OTHER INFORMATION: Where n is a, c, g or t
<221> NAME/KEY: modified_base
<222> LOCATION: (342)
<223> OTHER INFORMATION: Where n is a, c, g or t
<221> NAME/KEY: modified_base
<222> LOCATION: (343)
<223> OTHER INFORMATION: Where n is a, c, g or t

<400> SEQUENCE: 3
ttgtaagtat acaattttag aaaggattaa atgttattga tcattttact gaatactgca      60
catcctcacc atacaccatc cactttccaa taacatttaa tcctttctaa aattgtaagt     120
atacaattgt actttctttg gatttcata acaaatatac catagactgt taattttatt     180
gaagtttcct taatggaatg agtcattttt gtcttgtgct tttgaggtta cctttgcttt     240
gacttccaac aatttgatca tatagtgttg agctgtggaa atctttaagt ttattctata     300
gcaataattt ctattnnnag annccnggnn naaaannann annaaa                    346

<210> SEQ ID NO 4
<211> LENGTH: 372
<212> TYPE: DNA
<213> ORGANISM: Homo sapiens
<220> FEATURE:
<221> NAME/KEY: modified_base
<222> LOCATION: (296)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (332)
<223> OTHER INFORMATION: Where n is a, c, g or t

<400> SEQUENCE: 4
```

```
actagtctca ttactccaga attatgctct tgtacctgtg tggctgggtt tcttagtcgt      60
tggtttggtt tggttttttg aactggtatg tagggtggtt cacagttcta atgtaagcac     120
tctcttctcc aagttgtgct ttgtgdggac aatcattctt tgaacattag agaggaaggc     180
agttcaagct gttgaaaaga ctattgctta tttttgtttt taaagaccta cttgacgtca     240
tgtggacagt gcacgtgcct tacgctacat cttgttttct aggaagaagg ggatgcnggg     300
aaggantggg tgctttgtga tggataaaac gnctaaataa cacacccttta cattttgaaa     360 aaaacaaaac aa                                                         372
```

<210> SEQ ID NO 5
<211> LENGTH: 698
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (345)
<223> OTHER INFORMATION: Where n is a, c, g or t
<221> NAME/KEY: modified_base
<222> LOCATION: (422)
<223> OTHER INFORMATION: Where n is a, c, g or t
<221> NAME/KEY: modified_base
<222> LOCATION: (430)
<223> OTHER INFORMATION: Where n is a, c, g or t
<221> NAME/KEY: modified_base
<222> LOCATION: (433)
<223> OTHER INFORMATION: Where n is a, c, g or t
<221> NAME/KEY: modified_base
<222> LOCATION: (436)
<223> OTHER INFORMATION: Where n is a, c, g or t
<221> NAME/KEY: modified_base
<222> LOCATION: (438)
<223> OTHER INFORMATION: Where n is a, c, g or t
<221> NAME/KEY: modified_base
<222> LOCATION: (472)
<223> OTHER INFORMATION: Where n is a, c, g or t
<221> NAME/KEY: modified_base
<222> LOCATION: (481)
<223> OTHER INFORMATION: Where n is a, c, g or t
<221> NAME/KEY: modified_base
<222> LOCATION: (486)
<223> OTHER INFORMATION: Where n is a, c, g or t
<221> NAME/KEY: modified_base
<222> LOCATION: (515)
<223> OTHER INFORMATION: Where n is a, c, g or t
<221> NAME/KEY: modified_base
<222> LOCATION: (521)
<223> OTHER INFORMATION: Where n is a, c, g or t
<221> NAME/KEY: modified_base
<222> LOCATION: (526)
<223> OTHER INFORMATION: Where n is a, c, g or t
<221> NAME/KEY: modified_base
<222> LOCATION: (549)
<223> OTHER INFORMATION: Where n is a, c, g or t
<221> NAME/KEY: modified_base
<222> LOCATION: (553)
<223> OTHER INFORMATION: Where n is a, c, g or t
<221> NAME/KEY: modified_base
<222> LOCATION: (556)
<223> OTHER INFORMATION: Where n is a, c, g or t
<221> NAME/KEY: modified_base
<222> LOCATION: (557)
<223> OTHER INFORMATION: Where n is a, c, g or t
<221> NAME/KEY: modified_base
<222> LOCATION: (559)
<223> OTHER INFORMATION: Where n is a, c, g or t
<221> NAME/KEY: modified_base
<222> LOCATION: (568)
<223> OTHER INFORMATION: Where n is a, c, g or t
<221> NAME/KEY: modified_base
<222> LOCATION: (593)
<223> OTHER INFORMATION: Where n is a, c, g or t
<221> NAME/KEY: modified_base
<222> LOCATION: (597)
<223> OTHER INFORMATION: Where n is a, c, g or t
<221> NAME/KEY: modified_base
<222> LOCATION: (605)
<223> OTHER INFORMATION: Where n is a, c, g or t
<221> NAME/KEY: modified_base
<222> LOCATION: (611)
<223> OTHER INFORMATION: Where n is a, c, g or t
<221> NAME/KEY: modified_base
<222> LOCATION: (613)
<223> OTHER INFORMATION: Where n is a, c, g or t
<221> NAME/KEY: modified_base
<222> LOCATION: (616)
<223> OTHER INFORMATION: Where n is a, c, g or t
<221> NAME/KEY: modified_base
<222> LOCATION: (618)
<223> OTHER INFORMATION: Where n is a, c, g or t
<221> NAME/KEY: modified_base
<222> LOCATION: (620)
<223> OTHER INFORMATION: Where n is a, c, g or t
<221> NAME/KEY: modified_base
<222> LOCATION: (628)
<223> OTHER INFORMATION: Where n is a, c, g or t
<221> NAME/KEY: modified_base
<222> LOCATION: (630)
<223> OTHER INFORMATION: Where n is a, c, g or t
<221> NAME/KEY: modified_base
<222> LOCATION: (632)
<223> OTHER INFORMATION: Where n is a, c, g or t
<221> NAME/KEY: modified_base
<222> LOCATION: (634)
<223> OTHER INFORMATION: Where n is a, c, g or t
<221> NAME/KEY: modified_base
<222> LOCATION: (635)
<223> OTHER INFORMATION: Where n is a, c, g or t
<221> NAME/KEY: modified_base
<222> LOCATION: (639)
<223> OTHER INFORMATION: Where n is a, c, g or t
<221> NAME/KEY: modified_base
<222> LOCATION: (643)
<223> OTHER INFORMATION: Where n is a, c, g or t
<221> NAME/KEY: modified_base
<222> LOCATION: (647)
<223> OTHER INFORMATION: Where n is a, c, g or t
<221> NAME/KEY: modified_base
<222> LOCATION: (648)
<223> OTHER INFORMATION: Where n is a, c, g or t
<221> NAME/KEY: modified_base
<222> LOCATION: (649)
<223> OTHER INFORMATION: Where n is a, c, g or t
<221> NAME/KEY: modified_base
<222> LOCATION: (652)
<223> OTHER INFORMATION: Where n is a, c, g or t
<221> NAME/KEY: modified_base
<222> LOCATION: (654)
<223> OTHER INFORMATION: Where n is a, c, g or t
<221> NAME/KEY: modified_base
<222> LOCATION: (658)
<223> OTHER INFORMATION: Where n is a, c, g or t
<221> NAME/KEY: modified_base
<222> LOCATION: (664)
<223> OTHER INFORMATION: Where n is a, c, g or t
<221> NAME/KEY: modified_base
<222> LOCATION: (690)
<223> OTHER INFORMATION: Where n is a, c, g or t

<400> SEQUENCE: 5

| | | | | | |
|---|---|---|---|---|---|
| actagtanga | tagaaacact | gtgtcccgag | agtaaggaga | gaagctacta | ttgattagag | 60 |
| cctaacccag | gttaactgca | agaagaggcg | ggatactttc | agctttccat | gtaactgtat | 120 |
| gcataaagcc | aatgtagtcc | agtttctaag | atcatgttcc | aagctaactg | aatcccactt | 180 |
| caatacacac | tcatgaactc | ctgatggaac | aataacaggc | ccaagcctgt | ggtatgatgt | 240 |

```
gcacacttgc tagactcaga aaaaatacta ctctcataaa tgggtgggag tattttgggt    300
gacaacctac tttgcttggc tgagtgaagg aatgatattc atatnttcat ttattccatg    360
gacatttagt tagtgctttt tatataccag gcatgatgct gagtgacact cttgtgtata    420
tntccaaatn ttngtncngt cgctgcacat atctgaaatc ctatattaag antttcccaa    480
natgangtcc ctggtttttc cacgccactt gatcngtcaa ngatctcacc tctgtntgtc    540
ctaaaaccnt ctnctnnang gttagacngg acctctcttc tcccttcccg aanaatnaag    600
tgtgngaaga nanccncncn ccccctncn tncnncctng ccngctnnnc cncntgtngg    660
gggngccgcc ccgcggggg gacccccccn ttttcccc                             698
```

<210> SEQ ID NO 6
<211> LENGTH: 740
<212> TYPE: DNA
<213> ORGANISM: Homo sapiens
<220> FEATURE:
<221> NAME/KEY: modified_base
<222> LOCATION: (82)
<223> OTHER INFORMATION: Where n is a, c, g or t
<221> NAME/KEY: modified_base
<222> LOCATION: (406)
<223> OTHER INFORMATION: Where n is a, c, g or t
<221> NAME/KEY: modified_base
<222> LOCATION: (426)
<223> OTHER INFORMATION: Where n is a, c, g or t
<221> NAME/KEY: modified_base
<222> LOCATION: (434)
<223> OTHER INFORMATION: Where n is a, c, g or t
<221> NAME/KEY: modified_base
<222> LOCATION: (462)
<223> OTHER INFORMATION: Where n is a, c, g or t
<221> NAME/KEY: modified_base
<222> LOCATION: (536)
<223> OTHER INFORMATION: Where n is a, c, g or t
<221> NAME/KEY: modified_base
<222> LOCATION: (551)
<223> OTHER INFORMATION: Where n is a, c, g or t
<221> NAME/KEY: modified_base
<222> LOCATION: (558)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (582)
<223> OTHER INFORMATION: Where n is a, c, g or t
<221> NAME/KEY: modified_base
<222> LOCATION: (584)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (638)
<223> OTHER INFORMATION: Where n is a, c, g or t
<221> NAME/KEY: modified_base
<222> LOCATION: (651)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (664)
<223> OTHER INFORMATION: Where n is a, c, g or t
<221> NAME/KEY: modified_base
<222> LOCATION: (673)
<223> OTHER INFORMATION: Where n is a, c, g or t
<221> NAME/KEY: modified_base
<222> LOCATION: (675)
<223> OTHER INFORMATION: Where n is a, c, g or t

```
<221> NAME/KEY: modified_base
<222> LOCATION: (697)
<223> OTHER INFORMATION: Where n is a, c, g or t
<221> NAME/KEY: modified_base
<222> LOCATION: (706)
<223> OTHER INFORMATION: Where n is a, c, g or t
<221> NAME/KEY: modified_base
<222> LOCATION: (711)
<223> OTHER INFORMATION: Where n is a, c, g or t
<221> NAME/KEY: modified_base
<222> LOCATION: (715)
<223> OTHER INFORMATION: Where n is a, c, g or t
<221> NAME/KEY: modified_base
<222> LOCATION: (716)
<223> OTHER INFORMATION: Where n is a, c, g or t
<221> NAME/KEY: modified_base
<222> LOCATION: (717)
<223> OTHER INFORMATION: Where n is a, c, g or t
<221> NAME/KEY: modified_base
<222> LOCATION: (723)
<223> OTHER INFORMATION: Where n is a, c, g or t
<221> NAME/KEY: modified_base
<222> LOCATION: (724)
<223> OTHER INFORMATION: Where n is a, c, g or t
<221> NAME/KEY: modified_base
<222> LOCATION: (725)
<223> OTHER INFORMATION: Where n is a, c, g or t
<221> NAME/KEY: modified_base
<222> LOCATION: (733)
<223> OTHER INFORMATION: Where n is a, c, g or t

<400> SEQUENCE: 6
actagtcaaa aatgctaaaa taatttggga gaaaatattt tttaagtagt gttatagttt    60
catgtttatc ttttattatg tnttgtgaag ttgtgtcttt tcactaatta cctatactat   120
gccaatattt ccttatatct atccataaca tttatactac atttgtaaga gaatatgcac   180
gtgaaactta acactttata aggtaaaaat gaggtttcca agatttaata atctgatcaa   240
gttcttgtta tttccaaata gaatggactt ggtctgttaa ggggctaagg gagaagaaga   300
agataaggtt aaaagttgtt aatgaccaaa cattctaaaa gaaatgcaaa aaaaaattta   360
ttttcaagcc ttcgaactat ttaaggaaag caaaatcatt tcctanatgc atatcatttg   420 tgaganttc tcantaatat cctgaatcat tcatttcagc tnaggcttca tgttgactcg   480
atatgtcatc tagggaaagt ctatttcatg gtccaaacct gttgccatag ttggtnaggc   540
tttcctttaa ntgtgaanta ttnacangaa attttctctt tnanagttct tnatagggtt   600 agggqtgtgg gaaaagcttc taacaatctg tagtgttncg tgttatctgt ncagaaccan   660
aatnacggat cgnangaagg actgggtcta tttacangaa cgaatnatct ngttnnntgt   720
gtnnncaact ccngggagcc                                                740

<210> SEQ ID NO 7
<211> LENGTH: 670
<212> TYPE: DNA
<213> ORGANISM: Homo sapiens
<220> FEATURE:
<221> NAME/KEY: modified_base
<222> LOCATION: (265)
<223> OTHER INFORMATION: Where n is a, c, g or t
<221> NAME/KEY: modified_base
<222> LOCATION: (268)
<223> OTHER INFORMATION: Where n is a, c, g or t
<221> NAME/KEY: modified_base
<222> LOCATION: (457)
<223> OTHER INFORMATION: Where n is a, c, g or t
<221> NAME/KEY: modified_base
<222> LOCATION: (470)
<223> OTHER INFORMATION: Where n is a, c, g or t
<221> NAME/KEY: modified_base
<222> LOCATION: (485)
```

<223> OTHER INFORMATION: Where n is a, c, g or t
<221> NAME/KEY: modified_base
<222> LOCATION: (546)
<223> OTHER INFORMATION: Where n is a, c, g or t
<221> NAME/KEY: modified_base
<222> LOCATION: (553)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (590)
<223> OTHER INFORMATION: Where n is a, c, g or t
<221> NAME/KEY: modified_base
<222> LOCATION: (596)
<223> OTHER INFORMATION: Where n is a, c, g or t
<221> NAME/KEY: modified_base
<222> LOCATION: (613)
<223> OTHER INFORMATION: Where n is a, c, g or t
<221> NAME/KEY: modified_base
<222> LOCATION: (624)
<223> OTHER INFORMATION: Where n is a, c, g or t
<221> NAME/KEY: modified_base
<222> LOCATION: (639)
<223> OTHER INFORMATION: Where n is a, c, g or t
<221> NAME/KEY: modified_base
<222> LOCATION: (653)
<223> OTHER INFORMATION: Where n is a, c, g or t
<221> NAME/KEY: modified_base
<222> LOCATION: (659)
<223> OTHER INFORMATION: Where n is a, c, g or t
<221> NAME/KEY: modified_base
<222> LOCATION: (661)
<223> OTHER INFORMATION: Where n is a, c, g or t

<400> SEQUENCE: 7

```
gctggggagc tcggcatggc ggtccccgct gcagccatgg ggccctcggc gttgggccag      60
agcggccccg gctcgatggc cccgtggtgc tcagtgagca gcggcccgtc gcgctacgtg     120
cttgggatgc aggagctgtt ccggggccac agcaagaccg cgagttcctg gcgcacagcg     180
ccaaggtgca ctcggtggcc tggagttgcg acgggcgtcg cctacctcgg ggtcttcgac     240
aagacgccac gtcttcttgc tgganaanga ccgttggtca agaaaacaa ttatcgggga     300
catggggata gtgtggacca ctttgttggc atccaagtaa tcctgaccta tttgttacgg     360
cgtctggaga taaaaccatt cgcatctggg atgtgaggac tacaaaatgc attgccactg     420
tgaacactaa aggggagaac attaatatct gctggantcc tgatgggcan accattgctg     480
tagcnacaag gatgatgtgg tgactttatt gatgccaaga aaccccgttc caaagcaaaa     540
aaacanttcc aanttcgaag tcaccnaaat ctcctggaac aatgaacatn aatatnttct     600
tcctgacaat ggnccttggg tgtntcacat cctcagctnc cccaaaactg aancctgtnc     660
natccacccc                                                           670
```

<210> SEQ ID NO 8
<211> LENGTH: 689
<212> TYPE: DNA
<213> ORGANISM: Homo sapiens
<220> FEATURE:
<221> NAME/KEY: modified_base
<222> LOCATION: (253)
<223> OTHER INFORMATION: Where n is a, c, g or t
<221> NAME/KEY: modified_base
<222> LOCATION: (335)
<223> OTHER INFORMATION: Where n is a, c, g or t
<221> NAME/KEY: modified_base
<222> LOCATION: (410)
<223> OTHER INFORMATION: Where n is a, c, g or t
<221> NAME/KEY: modified_base
<222> LOCATION: (428)
<223> OTHER INFORMATION: Where n is a, c, g or t -continued

```
<221> NAME/KEY: modified_base
<222> LOCATION: (448)
<223> OTHER INFORMATION: Where n is a, c, g or t
<221> NAME/KEY: modified_base
<222> LOCATION: (458)
<223> OTHER INFORMATION: Where n is a, c, g or t
<221> NAME/KEY: modified_base
<222> LOCATION: (466)
<223> OTHER INFORMATION: Where n is a, c, g or t
<221> NAME/KEY: modified_base
<222> LOCATION: (479)
<223> OTHER INFORMATION: Where n is a, c, g or t
<221> NAME/KEY: modified_base
<222> LOCATION: (480)
<223> OTHER INFORMATION: Where n is a, c, g or t
<221> NAME/KEY: modified_base
<222> LOCATION: (482)
<223> OTHER INFORMATION: Where n is a, c, g or t
<221> NAME/KEY: modified_base
<222> LOCATION: (483)
<223> OTHER INFORMATION: Where n is a, c, g or t
<221> NAME/KEY: modified_base
<222> LOCATION: (485)
<223> OTHER INFORMATION: Where n is a, c, g or t
<221> NAME/KEY: modified_base
<222> LOCATION: (488)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (492)
<223> OTHER INFORMATION: Where n is a, c, g or t
<221> NAME/KEY: modified_base
<222> LOCATION: (495)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (500)
<223> OTHER INFORMATION: Where n is a, c, g or t
<221> NAME/KEY: modified_base
<222> LOCATION: (502)
<223> OTHER INFORMATION: Where n is a, c, g or t
<221> NAME/KEY: modified_base
<222> LOCATION: (503)
<223> OTHER INFORMATION: Where n is a, c, g or t
<221> NAME/KEY: modified_base
<222> LOCATION: (512)
<223> OTHER INFORMATION: Where n is a, c, g or t
<221> NAME/KEY: modified_base
<222> LOCATION: (516)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (525)
<223> OTHER INFORMATION: Where n is a, c, g or t
<221> NAME/KEY: modified_base
<222> LOCATION: (526)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (530)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (546)
<223> OTHER INFORMATION: Where n is a, c, g or t
<221> NAME/KEY: modified_base
<222> LOCATION: (550)
<223> OTHER INFORMATION: Where n is a, c, g or t
<221> NAME/KEY: modified_base
```

<222> LOCATION: (581)
<223> OTHER INFORMATION: Where n is a, c, g or t
<221> NAME/KEY: modified_base
<222> LOCATION: (593)
<223> OTHER INFORMATION: Where n is a, c, g or t
<221> NAME/KEY: modified_base
<222> LOCATION: (594)
<223> OTHER INFORMATION: Where n is a, c, g or t
<221> NAME/KEY: modified_base
<222> LOCATION: (601)
<223> OTHER INFORMATION: Where n is a, c, g or t
<221> NAME/KEY: modified_base
<222> LOCATION: (606)
<223> OTHER INFORMATION: Where n is a, c, g or t
<221> NAME/KEY: modified_base
<222> LOCATION: (609)
<223> OTHER INFORMATION: Where n is a, c, g or t
<221> NAME/KEY: modified_base
<222> LOCATION: (610)
<223> OTHER INFORMATION: Where n is a, c, g or t
<221> NAME/KEY: modified_base
<222> LOCATION: (620)
<223> OTHER INFORMATION: Where n is a, c, g or t
<221> NAME/KEY: modified_base
<222> LOCATION: (621)
<223> OTHER INFORMATION: Where n is a, c, g or t
<221> NAME/KEY: modified_base
<222> LOCATION: (622)
<223> OTHER INFORMATION: Where n is a, c, g or t
<221> NAME/KEY: modified_base
<222> LOCATION: (628)
<223> OTHER INFORMATION: Where n is a, c, g or t
<221> NAME/KEY: modified_base
<222> LOCATION: (641)
<223> OTHER INFORMATION: Where n is a, c, g or t
<221> NAME/KEY: modified_base
<222> LOCATION: (646)
<223> OTHER INFORMATION: Where n is a, c, g or t
<221> NAME/KEY: modified_base
<222> LOCATION: (656)
<223> OTHER INFORMATION: Where n is a, c, g or t
<221> NAME/KEY: modified_base
<222> LOCATION: (673)
<223> OTHER INFORMATION: Where n is a, c, g or t

<400> SEQUENCE: 8

```
actagtatct aggaatgaac agtaaaagag gagcagttgg ctacttgatt acaacagagt      60
aaatgaagta ctggatttgg gaaaacctgg ttttattaga acatatggaa tgaaagccta    120
cacctagcat tgcctactta gccccctgaa ttaacagagc ccaattgaga caaaccctg     180
gcaacaggaa attcaaggga gaaaaagtaa gcaacttggg ctaggatgag ctgactccct   240
tagagcaaag ganagacagc ccccattacc aaataccatt tttgcctggg gcttgtgcag   300
ctggcagtgt tcctgcccca gcatggcacc ttatngtttt gatagcaact tcgttgaatt   360
ttcaccaact tattacttga aattataata tagcctgtcc gtttgctgtn tccaggctgt   420
gatatatntt cctagtggtt tgactttnaa aataaatnag gtttantttt ctcccccnn    480
cnntnctncc nntcnctcnn cnntcccccc cnctcngtcc tccnnnnttn ggggggggccn   540
ccccncggn ggaccccccct ttggtccctt agtggaggtt natggcccct ggnnttatcc   600
nggccntann tttccccgtn nnaaatgntt ccccctccca ntcccnccac ctcaanccgg   660
aagcctaagt ttntaccctg ggggtcccc                                     689
```

<210> SEQ ID NO 9
<211> LENGTH: 674
<212> TYPE: DNA
<213> ORGANISM: Homo sapiens
<220> FEATURE:
<221> NAME/KEY: modified_base
<222> LOCATION: (602)

<223> OTHER INFORMATION: Where n is a, c, g or t
<221> NAME/KEY: modified_base
<222> LOCATION: (632)
<223> OTHER INFORMATION: Where n is a, c, g or t
<221> NAME/KEY: modified_base
<222> LOCATION: (639)
<223> OTHER INFORMATION: Where n is a, c, g or t
<221> NAME/KEY: modified_base
<222> LOCATION: (668)
<223> OTHER INFORMATION: Where n is a, c, g or t

<400> SEQUENCE: 9

| | | | | | |
|---|---|---|---|---|---|
| gtccactctc | ctttgagtgt | actgtcttac | tgtgcactct | gttttttcaac | tttctagata | 60 |
| taaaaaatgc | ttgttctata | gtggagtaag | agctcacaca | cccaaggcag | caagataact | 120 |
| gaaaaaagcg | aggctttttt | gccaccttgg | taaaggccag | ttcactgcta | tagaactgct | 180 |
| ataagcctga | agggaagtag | ctatgagact | ttccattttt | cttagttctc | ccaataggct | 240 |
| ccttcatgga | aaaaggcttc | ctgtaataat | tttcacctaa | tgaattagca | gtgtgattat | 300 |
| ttctgaaata | agagacaaat | tgggccgcag | agtcttcctg | tgatttaaaa | taaacaaccc | 360 |
| aaagttttgt | ttggtcttca | ccaaaggaca | tactctaggg | ggtatgttgt | tgaagacatt | 420 |
| caaaaacatt | agctgttctg | tctttcaatt | tcaagttatt | ttggagactg | cctccatgtg | 480 |
| agttaattac | tttgctctgg | aactagcatt | attgtcatta | tcatcacatt | ctgtcatcat | 540 |
| catctgaata | atattgtgga | tttccccctc | tgcttgcatc | ttcttttgac | tcctctggga | 600 |
| anaaatgtca | aaaaaaaagg | tcgatctact | cngcaaggnc | catctaatca | ctgcgctgga | 660 |
| aggacccnct | gccc | | | | | 674 |

<210> SEQ ID NO 10
<211> LENGTH: 346
<212> TYPE: DNA
<213> ORGANISM: Homo sapiens
<220> FEATURE:
<221> NAME/KEY: modified_base
<222> LOCATION: (320)
<223> OTHER INFORMATION: Where n is a, c, g or t
<221> NAME/KEY: modified_base
<222> LOCATION: (321)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (325)
<223> OTHER INFORMATION: Where n is a, c, g or t
<221> NAME/KEY: modified_base
<222> LOCATION: (326)
<223> OTHER INFORMATION: Where n is a, c, g or t
<221> NAME/KEY: modified_base
<222> LOCATION: (328)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (330)
<223> OTHER INFORMATION: Where n is a, c, g or t
<221> NAME/KEY: modified_base
<222> LOCATION: (332)
<223> OTHER INFORMATION: Where n is a, c, g or t
<221> NAME/KEY: modified_base
<222> LOCATION: (333)
<223> OTHER INFORMATION: Where n is a, c, g or t
<221> NAME/KEY: modified_base
<222> LOCATION: (334)
<223> OTHER INFORMATION: Where n is a, c, g or t
<221> NAME/KEY: modified_base
<222> LOCATION: (335)
<223> OTHER INFORMATION: Where n is a, c, g or t
<221> NAME/KEY: modified_base
<222> LOCATION: (342)
<223> OTHER INFORMATION: Where n is a, c, g or t

<400> SEQUENCE: 10

| | | | | | |
|---|---|---|---|---|---|
| actagtctgc | tgatagaaag | cactatacat | cctattgttt | ctttctttcc | aaaatcagcc | 60 |
| ttctgtctgt | aacaaaaatg | tactttatag | agatggagga | aaaggtctaa | tactacatag | 120 |
| ccttaagtgt | ttctgtcatt | gttcaagtgt | attttctgta | acagaaacat | atttggaatg | 180 |
| tttttctttt | ccccttataa | attgtaattc | ctgaaatact | gctgctttaa | aaagtcccac | 240 |
| tgtcagatta | tattatctaa | caattgaata | ttgtaaatat | acttgtctta | cctctcaata | 300 |
| aaagggtact | tttctattan | nnagnngnnn | gnnnnataaa | anaaaa | | 346 |

<210> SEQ ID NO 11
<211> LENGTH: 602
<212> TYPE: DNA
<213> ORGANISM: Homo sapiens

<400> SEQUENCE: 11

| | | | | | |
|---|---|---|---|---|---|
| actagtaaaa | agcagcattg | ccaaataatc | cctaatttc | cactaaaaat | ataatgaaat | 60 |
| gatgttaagc | tttttgaaaa | gtttaggtta | aacctactgt | tgttagatta | atgtatttgt | 120 |
| tgcttccctt | tatctggaat | gtggcattag | ctttttatt | taaccctct | ttaattctta | 180 |
| ttcaattcca | tgacttaagg | ttggagagct | aaacactggg | attttggat | aacagactga | 240 |
| cagttttgca | taattataat | cggcattgta | catagaaagg | atatggctac | cttttgttaa | 300 |
| atctgcactt | tctaaatatc | aaaaaggga | aatgaagtta | taaatcaatt | tttgtataat | 360 |
| ctgtttgaaa | catgagtttt | atttgcttaa | tattagggct | ttgcccctt | tctgtaagtc | 420 |
| tcttgggatc | ctgtgtagaa | ctgttctcat | taaacaccaa | acagttaagt | ccattctctg | 480 |
| gtactagcta | caaattcggt | ttcatattct | acttaacaat | ttaaataaac | tgaaatattt | 540 |
| ctagatggtc | tacttctgtt | catataaaaa | caaaacttga | tttccaaaaa | aaaaaaaaa | 600 |
| aa | | | | | | 602 |

<210> SEQ ID NO 12
<211> LENGTH: 685
<212> TYPE: DNA
<213> ORGANISM: Homo sapiens
<220> FEATURE:
<221> NAME/KEY: modified_base
<222> LOCATION: (170)
<223> OTHER INFORMATION: Where n is a, c, g or t
<221> NAME/KEY: modified_base
<222> LOCATION: (279)
<223> OTHER INFORMATION: Where n is a, c, g or t
<221> NAME/KEY: modified_base
<222> LOCATION: (318)
<223> OTHER INFORMATION: Where n is a, c, g or t
<221> NAME/KEY: modified_base
<222> LOCATION: (321)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (422)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (453)
<223> OTHER INFORMATION: Where n is a, c, g or t
<221> NAME/KEY: modified_base -continued

```
<222> LOCATION: (459)
<223> OTHER INFORMATION: Where n is a, c, g or t
<221> NAME/KEY: modified_base
<222> LOCATION: (467)
<223> OTHER INFORMATION: Where n is a, c, g or t
<221> NAME/KEY: modified_base
<222> LOCATION: (468)
<223> OTHER INFORMATION: Where n is a, c, g or t
<221> NAME/KEY: modified_base
<222> LOCATION: (470)
<223> OTHER INFORMATION: Where n is a, c, g or t
<221> NAME/KEY: modified_base
<222> LOCATION: (473)
<223> OTHER INFORMATION: Where n is a, c, g or t
<221> NAME/KEY: modified_base
<222> LOCATION: (475)
<223> OTHER INFORMATION: Where n is a, c, g or t
<221> NAME/KEY: modified_base
<222> LOCATION: (482)
<223> OTHER INFORMATION: Where n is a, c, g or t
<221> NAME/KEY: modified_base
<222> LOCATION: (485)
<223> OTHER INFORMATION: Where n is a, c, g or t
<221> NAME/KEY: modified_base
<222> LOCATION: (486)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (498)
<223> OTHER INFORMATION: Where n is a, c, g or t
<221> NAME/KEY: modified_base
<222> LOCATION: (503)
<223> OTHER INFORMATION: Where n is a, c, g or t
<221> NAME/KEY: modified_base
<222> LOCATION: (506)
<223> OTHER INFORMATION: Where n is a, c, g or t
<221> NAME/KEY: modified_base
<222> LOCATION: (509)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (526)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (528)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (544)
<223> OTHER INFORMATION: Where n is a, c, g or t
<221> NAME/KEY: modified_base
<222> LOCATION: (551)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (568)
<223> OTHER INFORMATION: Where n is a, c, g or t
<221> NAME/KEY: modified_base
<222> LOCATION: (569)
<223> OTHER INFORMATION: Where n is a, c, g or t
<221> NAME/KEY: modified_base
<222> LOCATION: (574)
<223> OTHER INFORMATION: Where n is a, c, g or t
<221> NAME/KEY: modified_base
<222> LOCATION: (576)
```

```
-continued

<223> OTHER INFORMATION: Where n is a, c, g or t
<221> NAME/KEY: modified_base
<222> LOCATION: (582)
<223> OTHER INFORMATION: Where n is a, c, g or t
<221> NAME/KEY: modified_base
<222> LOCATION: (587)
<223> OTHER INFORMATION: Where n is a, c, g or t
<221> NAME/KEY: modified_base
<222> LOCATION: (588)
<223> OTHER INFORMATION: Where n is a, c, g or t
<221> NAME/KEY: modified_base
<222> LOCATION: (589)
<223> OTHER INFORMATION: Where n is a, c, g or t
<221> NAME/KEY: modified_base
<222> LOCATION: (590)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (593)
<223> OTHER INFORMATION: Where n is a, c, g or t
<221> NAME/KEY: modified_base
<222> LOCATION: (598)
<223> OTHER INFORMATION: Where n is a, c, g or t
<221> NAME/KEY: modified_base
<222> LOCATION: (599)
<223> OTHER INFORMATION: Where n is a, c, g or t
<221> NAME/KEY: modified_base
<222> LOCATION: (603)
<223> OTHER INFORMATION: Where n is a, c, g or t
<221> NAME/KEY: modified_base
<222> LOCATION: (605)
<223> OTHER INFORMATION: Where n is a, c, g or t
<221> NAME/KEY: modified_base
<222> LOCATION: (608)
<223> OTHER INFORMATION: Where n is a, c, g or t
<221> NAME/KEY: modified_base
<222> LOCATION: (633)
<223> OTHER INFORMATION: Where n is a, c, g or t
<221> NAME/KEY: modified_base
<222> LOCATION: (634)
<223> OTHER INFORMATION: Where n is a, c, g or t
<221> NAME/KEY: modified_base
<222> LOCATION: (635)
<223> OTHER INFORMATION: Where n is a, c, g or t
<221> NAME/KEY: modified_base
<222> LOCATION: (644)
<223> OTHER INFORMATION: Where n is a, c, g or t
<221> NAME/KEY: modified_base
<222> LOCATION: (646)
<223> OTHER INFORMATION: Where n is a, c, g or t
<221> NAME/KEY: modified_base
<222> LOCATION: (648)
<223> OTHER INFORMATION: Where n is a, c, g or t
<221> NAME/KEY: modified_base
<222> LOCATION: (651)
<223> OTHER INFORMATION: Where n is a, c, g or t
<221> NAME/KEY: modified_base
<222> LOCATION: (655)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (662)
<223> OTHER INFORMATION: Where n is a, c, g or t
<221> NAME/KEY: modified_base
<222> LOCATION: (663)
<223> OTHER INFORMATION: Where n is a, c, g or t
<221> NAME/KEY: modified_base
<222> LOCATION: (672)
<223> OTHER INFORMATION: Where n is a, c, g or t
<221> NAME/KEY: modified_base
<222> LOCATION: (674)
<223> OTHER INFORMATION: Where n is a, c, g or t
<221> NAME/KEY: modified_base
<222> LOCATION: (675)
<223> OTHER INFORMATION: Where n is a, c, g or t
```

<221> NAME/KEY: modified_base
<222> LOCATION: (682)
<223> OTHER INFORMATION: Where n is a, c, g or t
<221> NAME/KEY: modified_base
<222> LOCATION: (683)
<223> OTHER INFORMATION: Where n is a, c, g or t

<400> SEQUENCE: 12

```
actagtcctg tgaaagtaca actgaaggca gaaagtgtta ggattttgca tctaatgttc      60
attatcatgg tattgatgga cctaagaaaa taaaaattag actaagcccc caaataagct     120
gcatgcattt gtaacatgat tagtagattt gaatatatag atgtagtatn tttgggtatct    180
aggtgtttta tcattatgta aaggaattaa agtaaaggac tttgtagttg tttttattaa    240
atatgcatat agtagagtgc aaaaatatag caaaaatana aactaaaggt agaaaagcat    300
tttagatatg ccttaatnta nnaactgtgc caggtggccc tcggaataga tgccaggcag    360
agaccagtgc ctgggtggtg cctccccttg tctgccccccc tgaagaactt ccctcacgtg    420
angtagtgcc ctcgtaggtg tcacgtggan tantggganc aggccgnncn gtnanaagaa    480
ancanngtga nagtttcncc gtngangcng aactgtccct gngccnnnac gctcccanaa    540
cntntccaat ngacaatcga gtttccnnnc tccngnaacc tngccgnnnn cnngcccnnc    600
cantntgnta accccgcgcc cggatcgctc tcnnntcgtt ctcncncnaa ngggntttcn    660
cnnccgccgt cncnnccccg cnncc                                          685
```

<210> SEQ ID NO 13
<211> LENGTH: 694
<212> TYPE: DNA
<213> ORGANISM: Homo sapiens
<220> FEATURE:
<221> NAME/KEY: modified_base
<222> LOCATION: (503)
<223> OTHER INFORMATION: Where n is a, c, g or t
<221> NAME/KEY: modified_base
<222> LOCATION: (546)
<223> OTHER INFORMATION: Where n is a, c, g or t
<221> NAME/KEY: modified_base
<222> LOCATION: (599)
<223> OTHER INFORMATION: Where n is a, c, g or t
<221> NAME/KEY: modified_base
<222> LOCATION: (611)
<223> OTHER INFORMATION: Where n is a, c, g or t
<221> NAME/KEY: modified_base
<222> LOCATION: (636)
<223> OTHER INFORMATION: Where n is a, c, g or t
<221> NAME/KEY: modified_base
<222> LOCATION: (641)
<223> OTHER INFORMATION: Where n is a, c, g or t
<221> NAME/KEY: modified_base
<222> LOCATION: (643)
<223> OTHER INFORMATION: Where n is a, c, g or t
<221> NAME/KEY: modified_base
<222> LOCATION: (645)
<223> OTHER INFORMATION: Where n is a, c, g or t
<221> NAME/KEY: modified_base
<222> LOCATION: (656)
<223> OTHER INFORMATION: Where n is a, c, g or t
<221> NAME/KEY: modified_base
<222> LOCATION: (658)
<223> OTHER INFORMATION: Where n is a, c, g or t
<221> NAME/KEY: modified_base
<222> LOCATION: (662)
<223> OTHER INFORMATION: Where n is a, c, g or t
<221> NAME/KEY: modified_base
<222> LOCATION: (676)
<223> OTHER INFORMATION: Where n is a, c, g or t
<221> NAME/KEY: modified_base
<222> LOCATION: (679)
<223> OTHER INFORMATION: Where n is a, c, g or t
<221> NAME/KEY: modified_base
<222> LOCATION: (687)
<223> OTHER INFORMATION: Where n is a, c, g or t

<400> SEQUENCE: 13

```
cactagtcac tcattagcgt tttcaatagg gctcttaagt ccagtagatt acgggtagtc    60
agttgacgaa gatctggttt acaagaacta attaaatgtt tcattgcatt tttgtaagaa   120
cagaataatt ttataaaatg tttgtagttt ataattgccg aaaataattt aaagacactt   180
tttctctgtg tgtgcaaatg tgtgtttgtg atccattttt ttttttttt taggacacct   240
gtttactagc tagctttaca atatgccaaa aaaggatttc tccctgaccc catccgtggt   300
tcaccctctt ttccccccat gcttttgcc ctagtttata acaaaggaat gatgatgatt   360
taaaaagtag ttctgtatct tcagtatctt ggtcttccag aaccctctgg ttgggaaggg   420
gatcattttt tactggtcat ttccctttgg agtgtactac tttaacagat ggaaagaact   480
cattggccat ggaaacagcc gangtgttgg gagccagcag tgcatggcac cgtccggcat   540
ctggcntgat tggtctggct gccgtcattg tcagcacagt gccatgggac atggggaana   600
ctgactgcac ngccaatggt tttcatgaag aatacngcat ncncngtgat cacgtnancc   660
angacgctat ggggncana gggccanttg cttc                               694
```

<210> SEQ ID NO 14
<211> LENGTH: 679
<212> TYPE: DNA
<213> ORGANISM: Homo sapiens
<220> FEATURE:
<221> NAME/KEY: modified_base
<222> LOCATION: (29)
<223> OTHER INFORMATION: Where n is a, c, g or t
<221> NAME/KEY: modified_base
<222> LOCATION: (68)
<223> OTHER INFORMATION: Where n is a, c, g or t
<221> NAME/KEY: modified_base
<222> LOCATION: (83)
<223> OTHER INFORMATION: Where n is a, c, g or t
<221> NAME/KEY: modified_base
<222> LOCATION: (87)
<223> OTHER INFORMATION: Where n is a, c, g or t
<221> NAME/KEY: modified_base
<222> LOCATION: (94)
<223> OTHER INFORMATION: Where n is a, c, g or t
<221> NAME/KEY: modified_base
<222> LOCATION: (104)
<223> OTHER INFORMATION: Where n is a, c, g or t
<221> NAME/KEY: modified_base
<222> LOCATION: (117)
<223> OTHER INFORMATION: Where n is a, c, g or t
<221> NAME/KEY: modified_base
<222> LOCATION: (142)
<223> OTHER INFORMATION: Where n is a, c, g or t
<221> NAME/KEY: modified_base
<222> LOCATION: (145)
<223> OTHER INFORMATION: Where n is a, c, g or t
<221> NAME/KEY: modified_base
<222> LOCATION: (151)
<223> OTHER INFORMATION: Where n is a, c, g or t
<221> NAME/KEY: modified_base
<222> LOCATION: (187)
<223> OTHER INFORMATION: Where n is a, c, g or t
<221> NAME/KEY: modified_base
<222> LOCATION: (201)
<223> OTHER INFORMATION: Where n is a, c, g or t
<221> NAME/KEY: modified_base
<222> LOCATION: (211)
<223> OTHER INFORMATION: Where n is a, c, g or t
<221> NAME/KEY: modified_base
<222> LOCATION: (226)
<223> OTHER INFORMATION: Where n is a, c, g or t
<221> NAME/KEY: modified_base
<222> LOCATION: (229)

-continued

```
<223> OTHER INFORMATION: Where n is a, c, g or t
<221> NAME/KEY: modified_base
<222> LOCATION: (239)
<223> OTHER INFORMATION: Where n is a, c, g or t
<221> NAME/KEY: modified_base
<222> LOCATION: (241)
<223> OTHER INFORMATION: Where n is a, c, g or t
<221> NAME/KEY: modified_base
<222> LOCATION: (245)
<223> OTHER INFORMATION: Where n is a, c, g or t
<221> NAME/KEY: modified_base
<222> LOCATION: (252)
<223> OTHER INFORMATION: Where n is a, c, g or t
<221> NAME/KEY: modified_base
<222> LOCATION: (255)
<223> OTHER INFORMATION: Where n is a, c, g or t
<221> NAME/KEY: modified_base
<222> LOCATION: (259)
<223> OTHER INFORMATION: Where n is a, c, g or t
<221> NAME/KEY: modified_base
<222> LOCATION: (303)
<223> OTHER INFORMATION: Where n is a, c, g or t
<221> NAME/KEY: modified_base
<222> LOCATION: (309)
<223> OTHER INFORMATION: Where n is a, c, g or t
<221> NAME/KEY: modified_base
<222> LOCATION: (359)
<223> OTHER INFORMATION: Where n is a, c, g or t
<221> NAME/KEY: modified_base
<222> LOCATION: (387)
<223> OTHER INFORMATION: Where n is a, c, g or t
<221> NAME/KEY: modified_base
<222> LOCATION: (400)
<223> OTHER INFORMATION: Where n is a, c, g or t
<221> NAME/KEY: modified_base
<222> LOCATION: (441)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (461)
<223> OTHER INFORMATION: Where n is a, c, g or t
<221> NAME/KEY: modified_base
<222> LOCATION: (492)
<223> OTHER INFORMATION: Where n is a, c, g or t
<221> NAME/KEY: modified_base
<222> LOCATION: (504)
<223> OTHER INFORMATION: Where n is a, c, g or t
<221> NAME/KEY: modified_base
<222> LOCATION: (505)
<223> OTHER INFORMATION: Where n is a, c, g or t
<221> NAME/KEY: modified_base
<222> LOCATION: (512)
<223> OTHER INFORMATION: Where n is a, c, g or t
<221> NAME/KEY: modified_base
<222> LOCATION: (525)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (533)
<223> OTHER INFORMATION: Where n is a, c, g or t
<221> NAME/KEY: modified_base
<222> LOCATION: (574)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (609)
<223> OTHER INFORMATION: Where n is a, c, g or t
<221> NAME/KEY: modified_base
<222> LOCATION: (610)
<223> OTHER INFORMATION: Where n is a, c, g or t
<221> NAME/KEY: modified_base
<222> LOCATION: (618)
<223> OTHER INFORMATION: Where n is a, c, g or t
```

<221> NAME/KEY: modified_base
<222> LOCATION: (620)
<223> OTHER INFORMATION: Where n is a, c, g or t
<221> NAME/KEY: modified_base
<222> LOCATION: (626)
<223> OTHER INFORMATION: Where n is a, c, g or t
<221> NAME/KEY: modified_base
<222> LOCATION: (627)
<223> OTHER INFORMATION: Where n is a, c, g or t
<221> NAME/KEY: modified_base
<222> LOCATION: (633)
<223> OTHER INFORMATION: Where n is a, c, g or t
<221> NAME/KEY: modified_base
<222> LOCATION: (639)
<223> OTHER INFORMATION: Where n is a, c, g or t
<221> NAME/KEY: modified_base
<222> LOCATION: (645)
<223> OTHER INFORMATION: Where n is a, c, g or t
<221> NAME/KEY: modified_base
<222> LOCATION: (654)
<223> OTHER INFORMATION: Where n is a, c, g or t

<400> SEQUENCE: 14

| | | | | | |
|---|---|---|---|---|---|
| cagccgcctg | catctgtatc | cagcgccang | tcccgccagt | cccagctgcg | cgcgccccc    60 |
| agtcccgnac | ccgttcggcc | cangctnagt | tagncctcac | catnccggtc | aaaggangca  120 |
| ccaagtgcat | caaatacctg | cngtncggat | ntaaattcat | cttctggctt | gccgggattg  180 |
| ctgtccntgc | cattggacta | nggctccgat | ncgactctca | gaccanganc | atcttcganc  240 |
| naganactaa | tnatnattnt | tccagcttct | acacaggagt | ctatattctg | atcggatccg  300 |
| gcncctcnt | gatgctggtg | ggcttcctga | gctgctgcgg | ggctgtgcaa | gagtcccant  360 |
| gcatgctggg | actgttcttc | ggcttcntct | tggtgatatn | cgccattgaa | atacctgcgg  420 |
| ccatctgggg | atattccact | ncgatnatgt | gattaaggaa | ntccacggag | ttttacaagg  480 |
| acacgtacaa | cnacctgaaa | accnnggatg | anccccaccg | ggaancnctg | aangccatcc  540 |
| actatgcgtt | gaactgcaat | ggtttggctg | gggncctga  | acaatttaat | cncatacatc  600 |
| tggccccann | aaaggacntn | ctcganncct | tcnccgtgna | attcngttct | gatnccatca  660 |
| cagaagtctc | gaacaatcc  |            |            |            |             679 |

<210> SEQ ID NO 15
<211> LENGTH: 695
<212> TYPE: DNA
<213> ORGANISM: Homo sapiens
<220> FEATURE:
<221> NAME/KEY: modified_base
<222> LOCATION: (105)
<223> OTHER INFORMATION: Where n is a, c, g or t
<221> NAME/KEY: modified_base
<222> LOCATION: (172)
<223> OTHER INFORMATION: Where n is a, c, g or t
<221> NAME/KEY: modified_base
<222> LOCATION: (176)
<223> OTHER INFORMATION: Where n is a, c, g or t
<221> NAME/KEY: modified_base
<222> LOCATION: (179)
<223> OTHER INFORMATION: Where n is a, c, g or t
<221> NAME/KEY: modified_base
<222> LOCATION: (189)
<223> OTHER INFORMATION: Where n is a, c, g or t
<221> NAME/KEY: modified_base
<222> LOCATION: (203)
<223> OTHER INFORMATION: Where n is a, c, g or t
<221> NAME/KEY: modified_base
<222> LOCATION: (212)
<223> OTHER INFORMATION: Where n is a, c, g or t
<221> NAME/KEY: modified_base
<222> LOCATION: (219)
<223> OTHER INFORMATION: Where n is a, c, g or t
<221> NAME/KEY: modified_base -continued

```
<222> LOCATION: (221)
<223> OTHER INFORMATION: Where n is a, c, g or t
<221> NAME/KEY: modified_base
<222> LOCATION: (229)
<223> OTHER INFORMATION: Where n is a, c, g or t
<221> NAME/KEY: modified_base
<222> LOCATION: (231)
<223> OTHER INFORMATION: Where n is a, c, g or t
<221> NAME/KEY: modified_base
<222> LOCATION: (238)
<223> OTHER INFORMATION: Where n is a, c, g or t
<221> NAME/KEY: modified_base
<222> LOCATION: (242)
<223> OTHER INFORMATION: Where n is a, c, g or t
<221> NAME/KEY: modified_base
<222> LOCATION: (261)
<223> OTHER INFORMATION: Where n is a, c, g or t
<221> NAME/KEY: modified_base
<222> LOCATION: (266)
<223> OTHER INFORMATION: Where n is a, c, g or t
<221> NAME/KEY: modified_base
<222> LOCATION: (270)
<223> OTHER INFORMATION: Where n is a, c, g or t
<221> NAME/KEY: modified_base
<222> LOCATION: (278)
<223> OTHER INFORMATION: Where n is a, c, g or t
<221> NAME/KEY: modified_base
<222> LOCATION: (285)
<223> OTHER INFORMATION: Where n is a, c, g or t
<221> NAME/KEY: modified_base
<222> LOCATION: (286)
<223> OTHER INFORMATION: Where n is a, c, g or t
<221> NAME/KEY: modified_base
<222> LOCATION: (298)
<223> OTHER INFORMATION: Where n is a, c, g or t
<221> NAME/KEY: modified_base
<222> LOCATION: (311)
<223> OTHER INFORMATION: Where n is a, c, g or t
<221> NAME/KEY: modified_base
<222> LOCATION: (324)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (350)
<223> OTHER INFORMATION: Where n is a, c, g or t
<221> NAME/KEY: modified_base
<222> LOCATION: (363)
<223> OTHER INFORMATION: Where n is a, c, g or t
<221> NAME/KEY: modified_base
<222> LOCATION: (384)
<223> OTHER INFORMATION: Where n is a, c, g or t
<221> NAME/KEY: modified_base
<222> LOCATION: (391)
<223> OTHER INFORMATION: Where n is a, c, g or t
<221> NAME/KEY: modified_base
<222> LOCATION: (395)
<223> OTHER INFORMATION: Where n is a, c, g or t
<221> NAME/KEY: modified_base
<222> LOCATION: (405)
<223> OTHER INFORMATION: Where n is a, c, g or t
<221> NAME/KEY: modified_base
<222> LOCATION: (411)
<223> OTHER INFORMATION: Where n is a, c, g or t
<221> NAME/KEY: modified_base
<222> LOCATION: (424)
<223> OTHER INFORMATION: Where n is a, c, g or t
<221> NAME/KEY: modified_base
<222> LOCATION: (427)
<223> OTHER INFORMATION: Where n is a, c, g or t
<221> NAME/KEY: modified_base
<222> LOCATION: (443)
<223> OTHER INFORMATION: Where n is a, c, g or t
<221> NAME/KEY: modified_base
<222> LOCATION: (448)
<223> OTHER INFORMATION: Where n is a, c, g or t
<221> NAME/KEY: modified_base
<222> LOCATION: (453)
```

-continued

```
<223> OTHER INFORMATION: Where n is a, c, g or t
<221> NAME/KEY: modified_base
<222> LOCATION: (455)
<223> OTHER INFORMATION: Where n is a, c, g or t
<221> NAME/KEY: modified_base
<222> LOCATION: (458)
<223> OTHER INFORMATION: Where n is a, c, g or t
<221> NAME/KEY: modified_base
<222> LOCATION: (463)
<223> OTHER INFORMATION: Where n is a, c, g or t
<221> NAME/KEY: modified_base
<222> LOCATION: (467)
<223> OTHER INFORMATION: Where n is a, c, g or t
<221> NAME/KEY: modified_base
<222> LOCATION: (470)
<223> OTHER INFORMATION: Where n is a, c, g or t
<221> NAME/KEY: modified_base
<222> LOCATION: (479)
<223> OTHER INFORMATION: Where n is a, c, g or t
<221> NAME/KEY: modified_base
<222> LOCATION: (481)
<223> OTHER INFORMATION: Where n is a, c, g or t
<221> NAME/KEY: modified_base
<222> LOCATION: (484)
<223> OTHER INFORMATION: Where n is a, c, g or t
<221> NAME/KEY: modified_base
<222> LOCATION: (493)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (505)
<223> OTHER INFORMATION: Where n is a, c, g or t
<221> NAME/KEY: modified_base
<222> LOCATION: (518)
<223> OTHER INFORMATION: Where n is a, c, g or t
<221> NAME/KEY: modified_base
<222> LOCATION: (520)
<223> OTHER INFORMATION: Where n is a, c, g or t
<221> NAME/KEY: modified_base
<222> LOCATION: (523)
<223> OTHER INFORMATION: Where n is a, c, g or t
<221> NAME/KEY: modified_base
<222> LOCATION: (531)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (584)
<223> OTHER INFORMATION: Where n is a, c, g or t
<221> NAME/KEY: modified_base
<222> LOCATION: (595)
<223> OTHER INFORMATION: Where n is a, c, g or t
<221> NAME/KEY: modified_base
<222> LOCATION: (597)
<223> OTHER INFORMATION: Where n is a, c, g or t
<221> NAME/KEY: modified_base
<222> LOCATION: (609)
<223> OTHER INFORMATION: Where n is a, c, g or t
<221> NAME/KEY: modified_base
<222> LOCATION: (611)
<223> OTHER INFORMATION: Where n is a, c, g or t
<221> NAME/KEY: modified_base
<222> LOCATION: (626)
<223> OTHER INFORMATION: Where n is a, c, g or t
<221> NAME/KEY: modified_base
<222> LOCATION: (628)
<223> OTHER INFORMATION: Where n is a, c, g or t
<221> NAME/KEY: modified_base
<222> LOCATION: (651)
<223> OTHER INFORMATION: Where n is a, c, g or t
<221> NAME/KEY: modified_base
<222> LOCATION: (652)
<223> OTHER INFORMATION: Where n is a, c, g or t
<221> NAME/KEY: modified_base
<222> LOCATION: (657)
<223> OTHER INFORMATION: Where n is a, c, g or t
```

<221> NAME/KEY: modified_base
<222> LOCATION: (661)
<223> OTHER INFORMATION: Where n is a, c, g or t
<221> NAME/KEY: modified_base
<222> LOCATION: (665)
<223> OTHER INFORMATION: Where n is a, c, g or t
<221> NAME/KEY: modified_base
<222> LOCATION: (669)
<223> OTHER INFORMATION: Where n is a, c, g or t
<221> NAME/KEY: modified_base
<222> LOCATION: (672)
<223> OTHER INFORMATION: Where n is a, c, g or t
<221> NAME/KEY: modified_base
<222> LOCATION: (681)
<223> OTHER INFORMATION: Where n is a, c, g or t
<221> NAME/KEY: modified_base
<222> LOCATION: (683)
<223> OTHER INFORMATION: Where n is a, c, g or t
<221> NAME/KEY: modified_base
<222> LOCATION: (691)
<223> OTHER INFORMATION: Where n is a, c, g or t
<221> NAME/KEY: modified_base
<222> LOCATION: (693)
<223> OTHER INFORMATION: Where n is a, c, g or t

<400> SEQUENCE: 15

```
actagtggat aaaggccagg gatgctgctc aacctcctac catgtacagg gacgtctccc      60
cattacaact acccaatccg aagtgtcaac tgtgtcagga ctaanaaacc ctggttttga     120
ttaaaaaagg gcctgaaaaa agggagcca caaatctgtc tgcttcctca cnttantcnt     180
tggcaaatna gcattctgtc tcnttggctg cngcctcanc ncaaaaaanc ngaactcnat    240
cnggcccagg aatacatctc ncaatnaacn aaattganca aggcnntggg aaatgccnga    300
tgggattatc ntccgcttgt tganctttcta agtttcnttc ccttcattcn accctgccag    360
ccnagttctg ttagaaaaat gccngaattc naacnccggt tttcntactc ngaatttaga    420
tctncanaaa cttcctggcc acnattcnaa ttnanggnca cgnacanatn ccttccatna    480
ancncacccc acntttgana gccangacaa tgactgcntn aantgaaggc ntgaaggaan    540
aactttgaaa ggaaaaaaaa ctttgtttcc ggcccttcc aacncttctg tgttnancac     600
tgccttctng naaccctgga agcccngnga cagtgttaca tgttgttcta nnaaacngac    660
ncttnaatnt cnatcttccc nanaacgatt ncncc                               695
```

<210> SEQ ID NO 16
<211> LENGTH: 669
<212> TYPE: DNA
<213> ORGANISM: Homo sapiens
<220> FEATURE:
<221> NAME/KEY: modified_base
<222> LOCATION: (299)
<223> OTHER INFORMATION: Where n is a, c, g or t
<221> NAME/KEY: modified_base
<222> LOCATION: (354)
<223> OTHER INFORMATION: Where n is a, c, g or t
<221> NAME/KEY: modified_base
<222> LOCATION: (483)
<223> OTHER INFORMATION: Where n is a, c, g or t
<221> NAME/KEY: modified_base
<222> LOCATION: (555)
<223> OTHER INFORMATION: Where n is a, c, g or t
<221> NAME/KEY: modified_base
<222> LOCATION: (571)
<223> OTHER INFORMATION: Where n is a, c, g or t
<221> NAME/KEY: modified_base
<222> LOCATION: (573)
<223> OTHER INFORMATION: Where n is a, c, g or t
<221> NAME/KEY: modified_base
<222> LOCATION: (577)
<223> OTHER INFORMATION: Where n is a, c, g or t
<221> NAME/KEY: modified_base
<222> LOCATION: (642)
<223> OTHER INFORMATION: Where n is a, c, g or t
<221> NAME/KEY: modified_base
<222> LOCATION: (651)
<223> OTHER INFORMATION: Where n is a, c, g or t
<221> NAME/KEY: modified_base
<222> LOCATION: (662)
<223> OTHER INFORMATION: Where n is a, c, g or t
<221> NAME/KEY: modified_base
<222> LOCATION: (667)
<223> OTHER INFORMATION: Where n is a, c, g or t

<400> SEQUENCE: 16

```
cgccgaagca gcagcgcagg ttgtcccgt tccctccc ctcccttc tccggttgcc      60
ttcccgggcc ccttacactc cacagtcccg gtccgccat gtcccagaaa caagaagaag   120
agaaccctgc ggaggagacc ggcgaggaga agcaggacac gcaggagaaa gaaggtattc   180
tgcctgagag agctgaagag gcaaagctaa aggccaaata cccaagccta ggacaaaagc   240
ctggaggctc cgacttcctc atgaagagac tccagaaagg gcaaaagtac tttgactcng   300
gagactacaa catggccaaa gccaacatga agaataagca gctgccaagt gcangaccag   360
acaagaacct ggtgactggt gatcacatcc ccaccccaca ggatctgccc agagaaagtc   420
ctcgctcgtc accagcaagc ttgcgggtgg ccaagttgaa tgatgctgcc ggggctctgc   480
canatctgag acgcttccct ccctgcccca cccgggtcct gtgctggctc ctgcccttcc   540
tgcttttgca gccanggggtc aggaagtggc ncnggtngtg gctggaaagc aaaacccttt   600
cctgttggtg tcccacccat ggagcccctg gggcgagccc angaacttga nccttttgt    660
tntcttncc                                                            669
```

<210> SEQ ID NO 17
<211> LENGTH: 697
<212> TYPE: DNA
<213> ORGANISM: Homo sapiens
<220> FEATURE:
<221> NAME/KEY: modified_base
<222> LOCATION: (33)
<223> OTHER INFORMATION: Where n is a, c, g or t
<221> NAME/KEY: modified_base
<222> LOCATION: (48)
<223> OTHER INFORMATION: Where n is a, c, g or t
<221> NAME/KEY: modified_base
<222> LOCATION: (50)
<223> OTHER INFORMATION: Where n is a, c, g or t
<221> NAME/KEY: modified_base
<222> LOCATION: (58)
<223> OTHER INFORMATION: Where n is a, c, g or t
<221> NAME/KEY: modified_base
<222> LOCATION: (59)
<223> OTHER INFORMATION: Where n is a, c, g or t
<221> NAME/KEY: modified_base
<222> LOCATION: (60)
<223> OTHER INFORMATION: Where n is a, c, g or t
<221> NAME/KEY: modified_base
<222> LOCATION: (76)
<223> OTHER INFORMATION: Where n is a, c, g or t
<221> NAME/KEY: modified_base
<222> LOCATION: (77)
<223> OTHER INFORMATION: Where n is a, c, g or t
<221> NAME/KEY: modified_base
<222> LOCATION: (78)
<223> OTHER INFORMATION: Where n is a, c, g or t
<221> NAME/KEY: modified_base
<222> LOCATION: (90)
<223> OTHER INFORMATION: Where n is a, c, g or t
<221> NAME/KEY: modified_base
<222> LOCATION: (113)
<223> OTHER INFORMATION: Where n is a, c, g or t
<221> NAME/KEY: modified_base
<222> LOCATION: (118)

-continued

```
<223> OTHER INFORMATION: Where n is a, c, g or t
<221> NAME/KEY: modified_base
<222> LOCATION: (130)
<223> OTHER INFORMATION: Where n is a, c, g or t
<221> NAME/KEY: modified_base
<222> LOCATION: (135)
<223> OTHER INFORMATION: Where n is a, c, g or t
<221> NAME/KEY: modified_base
<222> LOCATION: (141)
<223> OTHER INFORMATION: Where n is a, c, g or t
<221> NAME/KEY: modified_base
<222> LOCATION: (143)
<223> OTHER INFORMATION: Where n is a, c, g or t
<221> NAME/KEY: modified_base
<222> LOCATION: (150)
<223> OTHER INFORMATION: Where n is a, c, g or t
<221> NAME/KEY: modified_base
<222> LOCATION: (156)
<223> OTHER INFORMATION: Where n is a, c, g or t
<221> NAME/KEY: modified_base
<222> LOCATION: (166)
<223> OTHER INFORMATION: Where n is a, c, g or t
<221> NAME/KEY: modified_base
<222> LOCATION: (167)
<223> OTHER INFORMATION: Where n is a, c, g or t
<221> NAME/KEY: modified_base
<222> LOCATION: (170)
<223> OTHER INFORMATION: Where n is a, c, g or t
<221> NAME/KEY: modified_base
<222> LOCATION: (172)
<223> OTHER INFORMATION: Where n is a, c, g or t
<221> NAME/KEY: modified_base
<222> LOCATION: (180)
<223> OTHER INFORMATION: Where n is a, c, g or t
<221> NAME/KEY: modified_base
<222> LOCATION: (181)
<223> OTHER INFORMATION: Where n is a, c, g or t
<221> NAME/KEY: modified_base
<222> LOCATION: (190)
<223> OTHER INFORMATION: Where n is a, c, g or t
<221> NAME/KEY: modified_base
<222> LOCATION: (192)
<223> OTHER INFORMATION: Where n is a, c, g or t
<221> NAME/KEY: modified_base
<222> LOCATION: (194)
<223> OTHER INFORMATION: Where n is a, c, g or t
<221> NAME/KEY: modified_base
<222> LOCATION: (199)
<223> OTHER INFORMATION: Where n is a, c, g or t
<221> NAME/KEY: modified_base
<222> LOCATION: (201)
<223> OTHER INFORMATION: Where n is a, c, g or t
<221> NAME/KEY: modified_base
<222> LOCATION: (209)
<223> OTHER INFORMATION: Where n is a, c, g or t
<221> NAME/KEY: modified_base
<222> LOCATION: (211)
<223> OTHER INFORMATION: Where n is a, c, g or t
<221> NAME/KEY: modified_base
<222> LOCATION: (224)
<223> OTHER INFORMATION: Where n is a, c, g or t
<221> NAME/KEY: modified_base
<222> LOCATION: (225)
<223> OTHER INFORMATION: Where n is a, c, g or t
<221> NAME/KEY: modified_base
<222> LOCATION: (226)
<223> OTHER INFORMATION: Where n is a, c, g or t
<221> NAME/KEY: modified_base
<222> LOCATION: (230)
<223> OTHER INFORMATION: Where n is a, c, g or t
<221> NAME/KEY: modified_base
<222> LOCATION: (233)
<223> OTHER INFORMATION: Where n is a, c, g or t
<221> NAME/KEY: modified_base
<222> LOCATION: (234)
<223> OTHER INFORMATION: Where n is a, c, g or t
<221> NAME/KEY: modified_base
<222> LOCATION: (236)
<223> OTHER INFORMATION: Where n is a, c, g or t
```

```
<221> NAME/KEY: modified_base
<222> LOCATION: (242)
<223> OTHER INFORMATION: Where n is a, c, g or t
<221> NAME/KEY: modified_base
<222> LOCATION: (244)
<223> OTHER INFORMATION: Where n is a, c, g or t
<221> NAME/KEY: modified_base
<222> LOCATION: (251)
<223> OTHER INFORMATION: Where n is a, c, g or t
<221> NAME/KEY: modified_base
<222> LOCATION: (253)
<223> OTHER INFORMATION: Where n is a, c, g or t
<221> NAME/KEY: modified_base
<222> LOCATION: (256)
<223> OTHER INFORMATION: Where n is a, c, g or t
<221> NAME/KEY: modified_base
<222> LOCATION: (268)
<223> OTHER INFORMATION: Where n is a, c, g or t
<221> NAME/KEY: modified_base
<222> LOCATION: (297)
<223> OTHER INFORMATION: Where n is a, c, g or t
<221> NAME/KEY: modified_base
<222> LOCATION: (305)
<223> OTHER INFORMATION: Where n is a, c, g or t
<221> NAME/KEY: modified_base
<222> LOCATION: (308)
<223> OTHER INFORMATION: Where n is a, c, g or t
<221> NAME/KEY: modified_base
<222> LOCATION: (311)
<223> OTHER INFORMATION: Where n is a, c, g or t
<221> NAME/KEY: modified_base
<222> LOCATION: (314)
<223> OTHER INFORMATION: Where n is a, c, g or t
<221> NAME/KEY: modified_base
<222> LOCATION: (315)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (324)
<223> OTHER INFORMATION: Where n is a, c, g or t
<221> NAME/KEY: modified_base
<222> LOCATION: (327)
<223> OTHER INFORMATION: Where n is a, c, g or t
<221> NAME/KEY: modified_base
<222> LOCATION: (333)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (343)
<223> OTHER INFORMATION: Where n is a, c, g or t
<221> NAME/KEY: modified_base
<222> LOCATION: (362)
<223> OTHER INFORMATION: Where n is a, c, g or t
<221> NAME/KEY: modified_base
<222> LOCATION: (364)
<223> OTHER INFORMATION: Where n is a, c, g or t
<221> NAME/KEY: modified_base
<222> LOCATION: (367)
<223> OTHER INFORMATION: Where n is a, c, g or t
<221> NAME/KEY: modified_base
<222> LOCATION: (368)
<223> OTHER INFORMATION: Where n is a, c, g or t
<221> NAME/KEY: modified_base
<222> LOCATION: (373)
<223> OTHER INFORMATION: Where n is a, c, g or t
<221> NAME/KEY: modified_base
<222> LOCATION: (384)
<223> OTHER INFORMATION: Where n is a, c, g or t
<221> NAME/KEY: modified_base
<222> LOCATION: (388)
<223> OTHER INFORMATION: Where n is a, c, g or t
<221> NAME/KEY: modified_base
```

-continued

```
<222> LOCATION: (394)
<223> OTHER INFORMATION: Where n is a, c, g or t
<221> NAME/KEY: modified_base
<222> LOCATION: (406)
<223> OTHER INFORMATION: Where n is a, c, g or t
<221> NAME/KEY: modified_base
<222> LOCATION: (411)
<223> OTHER INFORMATION: Where n is a, c, g or t
<221> NAME/KEY: modified_base
<222> LOCATION: (413)
<223> OTHER INFORMATION: Where n is a, c, g or t
<221> NAME/KEY: modified_base
<222> LOCATION: (423)
<223> OTHER INFORMATION: Where n is a, c, g or t
<221> NAME/KEY: modified_base
<222> LOCATION: (429)
<223> OTHER INFORMATION: Where n is a, c, g or t
<221> NAME/KEY: modified_base
<222> LOCATION: (438)
<223> OTHER INFORMATION: Where n is a, c, g or t
<221> NAME/KEY: modified_base
<222> LOCATION: (449)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (473)
<223> OTHER INFORMATION: Where n is a, c, g or t
<221> NAME/KEY: modified_base
<222> LOCATION: (476)
<223> OTHER INFORMATION: Where n is a, c, g or t
<221> NAME/KEY: modified_base
<222> LOCATION: (479)
<223> OTHER INFORMATION: Where n is a, c, g or t
<221> NAME/KEY: modified_base
<222> LOCATION: (489)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (494)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (505)
<223> OTHER INFORMATION: Where n is a, c, g or t
<221> NAME/KEY: modified_base
<222> LOCATION: (507)
<223> OTHER INFORMATION: Where n is a, c, g or t
<221> NAME/KEY: modified_base
<222> LOCATION: (508)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (523)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (530)
<223> OTHER INFORMATION: Where n is a, c, g or t
<221> NAME/KEY: modified_base
<222> LOCATION: (533)
<223> OTHER INFORMATION: Where n is a, c, g or t
<221> NAME/KEY: modified_base
<222> LOCATION: (535)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (539)
```

-continued

```
<223> OTHER INFORMATION: Where n is a, c, g or t
<221> NAME/KEY: modified_base
<222> LOCATION: (545)
<223> OTHER INFORMATION: Where n is a, c, g or t
<221> NAME/KEY: modified_base
<222> LOCATION: (548)
<223> OTHER INFORMATION: Where n is a, c, g or t
<221> NAME/KEY: modified_base
<222> LOCATION: (550)
<223> OTHER INFORMATION: Where n is a, c, g or t
<221> NAME/KEY: modified_base
<222> LOCATION: (552)
<223> OTHER INFORMATION: Where n is a, c, g or t
<221> NAME/KEY: modified_base
<222> LOCATION: (555)
<223> OTHER INFORMATION: Where n is a, c, g or t
<221> NAME/KEY: modified_base
<222> LOCATION: (562)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (568)
<223> OTHER INFORMATION: Where n is a, c, g or t
<221> NAME/KEY: modified_base
<222> LOCATION: (572)
<223> OTHER INFORMATION: Where n is a, c, g or t
<221> NAME/KEY: modified_base
<222> LOCATION: (577)
<223> OTHER INFORMATION: Where n is a, c, g or t
<221> NAME/KEY: modified_base
<222> LOCATION: (578)
<223> OTHER INFORMATION: Where n is a, c, g or t
<221> NAME/KEY: modified_base
<222> LOCATION: (580)
<223> OTHER INFORMATION: Where n is a, c, g or t
<221> NAME/KEY: modified_base
<222> LOCATION: (581)
<223> OTHER INFORMATION: Where n is a, c, g or t
<221> NAME/KEY: modified_base
<222> LOCATION: (591)
<223> OTHER INFORMATION: Where n is a, c, g or t
<221> NAME/KEY: modified_base
<222> LOCATION: (594)
<223> OTHER INFORMATION: Where n is a, c, g or t
<221> NAME/KEY: modified_base
<222> LOCATION: (622)
<223> OTHER INFORMATION: Where n is a, c, g or t
<221> NAME/KEY: modified_base
<222> LOCATION: (628)
<223> OTHER INFORMATION: Where n is a, c, g or t
<221> NAME/KEY: modified_base
<222> LOCATION: (632)
<223> OTHER INFORMATION: Where n is a, c, g or t
<221> NAME/KEY: modified_base
<222> LOCATION: (638)
<223> OTHER INFORMATION: Where n is a, c, g or t
<221> NAME/KEY: modified_base
<222> LOCATION: (642)
<223> OTHER INFORMATION: Where n is a, c, g or t
<221> NAME/KEY: modified_base
<222> LOCATION: (644)
<223> OTHER INFORMATION: Where n is a, c, g or t
<221> NAME/KEY: modified_base
<222> LOCATION: (653)
<223> OTHER INFORMATION: Where n is a, c, g or t
<221> NAME/KEY: modified_base
<222> LOCATION: (658)
<223> OTHER INFORMATION: Where n is a, c, g or t
<221> NAME/KEY: modified_base
<222> LOCATION: (662)
<223> OTHER INFORMATION: Where n is a, c, g or t
<221> NAME/KEY: modified_base
<222> LOCATION: (663)
<223> OTHER INFORMATION: Where n is a, c, g or t
```

<221> NAME/KEY: modified_base
<222> LOCATION: (665)
<223> OTHER INFORMATION: Where n is a, c, g or t
<221> NAME/KEY: modified_base
<222> LOCATION: (669)
<223> OTHER INFORMATION: Where n is a, c, g or t
<221> NAME/KEY: modified_base
<222> LOCATION: (675)
<223> OTHER INFORMATION: Where n is a, c, g or t
<221> NAME/KEY: modified_base
<222> LOCATION: (680)
<223> OTHER INFORMATION: Where n is a, c, g or t
<221> NAME/KEY: modified_base
<222> LOCATION: (686)
<223> OTHER INFORMATION: Where n is a, c, g or t
<221> NAME/KEY: modified_base
<222> LOCATION: (689)
<223> OTHER INFORMATION: Where n is a, c, g or t

<400> SEQUENCE: 17

```
gcaagatatg gacaactaag tgagaaggta atnctctact gctctagntn ctccnggcnn      60
gacgcgctga ggagannnac gctggcccan ctgccggcca cacacgggga tcntggtnat     120
gcctgcccan gggancccca ncnctcggan cccatntcac acccgnnccn tncgcccacn     180
ncctggctcn cncngcccng nccagctcnc gncccctcc gccnnnctcn ttnncntctc      240
cncncccctcc ncnacnacct cctacccncg gctccctccc cagccccccc ccgcaancct    300
ccacnacncc ntcnncncga ancnccnctc gcnctcngcc ccngcccct gcccccccgcc     360
cncnacnncg cgntcccccg cgcncgcngc ctcnccccct cccacnacag ncncacccgc     420
agncacgcnc tccgcccnct gacgccccnn cccgccgcgc tcaccttcat ggnccnacng     480
cccccgctcnc nccnctgcnc gccgncnngg cgccccgccc cnnccgngtn ccncncgnng    540
cccngcngn angcngtgcg cnncangncc gngccgnncn ncaccctccg nccnccgccc     600
cgcccgctgg gggctcccgc cncgcggntc antccccncc cntncgccca ctntccgntc     660
cnncnctcnc gctcngcgcn cgcccncccnc cccccc                              697
```

<210> SEQ ID NO 18
<211> LENGTH: 670
<212> TYPE: DNA
<213> ORGANISM: Homo sapiens
<220> FEATURE:
<221> NAME/KEY: modified_base
<222> LOCATION: (234)
<223> OTHER INFORMATION: Where n is a, c, g or t
<221> NAME/KEY: modified_base
<222> LOCATION: (292)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (437)
<223> OTHER INFORMATION: Where n is a, c, g or t
<221> NAME/KEY: modified_base
<222> LOCATION: (458)
<223> OTHER INFORMATION: Where n is a, c, g or t
<221> NAME/KEY: modified_base
<222> LOCATION: (478)
<223> OTHER INFORMATION: Where n is a, c, g or t
<221> NAME/KEY: modified_base
<222> LOCATION: (487)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base

```
<222> LOCATION: (549)
<223> OTHER INFORMATION: Where n is a, c, g or t
<221> NAME/KEY: modified_base
<222> LOCATION: (550)
<223> OTHER INFORMATION: Where n is a, c, g or t
<221> NAME/KEY: modified_base
<222> LOCATION: (557)
<223> OTHER INFORMATION: Where n is a, c, g or t
<221> NAME/KEY: modified_base
<222> LOCATION: (576)
<223> OTHER INFORMATION: Where n is a, c, g or t
<221> NAME/KEY: modified_base
<222> LOCATION: (597)
<223> OTHER INFORMATION: Where n is a, c, g or t
<221> NAME/KEY: modified_base
<222> LOCATION: (603)
<223> OTHER INFORMATION: Where n is a, c, g or t
<221> NAME/KEY: modified_base
<222> LOCATION: (604)
<223> OTHER INFORMATION: Where n is a, c, g or t
<221> NAME/KEY: modified_base
<222> LOCATION: (646)
<223> OTHER INFORMATION: Where n is a, c, g or t
<221> NAME/KEY: modified_base
<222> LOCATION: (665)
<223> OTHER INFORMATION: Where n is a, c, g or t

<400> SEQUENCE: 18
ctcgtgtgaa gggtgcagta cctaagccgg agcggggtag aggcgggccg gcaccccctt      60
ctgacctcca gtgccgccgg cctcaagatc agacatggcc cagaacttga acgacttggc     120
gggacggctg cccgccgggc cccggggcat gggcacggcc ctgaagctgt tgctgggggc     180
cggcgccgtg gcctacggtg tgcgcgaatc tgtgttcacc gtggaaggcg ggcncagagc     240
catcttcttc aatcggatcg gtggagtgca caggacacta tcctgggccg anggccttca     300
cttcaggatc cttggttcca gtaccccanc atctatgaca ttcgggccag acctcgaaaa     360
aatctcctcc ctacaggctc caaagaccta cagatggtga atatctccct gcgagtgttg     420
tctcgaccaa tgctcangaa cttcctaaca tgttccancg cctaagggct ggactacnaa     480
gaacgantgt tgccgtccat tgtcacgaag tgctcaagaa tttnggtggc caagttcaat     540
gncctcacnn ctgatcnccc agcggggcca agttancect ggttgatccc cggggancig     600 acnnaaaagg gccaaggact tcccctcatc ctggataatg tggccntcac aaagctcaac     660 tttanccacc                                                           670

<210> SEQ ID NO 19
<211> LENGTH: 606
<212> TYPE: DNA
<213> ORGANISM: Homo sapiens
<220> FEATURE:
<221> NAME/KEY: modified_base
<222> LOCATION: (506)
<223> OTHER INFORMATION: Where n is a, c, g or t

<400> SEQUENCE: 19
actagtgcca acctcagctc ccaggccagt tctctgaatg tcgaggagtt ccaggatctc      60
tggcctcagt tgtccttggt tattgatggg ggacaaattg gggatggcca gagccccgag     120
tgtcgccttg gctcaactgt ggttgatttg tctgtgcccg gaaagtttgg catcattcgt     180
ccaggctgtg ccctggaaag tactacagcc atcctccaac agaagtacgg actgctcccc     240
tcacatgcgt cctacctgtg aaactctggg aagcaggaag gcccaagacc tggtgctgga     300
tactatgtgt ctgtccactg acgactgtca aggcctcatt tgcagaggcc accggagcta     360
gggcactagc ctgactttta aggcagtgtg tctttctgag cactgtagac caagcccttg     420
```

```
gagctgctgg tttagccttg cacctgggga aaggatgtat ttatttgtat tttcatatat     480
cagccaaaag ctgaatggaa aagtttnagaa cattcctagg tggccttatt ctaataagtt     540
tcttctgtct gttttgtttt tcaattgaaa agttattaaa taacagattt agaatctagt     600
gagacc                                                                 606
```

<210> SEQ ID NO 20
<211> LENGTH: 449
<212> TYPE: DNA
<213> ORGANISM: Homo sapiens

<400> SEQUENCE: 20

```
actagtaaac aacagcagca gaaacatcag tatcagcagc gtcgccagca ggagaatatg      60
cagcgccaga gccgaggaga accccgctc cctgaggagg acctgtccaa actcttcaaa     120
ccaccacagc cgcctgccag gatggactcg ctgctcattg caggccagat aaacacttac     180
tgccagaaca tcaaggagtt cactgcccaa aacttaggca agctcttcat ggcccaggct     240
cttcaagaat acaacaacta agaaaaggaa gtttccagaa aagaagttaa catgaactct     300
tgaagtcaca ccagggcaac tcttggaaga aatatatttg catattgaaa agcacagagg     360
atttctttag tgtcattgcc gattttggct ataacagtgt ctttctagcc ataataaaat     420
aaaacaaaat cttgactgct tgctcaaaa                                       449
```

<210> SEQ ID NO 21
<211> LENGTH: 409
<212> TYPE: DNA
<213> ORGANISM: Homo sapiens

<400> SEQUENCE: 21

```
tatcaatcaa ctggtgaata attaaacaat gtgtggtgtg atcatacaaa gggtaccact      60
caatgataaa aggaacaagc tgcctatatg tggaacaaca tggatgcatt tcagaaactt     120
tatgttgagt gaaagaacaa acacggagaa catactatgt ggttctcttt atgtaacatt     180
acagaaataa aaacagaggc aaccacctt gaggcagtat ggagtgagat agactggaaa     240
aaggaaggaa ggaaactcta cgctgatgga aatgtctgtg tcttcattgg gtggtagtta     300
tgtggggata tacatttgtc aaaatttatt gaactatata ctaaagaact ctgcatttta     360
ttgggatgta ataataacct caattaaaaa gacaaaaaaa aaaaaaaaa                 409
```

<210> SEQ ID NO 22
<211> LENGTH: 649
<212> TYPE: DNA
<213> ORGANISM: Homo sapiens
<220> FEATURE:
<221> NAME/KEY: modified_base
<222> LOCATION: (263)
<223> OTHER INFORMATION: Where n is a, c, g or t
<221> NAME/KEY: modified_base
<222> LOCATION: (353)
<223> OTHER INFORMATION: Where n is a, c, g or t
<221> NAME/KEY: modified_base
<222> LOCATION: (610)
<223> OTHER INFORMATION: Where n is a, c, g or t
<221> NAME/KEY: modified_base
<222> LOCATION: (635)
<223> OTHER INFORMATION: Where n is a, c, g or t
<221> NAME/KEY: modified_base
<222> LOCATION: (646)
<223> OTHER INFORMATION: Where n is a, c, g or t

<400> SEQUENCE: 22

```
acaattttca ttatcttaag cacattgtac atttctacag aacctgtgat tattctcgca      60
```

```
tgataaggat ggtacttgca tatggtgaat tactactgtt gacagtttcc gcagaaatcc      120
tatttcagtg gaccaacatt gtggcatggc agcaaatgcc aacattttgt ggaatagcag      180
caaatctaca agagaccctg gttggttttt cgttttgttt tctttgtttt ttccccttc       240 tcctgaatca gcagggatgg aangagggta gggaagttat gaattactcc ttccagtagt      300
agctctgaag tgtcacattt aatatcagtt ttttttaaac atgattctag ttnaatgtag      360
aagagagaag aaagaggaag tgttcacttt tttaatacac tgatttagaa atttgatgtc      420
ttatatcagt agttctgagg tattgatagc ttgctttatt tctgccttta cgttgacagt      480
gttgaagcag ggtgaataac taggggcata tatattttt tttttgtaa gctgtttcat        540 gatgttttct ttggaatttc cggataagtt caggaaaaca tctgcatgtt gttatctagt     600
ctgaagttcn tatccatctc attacaacaa aaacncccag aacggnttg                  649

<210> SEQ ID NO 23
<211> LENGTH: 669
<212> TYPE: DNA
<213> ORGANISM: Homo sapiens
<220> FEATURE:
<221> NAME/KEY: modified_base
<222> LOCATION: (642)
<223> OTHER INFORMATION: Where n is a, c, g or t
<221> NAME/KEY: modified_base
<222> LOCATION: (661)
<223> OTHER INFORMATION: Where n is a, c, g or t

<400> SEQUENCE: 23
actagtgccg tactggctga aatccctgca ggaccaggaa gagaaccagt tcagactttg      60
tactctcagt caccagctct ggaattagat aaattccttg aagatgtcag gaatgggatc     120
tatcctctga cagcctttgg gctgcctcgg ccccagcagc cacagcagga ggaggtgaca     180
tcacctgtcg tgccccctc tgtcaagact ccgacacctg aaccagctga ggtggagact      240
cgcaaggtgg tgctgatgca gtgcaacatt gagtcggtgg aggagggagt caaacaccac    300
ctgacacttc tgctgaagtt ggaggacaaa ctgaaccggc acctgagctg tgacctgatg    360
ccaaatgaga atatccccga gttggcggct gagctggtgc agctgggctt cattagtgag    420
gctgaccaga gccggttgac ttctctgcta aagagactt gaacaagttc aattttgcca     480
ggaacagtac cctcaactca gccgctgtca ccgtctcctc ttagagctca ctcgggccag    540
gccctgatct gcgctgtggc tgtcctggac gtgctgcacc ctctgtcctt cccccagtc    600 agtattacct gtgaagccct tccctccttt attattcagg anggctgggg gggctccttg    660 nttctaacc                                                              669

<210> SEQ ID NO 24
<211> LENGTH: 442
<212> TYPE: DNA
<213> ORGANISM: Homo sapiens

<400> SEQUENCE: 24
actagtacca tcttgacaga ggatacatgc tcccaaaacg tttgttacca cacttaaaaa      60
tcactgccat cattaagcat cagtttcaaa attatagcca ttcatgattt acttttccca    120
gatgactatc attattctag tcctttgaat ttgtaagggg aaaaaaaaca aaaacaaaaa    180
cttacgatgc acttttctcc agcacatcag atttcaaatt gaaattaaaa gacatgctat   240
ggtaatgcac ttgctagtac tacacacttt ggtacaacaa aaacagagg caagaaacaa     300 cggaaagaga aaagccttcc tttgttggcc cttaaactga gtcaagatct gaaatgtaga    360
```
gatgatctct gacgatacct gtatgttctt attgtgtaaa taaaattgct ggtatgaaat    420
gacctaaaaa aaaaaaaaga aa    442

<210> SEQ ID NO 25
<211> LENGTH: 656
<212> TYPE: DNA
<213> ORGANISM: Homo sapiens
<220> FEATURE:
<221> NAME/KEY: modified_base
<222> LOCATION: (330)
<223> OTHER INFORMATION: Where n is a, c, g or t
<221> NAME/KEY: modified_base
<222> LOCATION: (342)
<223> OTHER INFORMATION: Where n is a, c, g or t
<221> NAME/KEY: modified_base
<222> LOCATION: (418)
<223> OTHER INFORMATION: Where n is a, c, g or t
<221> NAME/KEY: modified_base
<222> LOCATION: (548)
<223> OTHER INFORMATION: Where n is a, c, g or t
<221> NAME/KEY: modified_base
<222> LOCATION: (579)
<223> OTHER INFORMATION: Where n is a, c, g or t
<221> NAME/KEY: modified_base
<222> LOCATION: (608)
<223> OTHER INFORMATION: Where n is a, c, g or t

<400> SEQUENCE: 25
tgcaagtacc acacactgtt tgaattttgc acaaaaagtg actgtaggat caggtgatag    60
ccccggaatg tacagtgtct tggtgcacca agatgccttc taaaggctga catacctggg    120
accctaatgg ggcagagagt atagccctag cccagtggtg acatgaccac tccctttggg    180
aggcctgagg tagaggggag tggtatgtgt tttctcagtg gaagcagcac atgagtgggt    240
gacaggatgt tagataaagg ctctagttag ggtgtcattg tcatttgaga gactgacaca    300
ctcctagcag ctggtaaagg ggtgctggan gccatgagg anctctagaa acattagcat    360
gggctgatct gattacttcc tggcatcccg ctcacttta tgggaagtct tattagangg    420
atgggacagt tttccatatc cttgctgtgg agctctggaa cactctctaa atttccctct    480
attaaaaatc actgccctaa ctacacttcc tccttgaagg aatagaaatg gaactttctc    540
tgacatantt cttggcatgg ggagccagcc acaaatgana atctgaacgt gtccaggttt    600
ctcctganac tcatctacat agaattggtt aaaccctccc ttggaataag gaaaaa    656

<210> SEQ ID NO 26
<211> LENGTH: 434
<212> TYPE: DNA
<213> ORGANISM: Homo sapiens
<220> FEATURE:
<221> NAME/KEY: modified_base
<222> LOCATION: (395)
<223> OTHER INFORMATION: Where n is a, c, g or t

<400> SEQUENCE: 26
actagttcag actgccacgc caacccccaga aaatacccca catgccagaa aagtgaagtc    60
ctaggtgttt ccatctatgt ttcaatctgt ccatctacca ggcctcgcga taaaaacaaa    120
acaaaaaaac gctgccaggt tttagaagca gttctggtct caaaaccatc aggatcctgc    180
caccagggtt cttttgaaat agtaccacat gtaaaaggga atttggcttt cacttcatct    240
aataactgaa ttgtcaggct ttgattgata attgtagaaa taagtagcct tctgttgtgg    300
gaataagtta taatcagtat tcatctcttt gttttttgtc actcttttct ctctaattgt    360
gtcatttgta ctgtttgaaa aatatttctt ctatnaaatt aaactaacct gccttaaaaa    420
aaaaaaaaaa aaaa                                                               434

<210> SEQ ID NO 27
<211> LENGTH: 654
<212> TYPE: DNA
<213> ORGANISM: Homo sapiens
<220> FEATURE:
<221> NAME/KEY: modified_base
<222> LOCATION: (505)
<223> OTHER INFORMATION: Where n is a, c, g or t
<221> NAME/KEY: modified_base
<222> LOCATION: (533)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (613)
<223> OTHER INFORMATION: Where n is a, c, g or t
<221> NAME/KEY: modified_base
<222> LOCATION: (635)
<223> OTHER INFORMATION: Where n is a, c, g or t
<221> NAME/KEY: modified_base
<222> LOCATION: (638)
<223> OTHER INFORMATION: Where n is a, c, g or t

<400> SEQUENCE: 27
actagtccaa cacagtcaga aacattgttt tgaatcctct gtaaaccaag gcattaatct    60
taataaacca ggatccattt aggtaccact tgatataaaa aggatatcca taatgaatat   120
tttatactgc atcctttaca ttagccacta aatacgttat tgcttgatga agacctttca   180
cagaatccta tggattgcag catttcactt ggctacttca tacccatgcc ttaaagaggg   240
gcagtttctc aaaagcagaa acatgccgcc agttctcaag ttttcctcct aactccattt   300
gaatgtaagg gcagctggcc cccaatgtgg ggaggtccga acattttctg aattcccatt   360
ttcttgttcg cggctaaatg acagtttctg tcattactta gattccgatc tttcccaaag   420
gtgttgattt acaaagaggc cagctaatag cagaaatcat gaccctgaaa gagagatgaa   480
attcaagctg tgagccaggc agganctcag tatggcaaag gtcttgagaa tcngccattt   540
ggtacaaaaa aaatttttaaa gcntttatgt tataccatga aaccatagaa anggcaaggg   600
aattgttaag aanaatttta agtgtccaga cccanaanga aaaaaaaaaa aaaa         654

<210> SEQ ID NO 28
<211> LENGTH: 670
<212> TYPE: DNA
<213> ORGANISM: Homo sapiens
<220> FEATURE:
<221> NAME/KEY: modified_base
<222> LOCATION: (101)
<223> OTHER INFORMATION: Where n is a, c, g or t
<221> NAME/KEY: modified_base
<222> LOCATION: (226)
<223> OTHER INFORMATION: Where n is a, c, g or t
<221> NAME/KEY: modified_base
<222> LOCATION: (274)
<223> OTHER INFORMATION: Where n is a, c, g or t
<221> NAME/KEY: modified_base
<222> LOCATION: (330)
<223> OTHER INFORMATION: Where n is a, c, g or t
<221> NAME/KEY: modified_base
<222> LOCATION: (385)
<223> OTHER INFORMATION: Where n is a, c, g or t
<221> NAME/KEY: modified_base
<222> LOCATION: (392)
<223> OTHER INFORMATION: Where n is a, c, g or t

```
<221> NAME/KEY: modified_base
<222> LOCATION: (397)
<223> OTHER INFORMATION: Where n is a, c, g or t
<221> NAME/KEY: modified_base
<222> LOCATION: (402)
<223> OTHER INFORMATION: Where n is a, c, g or t
<221> NAME/KEY: modified_base
<222> LOCATION: (452)
<223> OTHER INFORMATION: Where n is a, c, g or t
<221> NAME/KEY: modified_base
<222> LOCATION: (473)
<223> OTHER INFORMATION: Where n is a, c, g or t
<221> NAME/KEY: modified_base
<222> LOCATION: (476)
<223> OTHER INFORMATION: Where n is a, c, g or t
<221> NAME/KEY: modified_base
<222> LOCATION: (532)
<223> OTHER INFORMATION: Where n is a, c, g or t
<221> NAME/KEY: modified_base
<222> LOCATION: (534)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (550)
<223> OTHER INFORMATION: Where n is a, c, g or t
<221> NAME/KEY: modified_base
<222> LOCATION: (583)
<223> OTHER INFORMATION: Where n is a, c, g or t
<221> NAME/KEY: modified_base
<222> LOCATION: (595)
<223> OTHER INFORMATION: Where n is a, c, g or t
<221> NAME/KEY: modified_base
<222> LOCATION: (604)
<223> OTHER INFORMATION: Where n is a, c, g or t
<221> NAME/KEY: modified_base
<222> LOCATION: (613)
<223> OTHER INFORMATION: Where n is a, c, g or t
<221> NAME/KEY: modified_base
<222> LOCATION: (622)
<223> OTHER INFORMATION: Where n is a, c, g or t
<221> NAME/KEY: modified_base
<222> LOCATION: (643)
<223> OTHER INFORMATION: Where n is a, c, g or t
<221> NAME/KEY: modified_base
<222> LOCATION: (669)
<223> OTHER INFORMATION: Where n is a, c, g or t

<400> SEQUENCE: 28
cgtgtgcaca tactgggagg atttccacag ctgcacggtc acagcccttA cggattgcca      60
ggaaggggcg aaagatatgt gggataaact gagaaaagaa nccaaaaacc tcaacatcca     120
aggcagctta ttcgaactct gcggcagcgg caacggggcg gcgggtccc  tgctcccggc     180
gttcccggtg ctcctggtgt ctctctcggc agctttagcg acctgncttt ccttctgagc     240
gtggggccag ctcccccccgc ggcgcccacc cacnctcact ccatgctccc ggaaatcgag     300
aggaagatca ttagttcttt ggggacgttn gtgattctct gtgatgctga aaaacactca     360
tatagggaat gtgggaaatc ctganctctt tnttatntcg tntgatttct tgtgttttat     420
ttgccaaaat gttaccaatc agtgaccaac cnagcacagc caaaaatcgg acntcngctt     480
tagtccgtct tcacacacag aataagaaaa cggcaaaccc accccacttt tnantttnat     540
tattactaan tttttctgt tgggcaaaag aatctcagga acngccctgg ggccnccgta     600
ctanagttaa ccnagctagt tncatgaaaa atgatgggct ccncctcaat gggaaagcca     660
agaaaaagnc                                                            670

<210> SEQ ID NO 29
<211> LENGTH: 551
<212> TYPE: DNA
```

```
<213> ORGANISM: Homo sapiens
<220> FEATURE:
<221> NAME/KEY: modified_base
<222> LOCATION: (336)
<223> OTHER INFORMATION: Where n is a, c, g or t
<221> NAME/KEY: modified_base
<222> LOCATION: (474)
<223> OTHER INFORMATION: Where n is a, c, g or t
<221> NAME/KEY: modified_base
<222> LOCATION: (504)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (523)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (547)
<223> OTHER INFORMATION: Where n is a, c, g or t

<400> SEQUENCE: 29
actagtcctc cacagcctgt gaatccccct agacctttca agcatagtga gcggagaaga      60
agatctcagc gtttagccac cttacccatg cctgatgatt ctgtagaaaa ggtttcttct    120
ccctctccag ccactgatgg gaaagtattc tccatcagtt ctcaaaatca gcaagaatct    180
tcagtaccag aggtgcctga tgttgcacat ttgccacttg agaagctggg accctgtctc    240
cctcttgact taagtcgtgg ttcagaagtt acagcaccgg tagcctcaga ttcctcttac    300
cgtaatgaat gtcccagggc agaaaaagag gatacncaga tgcttccaaa tccttcttcc    360
aaagcaatag ctgatgggaa gaggagctcc agcagcagca ggaatatcga aaacagaaaa    420
aaaagtgaaa ttgggaagac aaaagctcaa cagcatttgg taaggagaaa aganaagatg    480
aggaaggaag agagaagaga gacnaagatc nctacggacc gnnncggaag aagaagaagn    540
aaaaaanaaa a                                                          551

<210> SEQ ID NO 30
<211> LENGTH: 684
<212> TYPE: DNA
<213> ORGANISM: Homo sapiens
<220> FEATURE:
<221> NAME/KEY: modified_base
<222> LOCATION: (545)
<223> OTHER INFORMATION: Where n is a, c, g or t
<221> NAME/KEY: modified_base
<222> LOCATION: (570)
<223> OTHER INFORMATION: Where n is a, c, g or t
<221> NAME/KEY: modified_base
<222> LOCATION: (606)
<223> OTHER INFORMATION: Where n is a, c, g or t
<221> NAME/KEY: modified_base
<222> LOCATION: (657)
<223> OTHER INFORMATION: Where n is a, c, g or t
<221> NAME/KEY: modified_base
<222> LOCATION: (684)
<223> OTHER INFORMATION: Where n is a, c, g or t

<400> SEQUENCE: 30
actagttcta tctggaaaaa gcccggggttg gaagaagctg tggagagtgc gtgtgcaatg     60
cgagactcat ttcttggaag catccctggc aaaaatgcag ctgagtacaa ggttatcact   120
```

```
gtgatagaac ctggactgct ttttgagata atagagatgc tgcagtctga agagacttcc      180
agcacctctc agttgaatga attaatgatg gcttctgagt caactttact ggctcaggaa      240
ccacgagaga tgactgcaga tgtaatcgag cttaaaggga aattcctcat caacttagaa      300
ggtggtgata ttcgtgaaga gtcttcctat aaagtaattg tcatgccgac tacgaaagaa      360
aaatgccccc gttgttggaa gtatacacgc ggagtcttca gatacactgt gtcctcgatg      420
tgcagaagtt gtcagtggga aaatagtatt aacagctcac tcgagcaaga accctcctga      480
cagtactggg ctagaagttt ggatggatta tttacaatat aggaaagaaa gccaagaatt      540
aggtnatgag tggatgagta aatggtggan gatggggaat tcaaatcaga attatggaag      600
aagttnttcc tgttactata gaaggaatt atgtttattt acatgcagaa aatatanatg      660
tgtggtgtgt accgtggatg gaan                                             684
```

<210> SEQ ID NO 31
<211> LENGTH: 654
<212> TYPE: DNA
<213> ORGANISM: Homo sapiens
<220> FEATURE:
<221> NAME/KEY: modified_base
<222> LOCATION: (326)
<223> OTHER INFORMATION: Where n is a, c, g or t
<221> NAME/KEY: modified_base
<222> LOCATION: (582)
<223> OTHER INFORMATION: Where n is a, c, g or t
<221> NAME/KEY: modified_base
<222> LOCATION: (651)
<223> OTHER INFORMATION: Where n is a, c, g or t

<400> SEQUENCE: 31

```
gcgcagaaaa ggaaccaata tttcagaaac aagcttaata ggaacagctg cctgtacatc       60
aacatcttct cagaatgacc cagaagttat catcgtggga gctggcgtgc ttggctctgc      120
tttggcagct gtgctttcca gagatggaag aaaggtgaca gtcattgaga gagacttaaa      180
agagcctgac agaatagttg gagaattcct gcagccgggt ggttatcatg ttctcaaaga      240
ccttggtctt ggagatacag tggaaggtct tgatgcccag gttgtaaatg gttacatgat      300
tcatgatcag ggaaagcaaa tcagangttc agattcctta ccctctgtca gaaaacaatc      360
aagtgcagag tggaagagct ttccatcacg gaagattcat catgagtctc cggaaagcag      420
ctatggcaga gcccaatgca agtttattg aaggtgttgt gttacagtta ttagaggaag      480
atgatgttgt gatgggagtt cagtacaagg ataaagagac tgggagatat caaggaactc      540
catgctccac tgactgttgt tgcagatggg cttttctcca anttcaggaa aagcctggtc      600
tcaataaagt ttcctgtatca ctcatttggt tggcttctta tgaagaatgc nccc           654
```

<210> SEQ ID NO 32
<211> LENGTH: 673
<212> TYPE: DNA
<213> ORGANISM: Homo sapiens
<220> FEATURE:
<221> NAME/KEY: modified_base
<222> LOCATION: (376)
<223> OTHER INFORMATION: Where n is a, c, g or t
<221> NAME/KEY: modified_base
<222> LOCATION: (545)
<223> OTHER INFORMATION: Where n is a, c, g or t
<221> NAME/KEY: modified_base
<222> LOCATION: (627)
<223> OTHER INFORMATION: Where n is a, c, g or t

<400> SEQUENCE: 32

```
actagtgaag aaaaagaaat tctgatacgg gacaaaaatg ctcttcaaaa catcattctt      60
tatcacctga caccaggagt tttcattgga aaaggatttg aacctggtgt tactaacatt     120
ttaaagacca cacaaggaag caaaatcttt ctgaaagaag taaatgatac acttctggtg     180
aatgaattga aatcaaaaga atctgacatc atgacaacaa atggtgtaat tcatgttgta     240
gataaactcc tctatccagc agacacacct gttggaaatg atcaactgct ggaaatactt     300
aataaattaa tcaaatacat ccaaattaag tttgttcgtg gtagcacctt caaagaaatc     360
cccgtgactg tctatnagcc aattattaaa aaatacacca aaatcattga tgggagtgcc     420
tgtgggaaat aactgaaaaa gagaccgaga agaacgaatc attacaggtc ctgaaataaa     480
atacctagga tttctactgg aggtggagaa acagaagaac tctgaagaaa ttgttacaag     540
aagangtccc aaggtcacca aattcattga aggtggtgat ggtctttatt tgaagatgaa     600
gaaattaaaa gacgcttcag ggagacnccc catgaaggaa ttgccagcca caaaaaaatt     660
cagggattag aaa                                                        673
```

<210> SEQ ID NO 33
<211> LENGTH: 673
<212> TYPE: DNA
<213> ORGANISM: Homo sapiens
<220> FEATURE:
<221> NAME/KEY: modified_base
<222> LOCATION: (325)
<223> OTHER INFORMATION: Where n is a, c, g or t
<221> NAME/KEY: modified_base
<222> LOCATION: (419)
<223> OTHER INFORMATION: Where n is a, c, g or t
<221> NAME/KEY: modified_base
<222> LOCATION: (452)
<223> OTHER INFORMATION: Where n is a, c, g or t
<221> NAME/KEY: modified_base
<222> LOCATION: (532)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (571)
<223> OTHER INFORMATION: Where n is a, c, g or t
<221> NAME/KEY: modified_base
<222> LOCATION: (600)
<223> OTHER INFORMATION: Where n is a, c, g or t
<221> NAME/KEY: modified_base
<222> LOCATION: (616)
<223> OTHER INFORMATION: Where n is a, c, g or t
<221> NAME/KEY: modified_base
<222> LOCATION: (651)
<223> OTHER INFORMATION: Where n is a, c, g or t
<221> NAME/KEY: modified_base
<222> LOCATION: (653)
<223> OTHER INFORMATION: Where n is a, c, g or t
<221> NAME/KEY: modified_base
<222> LOCATION: (672)
<223> OTHER INFORMATION: Where n is a, c, g or t
<400> SEQUENCE: 33

```
actagttatt tactttcctc cgcttcagaa ggttttttcag actgagagcc taagcatact     60
ggatctgttg tttcttttgg gtctcacctc atcagtgtgc atagtggcag aaattataaa    120
gaaggttgaa aggagcaggg aaaagatcca gaagcatgtt agttcgacat catcatcttt    180
tcttgaagta tgatgcatat tgcattattt tatttgcaaa ctaggaattg cagtctgagg    240
atcatttaga agggcaagtt caagaggata tgaagatttg agaacttttt aactattcat    300
```

-continued

```
tgactaaaaa tgaacattaa tgttnaagac ttaagacttt aacctgctgg cagtcccaaa      360
tgaaattatg caactttgat atcatattcc ttgatttaaa ttgggctttt gtgattgant      420
gaaactttat aaagcatatg gtcagttatt tnattaaaaa ggcaaaacct gaaccacctt      480
ctgcacttaa agaagtctaa cagtacaaat acctatctat cttagatgga tntatttntt      540 tntatttta aatattgtac tatttatggt nggtggggct ttcttactaa tacacaaatn      600
aatttatcat ttcaanggca ttctatttgg gtttagaagt tgattccaag nantgcatat      660
ttcgctactg tnt                                                        673
```

<210> SEQ ID NO 34
<211> LENGTH: 684
<212> TYPE: DNA
<213> ORGANISM: Homo sapiens
<220> FEATURE:
<221> NAME/KEY: modified_base
<222> LOCATION: (414)
<223> OTHER INFORMATION: Where n is a, c, g or t
<221> NAME/KEY: modified_base
<222> LOCATION: (472)
<223> OTHER INFORMATION: Where n is a, c, g or t
<221> NAME/KEY: modified_base
<222> LOCATION: (480)
<223> OTHER INFORMATION: Where n is a, c, g or t
<221> NAME/KEY: modified_base
<222> LOCATION: (490)
<223> OTHER INFORMATION: Where n is a, c, g or t
<221> NAME/KEY: modified_base
<222> LOCATION: (503)
<223> OTHER INFORMATION: Where n is a, c, g or t
<221> NAME/KEY: modified_base
<222> LOCATION: (507)
<223> OTHER INFORMATION: Where n is a, c, g or t
<221> NAME/KEY: modified_base
<222> LOCATION: (508)
<223> OTHER INFORMATION: Where n is a, c, g or t
<221> NAME/KEY: modified_base
<222> LOCATION: (513)
<223> OTHER INFORMATION: Where n is a, c, g or t
<221> NAME/KEY: modified_base
<222> LOCATION: (523)
<223> OTHER INFORMATION: Where n is a, c, g or t
<221> NAME/KEY: modified_base
<222> LOCATION: (574)
<223> OTHER INFORMATION: Where n is a, c, g or t
<221> NAME/KEY: modified_base
<222> LOCATION: (575)
<223> OTHER INFORMATION: Where n is a, c, g or t
<221> NAME/KEY: modified_base
<222> LOCATION: (598)
<223> OTHER INFORMATION: Where n is a, c, g or t
<221> NAME/KEY: modified_base
<222> LOCATION: (659)
<223> OTHER INFORMATION: Where n is a, c, g or t
<221> NAME/KEY: modified_base
<222> LOCATION: (662)
<223> OTHER INFORMATION: Where n is a, c, g or t
<221> NAME/KEY: modified_base
<222> LOCATION: (675)
<223> OTHER INFORMATION: Where n is a, c, g or t

<400> SEQUENCE: 34

```
actagtttat tcaagaaaag aacttactga ttcctctgtt cctaaagcaa gagtggcagg       60
tgatcagggc tggtgtagca tccggttcct ttagtgcagc taactgcatt tgtcactgat      120
gaccaaggag gaaatcacta agacatttga gaagcagtgg tatgaacgtt cttggacaag      180
ccacagttct gagccttaac cctgtagttt gcacacaaga acgagctcca cctcccttc       240 ttcaggagga atctgtgcgg atagattggc tggacttttc aatggttctg ggttgcaagt      300
gggcactgtt atggctgggt atggagcgga cagccccagg aatcagagcc tcagcccggc      360
```

-continued

```
tgcctggttg gaaggtacag gtgttcagca ccttcggaaa aagggcataa agtngtgggg    420
gacaattctc agtccaagaa gaatgcattg accattgctg gctatttgct tncctagtan    480
gaattggatn cattttttgac cangatnntt ctnctatgct ttnttgcaat gaaatcaaat   540
cccgcattat ctacaagtgg tatgaagtcc tgcnnccccc agagaggctg ttcaggcnat    600
gtcttccaag ggcagggtgg gttacaccat tttacctccc ctctccccccc agattatgna   660 cncagaagga atttntttcc tccc                                            684
```

```
<210> SEQ ID NO 35
<211> LENGTH: 614
<212> TYPE: DNA
<213> ORGANISM: Homo sapiens
<220> FEATURE:
<221> NAME/KEY: modified_base
<222> LOCATION: (17)
<223> OTHER INFORMATION: Where n is a, c, g or t
<221> NAME/KEY: modified_base
<222> LOCATION: (20)
<223> OTHER INFORMATION: Where n is a, c, g or t
<221> NAME/KEY: modified_base
<222> LOCATION: (152)
<223> OTHER INFORMATION: Where n is a, c, g or t
<221> NAME/KEY: modified_base
<222> LOCATION: (223)
<223> OTHER INFORMATION: Where n is a, c, g or t
<221> NAME/KEY: modified_base
<222> LOCATION: (267)
<223> OTHER INFORMATION: Where n is a, c, g or t
<221> NAME/KEY: modified_base
<222> LOCATION: (287)
<223> OTHER INFORMATION: Where n is a, c, g or t
<221> NAME/KEY: modified_base
<222> LOCATION: (304)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (316)
<223> OTHER INFORMATION: Where n is a, c, g or t
<221> NAME/KEY: modified_base
<222> LOCATION: (319)
<223> OTHER INFORMATION: Where n is a, c, g or t
<221> NAME/KEY: modified_base
<222> LOCATION: (321)
<223> OTHER INFORMATION: Where n is a, c, g or t
<221> NAME/KEY: modified_base
<222> LOCATION: (355)
<223> OTHER INFORMATION: Where n is a, c, g or t
<221> NAME/KEY: modified_base
<222> LOCATION: (365)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (391)
<223> OTHER INFORMATION: Where n is a, c, g or t
<221> NAME/KEY: modified_base
<222> LOCATION: (407)
<223> OTHER INFORMATION: Where n is a, c, g or t
<221> NAME/KEY: modified_base
<222> LOCATION: (419)
<223> OTHER INFORMATION: Where n is a, c, g or t
<221> NAME/KEY: modified_base
<222> LOCATION: (428)
<223> OTHER INFORMATION: Where n is a, c, g or t
<221> NAME/KEY: modified_base
<222> LOCATION: (434)
<223> OTHER INFORMATION: Where n is a, c, g or t
<221> NAME/KEY: modified_base
<222> LOCATION: (464)
<223> OTHER INFORMATION: Where n is a, c, g or t
```

<221> NAME/KEY: modified_base
<222> LOCATION: (467)
<223> OTHER INFORMATION: Where n is a, c, g or t
<221> NAME/KEY: modified_base
<222> LOCATION: (477)
<223> OTHER INFORMATION: Where n is a, c, g or t
<221> NAME/KEY: modified_base
<222> LOCATION: (480)
<223> OTHER INFORMATION: Where n is a, c, g or t
<221> NAME/KEY: modified_base
<222> LOCATION: (495)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (505)
<223> OTHER INFORMATION: Where n is a, c, g or t
<221> NAME/KEY: modified_base
<222> LOCATION: (515)
<223> OTHER INFORMATION: Where n is a, c, g or t
<221> NAME/KEY: modified_base
<222> LOCATION: (516)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (547)
<223> OTHER INFORMATION: Where n is a, c, g or t
<221> NAME/KEY: modified_base
<222> LOCATION: (549)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (572)
<223> OTHER INFORMATION: Where n is a, c, g or t
<221> NAME/KEY: modified_base
<222> LOCATION: (576)
<223> OTHER INFORMATION: Where n is a, c, g or t
<221> NAME/KEY: modified_base
<222> LOCATION: (578)
<223> OTHER INFORMATION: Where n is a, c, g or t

<400> SEQUENCE: 35

| | | | | | |
|---|---|---|---|---|---|
| actagtccaa | cgcgttngcn | aatattcccc | tggtagccta | cttccttacc | cccgaatatt   60 |
| ggtaagatcg | agcaatggct | tcaggacatg | ggttctcttc | tcctgtgatc | attcaagtgc  120 |
| tcactgcatg | aagactggct | tgtctcagtg | tntcaacctc | accagggctg | tctcttggtc  180 |
| cacacctcgc | tccctgttag | tgccgtatga | cagcccccat | canatgacct | tggccaagtc  240 |
| acggtttctc | tgtggtcaat | gttggtnggc | tgattggtgg | aaagtanggt | ggaccaaagg  300 |
| aagncncgtg | agcagncanc | nccagttctg | caccagcagc | gcctccgtcc | tactngggtg  360 |
| ttccngtttc | tcctggcccct | gngtgggcta | nggcctgatt | cgggaanatg | cctttgcang  420 |
| gaaggganga | taantgggat | ctaccaattg | attctggcaa | aacnatntct | aagattnttn  480 |
| tgctttatgt | ggganacana | tctanctctc | atttnntgct | gnanatnaca | ccctactcgt  540 |
| gntcgancnc | gtcttcgatt | ttcgganaca | cnccantnaa | tactggcgtt | ctgttgttaa  600 |
| aaaaaaaaaa | aaaa | | | |   614 |

```
<210> SEQ ID NO 36
<211> LENGTH: 686
<212> TYPE: DNA
<213> ORGANISM: Homo sapiens
<220> FEATURE:
<221> NAME/KEY: modified_base
<222> LOCATION: (222)
<223> OTHER INFORMATION: Where n is a, c, g or t
<221> NAME/KEY: modified_base
<222> LOCATION: (224)
<223> OTHER INFORMATION: Where n is a, c, g or t
<221> NAME/KEY: modified_base
<222> LOCATION: (237)
<223> OTHER INFORMATION: Where n is a, c, g or t
<221> NAME/KEY: modified_base
<222> LOCATION: (264)
<223> OTHER INFORMATION: Where n is a, c, g or t
<221> NAME/KEY: modified_base
<222> LOCATION: (285)
<223> OTHER INFORMATION: Where n is a, c, g or t
<221> NAME/KEY: modified_base
<222> LOCATION: (548)
<223> OTHER INFORMATION: Where n is a, c, g or t
<221> NAME/KEY: modified_base
<222> LOCATION: (551)
<223> OTHER INFORMATION: Where n is a, c, g or t
<221> NAME/KEY: modified_base
<222> LOCATION: (628)
<223> OTHER INFORMATION: Where n is a, c, g or t
<221> NAME/KEY: modified_base
<222> LOCATION: (643)
<223> OTHER INFORMATION: Where n is a, c, g or t
<221> NAME/KEY: modified_base
<222> LOCATION: (645)
<223> OTHER INFORMATION: Where n is a, c, g or t
<221> NAME/KEY: modified_base
<222> LOCATION: (665)
<223> OTHER INFORMATION: Where n is a, c, g or t
<221> NAME/KEY: modified_base
<222> LOCATION: (674)
<223> OTHER INFORMATION: Where n is a, c, g or t

<400> SEQUENCE: 36
gtggctggcc cggttctccg cttctcccca tccctactt tcctccctcc ctcccttcc        60 ctccctcgtc gactgttgct tgctggtcgc agactccctg accctccct caccccctcc      120 taacctcggt gccaccggat tgccttctt ttcctgttgc ccagcccagc cctagtgtca      180
gggcgggggc ctggagcagc ccgaggcact gcagcagaag ananaaaaga cacgacnaac    240
ctcagctcgc cagtccggtc gctngcttcc cgccgcatgg caatnagaca gacgccgctc    300
acctgctctg ggcacacgcg acccgtggtt gatttggcct tcagtggcat caccttatg    360 ggtatttctt aatcagcgct tgcaaagatg gttaacctat gctacgccag ggagatacag    420
gagactggat tggaacattt ttgggtctaa aaggtctgtt tggggtgcaa cactgaataa    480
ggatgccacc aaagcagcta cagcagctgc agatttcaca gcccaagtgt gggatgctgt    540
ctcagganat naattgataa cctggctcat aacacattgt caagaatgtg gatttcccca    600
ggatattatt atttgtttac cggggganag gataactgtt tcncntattt taattgaaca    660
aactnaaaca aaanctaagg aaatcc                                         686

<210> SEQ ID NO 37
<211> LENGTH: 681
<212> TYPE: DNA
<213> ORGANISM: Homo sapiens
<220> FEATURE:
<221> NAME/KEY: modified_base
<222> LOCATION: (7)
<223> OTHER INFORMATION: Where n is a, c, g or t
<221> NAME/KEY: modified_base
```

-continued

```
<222> LOCATION: (10)
<223> OTHER INFORMATION: Where n is a, c, g or t
<221> NAME/KEY: modified_base
<222> LOCATION: (11)
<223> OTHER INFORMATION: Where n is a, c, g or t
<221> NAME/KEY: modified_base
<222> LOCATION: (19)
<223> OTHER INFORMATION: Where n is a, c, g or t
<221> NAME/KEY: modified_base
<222> LOCATION: (25)
<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (46)
<223> OTHER INFORMATION: Where n is a, c, g or t
<221> NAME/KEY: modified_base
<222> LOCATION: (53)
<223> OTHER INFORMATION: Where n is a, c, g or t
<221> NAME/KEY: modified_base
<222> LOCATION: (77)
<223> OTHER INFORMATION: Where n is a, c, g or t
<221> NAME/KEY: modified_base
<222> LOCATION: (93)
<223> OTHER INFORMATION: Where n is a, c, g or t
<221> NAME/KEY: modified_base
<222> LOCATION: (101)
<223> OTHER INFORMATION: Where n is a, c, g or t
<221> NAME/KEY: modified_base
<222> LOCATION: (103)
<223> OTHER INFORMATION: Where n is a, c, g or t
<221> NAME/KEY: modified_base
<222> LOCATION: (109)
<223> OTHER INFORMATION: Where n is a, c, g or t
<221> NAME/KEY: modified_base
<222> LOCATION: (115)
<223> OTHER INFORMATION: Where n is a, c, g or t
<221> NAME/KEY: modified_base
<222> LOCATION: (123)
<223> OTHER INFORMATION: Where n is a, c, g or t
<221> NAME/KEY: modified_base
<222> LOCATION: (128)
<223> OTHER INFORMATION: Where n is a, c, g or t
<221> NAME/KEY: modified_base
<222> LOCATION: (139)
<223> OTHER INFORMATION: Where n is a, c, g or t
<221> NAME/KEY: modified_base
<222> LOCATION: (157)
<223> OTHER INFORMATION: Where n is a, c, g or t
<221> NAME/KEY: modified_base
<222> LOCATION: (175)
<223> OTHER INFORMATION: Where n is a, c, g or t
<221> NAME/KEY: modified_base
<222> LOCATION: (180)
<223> OTHER INFORMATION: Where n is a, c, g or t
<221> NAME/KEY: modified_base
<222> LOCATION: (192)
<223> OTHER INFORMATION: Where n is a, c, g or t
<221> NAME/KEY: modified_base
<222> LOCATION: (193)
<223> OTHER INFORMATION: Where n is a, c, g or t
<221> NAME/KEY: modified_base
<222> LOCATION: (194)
<223> OTHER INFORMATION: Where n is a, c, g or t
<221> NAME/KEY: modified_base
<222> LOCATION: (212)
<223> OTHER INFORMATION: Where n is a, c, g or t
<221> NAME/KEY: modified_base
<222> LOCATION: (218)
<223> OTHER INFORMATION: Where n is a, c, g or t
<221> NAME/KEY: modified_base
<222> LOCATION: (226)
<223> OTHER INFORMATION: Where n is a, c, g or t
<221> NAME/KEY: modified_base
<222> LOCATION: (227)
<223> OTHER INFORMATION: Where n is a, c, g or t
<221> NAME/KEY: modified_base
<222> LOCATION: (233)
```

-continued

```
<223> OTHER INFORMATION: Where n is a, c, g or t
<221> NAME/KEY: modified_base
<222> LOCATION: (240)
<223> OTHER INFORMATION: Where n is a, c, g or t
<221> NAME/KEY: modified_base
<222> LOCATION: (241)
<223> OTHER INFORMATION: Where n is a, c, g or t
<221> NAME/KEY: modified_base
<222> LOCATION: (259)
<223> OTHER INFORMATION: Where n is a, c, g or t
<221> NAME/KEY: modified_base
<222> LOCATION: (260)
<223> OTHER INFORMATION: Where n is a, c, g or t
<221> NAME/KEY: modified_base
<222> LOCATION: (267)
<223> OTHER INFORMATION: Where n is a, c, g or t
<221> NAME/KEY: modified_base
<222> LOCATION: (288)
<223> OTHER INFORMATION: Where n is a, c, g or t
<221> NAME/KEY: modified_base
<222> LOCATION: (296)
<223> OTHER INFORMATION: Where n is a, c, g or t
<221> NAME/KEY: modified_base
<222> LOCATION: (297)
<223> OTHER INFORMATION: Where n is a, c, g or t
<221> NAME/KEY: modified_base
<222> LOCATION: (298)
<223> OTHER INFORMATION: Where n is a, c, g or t
<221> NAME/KEY: modified_base
<222> LOCATION: (312)
<223> OTHER INFORMATION: Where n is a, c, g or t
<221> NAME/KEY: modified_base
<222> LOCATION: (313)
<223> OTHER INFORMATION: Where n is a, c, g or t
<221> NAME/KEY: modified_base
<222> LOCATION: (314)
<223> OTHER INFORMATION: Where n is a, c, g or t
<221> NAME/KEY: modified_base
<222> LOCATION: (320)
<223> OTHER INFORMATION: Where n is a, c, g or t
<221> NAME/KEY: modified_base
<222> LOCATION: (325)
<223> OTHER INFORMATION: Where n is a, c, g or t
<221> NAME/KEY: modified_base
<222> LOCATION: (330)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (345)
<223> OTHER INFORMATION: Where n is a, c, g or t
<221> NAME/KEY: modified_base
<222> LOCATION: (346)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (353)
<223> OTHER INFORMATION: Where n is a, c, g or t
<221> NAME/KEY: modified_base
<222> LOCATION: (356)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (385)
<223> OTHER INFORMATION: Where n is a, c, g or t
<221> NAME/KEY: modified_base
<222> LOCATION: (400)
<223> OTHER INFORMATION: Where n is a, c, g or t
<221> NAME/KEY: modified_base
<222> LOCATION: (427)
<223> OTHER INFORMATION: Where n is a, c, g or t
<221> NAME/KEY: modified_base
<222> LOCATION: (481)
<223> OTHER INFORMATION: Where n is a, c, g or t
```

```
<221> NAME/KEY: modified_base
<222> LOCATION: (484)
<223> OTHER INFORMATION: Where n is a, c, g or t
<221> NAME/KEY: modified_base
<222> LOCATION: (485)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (505)
<223> OTHER INFORMATION: Where n is a, c, g or t
<221> NAME/KEY: modified_base
<222> LOCATION: (515)
<223> OTHER INFORMATION: Where n is a, c, g or t
<221> NAME/KEY: modified_base
<222> LOCATION: (533)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (544)
<223> OTHER INFORMATION: Where n is a, c, g or t
<221> NAME/KEY: modified_base
<222> LOCATION: (554)
<223> OTHER INFORMATION: Where n is a, c, g or t
<221> NAME/KEY: modified_base
<222> LOCATION: (557)
<223> OTHER INFORMATION: Where n is a, c, g or t
<221> NAME/KEY: modified_base
<222> LOCATION: (560)
<223> OTHER INFORMATION: Where n is a, c, g or t
<221> NAME/KEY: modified_base
<222> LOCATION: (561)
<223> OTHER INFORMATION: Where n is a, c, g or t
<221> NAME/KEY: modified_base
<222> LOCATION: (564)
<223> OTHER INFORMATION: Where n is a, c, g or t
<221> NAME/KEY: modified_base
<222> LOCATION: (575)
<223> OTHER INFORMATION: Where n is a, c, g or t
<221> NAME/KEY: modified_base
<222> LOCATION: (583)
<223> OTHER INFORMATION: Where n is a, c, g or t
<221> NAME/KEY: modified_base
<222> LOCATION: (589)
<223> OTHER INFORMATION: Where n is a, c, g or t
<221> NAME/KEY: modified_base
<222> LOCATION: (595)
<223> OTHER INFORMATION: Where n is a, c, g or t
<221> NAME/KEY: modified_base
<222> LOCATION: (607)
<223> OTHER INFORMATION: Where n is a, c, g or t
<221> NAME/KEY: modified_base
<222> LOCATION: (619)
<223> OTHER INFORMATION: Where n is a, c, g or t
<221> NAME/KEY: modified_base
<222> LOCATION: (628)
<223> OTHER INFORMATION: Where n is a, c, g or t
<221> NAME/KEY: modified_base
<222> LOCATION: (634)
<223> OTHER INFORMATION: Where n is a, c, g or t
<221> NAME/KEY: modified_base
<222> LOCATION: (640)
<223> OTHER INFORMATION: Where n is a, c, g or t
<221> NAME/KEY: modified_base
<222> LOCATION: (645)
<223> OTHER INFORMATION: Where n is a, c, g or t
<221> NAME/KEY: modified_base
<222> LOCATION: (657)
<223> OTHER INFORMATION: Where n is a, c, g or t
<221> NAME/KEY: modified_base
<222> LOCATION: (670)
<223> OTHER INFORMATION: Where n is a, c, g or t

<400> SEQUENCE: 37
gagacanacn naacgtcang agaanaaaag angcatggaa cacaanccag gcncgatggc    60
```

```
caccttccca ccagcancca gcgccccca gcngcccca ngccggang accangactc    120 cancctgnat caatctganc tctattcctg gcccatncct acctcggagg tggangccgn    180
aaaggtcgca cnnncagaga agctgctgcc ancaccancc gccccnnccc tgncgggctn    240
nataggaaac tggtgaccnn gctgcanaat tcatacagga gcacgcgang ggcacnnnct    300
cacactgagt tnnngatgan gcctnaccan ggacctnccc cagcnnattg annacnggac    360
tgcggaggaa ggaagacccc gnacnggatc ctggccggcn tgccacccc ccaccctag    420 gattatnccc cttgactgag tctctgaggg gctacccgaa cccgcctcca ttccctacca    480
natnntgctc natcgggact gacangctgg ggatnggagg ggctatcccc cancatcccc    540
tnanaccaac agcnacngan natngggggct cccngggtc ggngcaacnc tcctncaccc    600
cggcgcnggc cttcggtgnt gtcctccntc aacnaattcc naaanggcgg gccccccngt    660
ggactcctcn ttgttccctc c                                               681
```

<210> SEQ ID NO 38
<211> LENGTH: 687
<212> TYPE: DNA
<213> ORGANISM: Homo sapiens
<220> FEATURE:
<221> NAME/KEY: modified_base
<222> LOCATION: (3)
<223> OTHER INFORMATION: Where n is a, c, g or t
<221> NAME/KEY: modified_base
<222> LOCATION: (30)
<223> OTHER INFORMATION: Where n is a, c, g or t
<221> NAME/KEY: modified_base
<222> LOCATION: (132)
<223> OTHER INFORMATION: Where n is a, c, g or t
<221> NAME/KEY: modified_base
<222> LOCATION: (151)
<223> OTHER INFORMATION: Where n is a, c, g or t
<221> NAME/KEY: modified_base
<222> LOCATION: (203)
<223> OTHER INFORMATION: Where n is a, c, g or t
<221> NAME/KEY: modified_base
<222> LOCATION: (226)
<223> OTHER INFORMATION: Where n is a, c, g or t
<221> NAME/KEY: modified_base
<222> LOCATION: (228)
<223> OTHER INFORMATION: Where n is a, c, g or t
<221> NAME/KEY: modified_base
<222> LOCATION: (233)
<223> OTHER INFORMATION: Where n is a, c, g or t
<221> NAME/KEY: modified_base
<222> LOCATION: (252)
<223> OTHER INFORMATION: Where n is a, c, g or t
<221> NAME/KEY: modified_base
<222> LOCATION: (264)
<223> OTHER INFORMATION: Where n is a, c, g or t
<221> NAME/KEY: modified_base
<222> LOCATION: (279)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (308)
<223> OTHER INFORMATION: Where n is a, c, g or t
<221> NAME/KEY: modified_base
<222> LOCATION: (320)
<223> OTHER INFORMATION: Where n is a, c, g or t
<221> NAME/KEY: modified_base
<222> LOCATION: (340)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (400)

```
<223> OTHER INFORMATION: Where n is a, c, g or t
<221> NAME/KEY: modified_base
<222> LOCATION: (407)
<223> OTHER INFORMATION: Where n is a, c, g or t
<221> NAME/KEY: modified_base
<222> LOCATION: (4029)
<223> OTHER INFORMATION: Where n is a, c, g or t
<221> NAME/KEY: modified_base
<222> LOCATION: (437)
<223> OTHER INFORMATION: Where n is a, c, g or t
<221> NAME/KEY: modified_base
<222> LOCATION: (440)
<223> OTHER INFORMATION: Where n is a, c, g or t
<221> NAME/KEY: modified_base
<222> LOCATION: (445)
<223> OTHER INFORMATION: Where n is a, c, g or t
<221> NAME/KEY: modified_base
<222> LOCATION: (448)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (559)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (586)
<223> OTHER INFORMATION: Where n is a, c, g or t
<221> NAME/KEY: modified_base
<222> LOCATION: (589)
<223> OTHER INFORMATION: Where n is a, c, g or t
<221> NAME/KEY: modified_base
<222> LOCATION: (593)
<223> OTHER INFORMATION: Where n is a, c, g or t
<221> NAME/KEY: modified_base
<222> LOCATION: (596)
<223> OTHER INFORMATION: Where n is a, c, g or t
<221> NAME/KEY: modified_base
<222> LOCATION: (603)
<223> OTHER INFORMATION: Where n is a, c, g or t
<221> NAME/KEY: modified_base
<222> LOCATION: (605)
<223> OTHER INFORMATION: Where n is a, c, g or t
<221> NAME/KEY: modified_base
<222> LOCATION: (606)
<223> OTHER INFORMATION: Where n is a, c, g or t
<221> NAME/KEY: modified_base
<222> LOCATION: (609)
<223> OTHER INFORMATION: Where n is a, c, g or t
<221> NAME/KEY: modified_base
<222> LOCATION: (626)
<223> OTHER INFORMATION: Where n is a, c, g or t
<221> NAME/KEY: modified_base
<222> LOCATION: (639)
<223> OTHER INFORMATION: Where n is a, c, g or t
<221> NAME/KEY: modified_base
<222> LOCATION: (655)
<223> OTHER INFORMATION: Where n is a, c, g or t
<221> NAME/KEY: modified_base
<222> LOCATION: (674)
<223> OTHER INFORMATION: Where n is a, c, g or t
<221> NAME/KEY: modified_base
<222> LOCATION: (682)
<223> OTHER INFORMATION: Where n is a, c, g or t

<400> SEQUENCE: 38
canaaaaaaa aaaacatggc cgaaaccagn aagctgcgcg atgcgccac  ggccctctt      60 ctcccggcct gtgtccggaa ggtttccctc cgaggcgccc cggctcccgc aagcggagga   120
gagggcggga cntgccgggg ccggagctca naggccctgg ggccgctctg ctctcccgcc   180
atcgcaaggg cggcgctaac ctnaggcctc cccgcaaagg tcccnangc ggnggcggcg    240 gggggctgtg anaaccgcaa aaanaacgct gggcgcgcng cgaaccgtc caccccgcg    300
```

-continued

```
aaggananac ttccacagan gcagcgtttc cacagcccan agccacnttt ctagggtgat      360
gcaccccagt aagttcctgn cggggaagct caccgctgtc aaaaaanctc ttcgctccac      420
cggcgcacna agggganган ggcangangc tgccgcccgc acaggtcatc tgatcacgtc      480
gcccgcccta ntctgctttt gtgaatctcc actttgttca accccacccg ccgttctctc      540
ctccttgcgc cttcctctna ccttaanaac cagcttcctc tacccnatng tanttnctct      600
gcncnngtng aaattaattc ggtccnccgg aacctcttnc ctgtggcaac tgctnaaaga      660
aactgctgtt ctgnttactg cngtccc                                          687
```

```
<210> SEQ ID NO 39
<211> LENGTH: 695
<212> TYPE: DNA
<213> ORGANISM: Homo sapiens
<220> FEATURE:
<221> NAME/KEY: modified_base
<222> LOCATION: (300)
<223> OTHER INFORMATION: Where n is a, c, g or t
<221> NAME/KEY: modified_base
<222> LOCATION: (401)
<223> OTHER INFORMATION: Where n is a, c, g or t
<221> NAME/KEY: modified_base
<222> LOCATION: (423)
<223> OTHER INFORMATION: Where n is a, c, g or t
<221> NAME/KEY: modified_base
<222> LOCATION: (429)
<223> OTHER INFORMATION: Where n is a, c, g or t
<221> NAME/KEY: modified_base
<222> LOCATION: (431)
<223> OTHER INFORMATION: Where n is a, c, g or t
<221> NAME/KEY: modified_base
<222> LOCATION: (437)
<223> OTHER INFORMATION: Where n is a, c, g or t
<221> NAME/KEY: modified_base
<222> LOCATION: (443)
<223> OTHER INFORMATION: Where n is a, c, g or t
<221> NAME/KEY: modified_base
<222> LOCATION: (448)
<223> OTHER INFORMATION: Where n is a, c, g or t
<221> NAME/KEY: modified_base
<222> LOCATION: (454)
<223> OTHER INFORMATION: Where n is a, c, g or t
<221> NAME/KEY: modified_base
<222> LOCATION: (466)
<223> OTHER INFORMATION: Where n is a, c, g or t
<221> NAME/KEY: modified_base
<222> LOCATION: (492)
<223> OTHER INFORMATION: Where n is a, c, g or t
<221> NAME/KEY: modified_base
<222> LOCATION: (515)
<223> OTHER INFORMATION: Where n is a, c, g or t
<221> NAME/KEY: modified_base
<222> LOCATION: (523)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (536)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (541)
<223> OTHER INFORMATION: Where n is a, c, g or t
<221> NAME/KEY: modified_base
<222> LOCATION: (552)
<223> OTHER INFORMATION: Where n is a, c, g or t
<221> NAME/KEY: modified_base
<222> LOCATION: (561)
<223> OTHER INFORMATION: Where n is a, c, g or t
<221> NAME/KEY: modified_base
```

<222> LOCATION: (566)
<223> OTHER INFORMATION: Where n is a, c, g or t
<221> NAME/KEY: modified_base
<222> LOCATION: (581)
<223> OTHER INFORMATION: Where n is a, c, g or t
<221> NAME/KEY: modified_base
<222> LOCATION: (583)
<223> OTHER INFORMATION: Where n is a, c, g or t
<221> NAME/KEY: modified_base
<222> LOCATION: (619)
<223> OTHER INFORMATION: Where n is a, c, g or t
<221> NAME/KEY: modified_base
<222> LOCATION: (635)
<223> OTHER INFORMATION: Where n is a, c, g or t
<221> NAME/KEY: modified_base
<222> LOCATION: (636)
<223> OTHER INFORMATION: Where n is a, c, g or t
<221> NAME/KEY: modified_base
<222> LOCATION: (641)
<223> OTHER INFORMATION: Where n is a, c, g or t
<221> NAME/KEY: modified_base
<222> LOCATION: (649)
<223> OTHER INFORMATION: Where n is a, c, g or t
<221> NAME/KEY: modified_base
<222> LOCATION: (661)
<223> OTHER INFORMATION: Where n is a, c, g or t
<221> NAME/KEY: modified_base
<222> LOCATION: (694)
<223> OTHER INFORMATION: Where n is a, c, g or t

<400> SEQUENCE: 39

```
actagtctgg cctacaatag tgtgattcat gtaggacttc tttcatcaat tcaaaacccc      60
tagaaaaacg tatacagatt atataagtag ggataagatt tctaacattt ctgggctctc     120
tgacccctgc gctagactgt ggaaagggag tattattata gtatacaaca ctgctgttgc     180
cttattagtt ataacatgat aggtgctgaa ttgtgattca caatttaaaa acactgtaat     240
ccaaactttt ttttttaact gtagatcatg catgtgaatg ttaatgttaa tttgttcaan     300
gttgttatgg gtagaaaaaa ccacatgcct taaaatttta aaaagcaggg cccaaactta     360
ttagtttaaa attaggggta tgtttccagt ttgttattaa ntggttatag ctctgtttag     420
aanaaatcna ngaacangat ttngaaantt aagntgacat tatttnccag tgacttgtta     480
atttgaaatc anacacggca ccttccgttt tggtnctatt ggnntttgaa tccaancngg     540
ntccaaatct tnttggaaac ngtccnttta acttttttac nanatcttat tttttttattt    600 tggaatggcc ctatttaang ttaaaagggg ggggnnccac naccattcnt gaataaaact     660
naatatatat ccttggtccc ccaaaattta aggng                                695
```

<210> SEQ ID NO 40
<211> LENGTH: 674
<212> TYPE: DNA
<213> ORGANISM: Homo sapiens
<220> FEATURE:
<221> NAME/KEY: modified_base
<222> LOCATION: (403)
<223> OTHER INFORMATION: Where n is a, c, g or t
<221> NAME/KEY: modified_base
<222> LOCATION: (428)
<223> OTHER INFORMATION: Where n is a, c, g or t
<221> NAME/KEY: modified_base
<222> LOCATION: (432)
<223> OTHER INFORMATION: Where n is a, c, g or t
<221> NAME/KEY: modified_base
<222> LOCATION: (507)
<223> OTHER INFORMATION: Where n is a, c, g or t
<221> NAME/KEY: modified_base
<222> LOCATION: (530)
<223> OTHER INFORMATION: Where n is a, c, g or t
<221> NAME/KEY: modified_base
<222> LOCATION: (543)

<223> OTHER INFORMATION: Where n is a, c, g or t
<221> NAME/KEY: modified_base
<222> LOCATION: (580)
<223> OTHER INFORMATION: Where n is a, c, g or t
<221> NAME/KEY: modified_base
<222> LOCATION: (583)
<223> OTHER INFORMATION: Where n is a, c, g or t
<221> NAME/KEY: modified_base
<222> LOCATION: (591)
<223> OTHER INFORMATION: Where n is a, c, g or t
<221> NAME/KEY: modified_base
<222> LOCATION: (604)
<223> OTHER INFORMATION: Where n is a, c, g or t
<221> NAME/KEY: modified_base
<222> LOCATION: (608)
<223> OTHER INFORMATION: Where n is a, c, g or t
<221> NAME/KEY: modified_base
<222> LOCATION: (621)
<223> OTHER INFORMATION: Where n is a, c, g or t
<221> NAME/KEY: modified_base
<222> LOCATION: (624)
<223> OTHER INFORMATION: Where n is a, c, g or t
<221> NAME/KEY: modified_base
<222> LOCATION: (626)
<223> OTHER INFORMATION: Where n is a, c, g or t
<221> NAME/KEY: modified_base
<222> LOCATION: (639)
<223> OTHER INFORMATION: Where n is a, c, g or t
<221> NAME/KEY: modified_base
<222> LOCATION: (672)
<223> OTHER INFORMATION: Where n is a, c, g or t

<400> SEQUENCE: 40

```
actagtagtc agttgggagt ggttgctata ccttgacttc atttatatga atttccactt      60
tattaaataa tagaaaagaa aatcccggtg cttgcagtag agttataggt cattctatgc     120
ttacagaaaa tatagccatg attgaaatca aatagtaaag gctgttctgg cttttatct     180
tcttagctca tcttaaataa gtagtacact tgggatgcag tgcgtctgaa gtgctaatca    240
gttgtaacaa tagcacaaat cgaacttagg atgtgtttct tctcttctgt gtttcgattt    300
tgatcaattc tttaattttg ggaacctata atacagtttt cctattcttg gagataaaaa    360
ttaaatggat cactgatatt taagtcattc tgcttctcat ctnaatattc catattctgt    420
attagganaa antacctccc agcacagccc cctctcaaac cccacccaaa accaagcatt    480
tggaatgagt ctccttatt tccgaantgt ggatggtata acccatatcn ctccaatttc    540
tgnttgggtt gggtattaat ttgaactgtg catgaaaagn ggnaatcttt nctttgggtc    600
aaantttncc ggttaatttg nctngncaaa tccaatttnc tttaagggtg tctttataaa    660
atttgctatt cngg                                                      674
```

<210> SEQ ID NO 41
<211> LENGTH: 657
<212> TYPE: DNA
<213> ORGANISM: Homo sapiens
<220> FEATURE:
<221> NAME/KEY: modified_base
<222> LOCATION: (243)
<223> OTHER INFORMATION: Where n is a, c, g or t
<221> NAME/KEY: modified_base
<222> LOCATION: (247)
<223> OTHER INFORMATION: Where n is a, c, g or t
<221> NAME/KEY: modified_base
<222> LOCATION: (251)
<223> OTHER INFORMATION: Where n is a, c, g or t
<221> NAME/KEY: modified_base
<222> LOCATION: (261)
<223> OTHER INFORMATION: Where n is a, c, g or t
<221> NAME/KEY: modified_base
<222> LOCATION: (267)
<223> OTHER INFORMATION: Where n is a, c, g or t

```
<221> NAME/KEY: modified_base
<222> LOCATION: (272)
<223> OTHER INFORMATION: Where n is a, c, g or t
<221> NAME/KEY: modified_base
<222> LOCATION: (298)
<223> OTHER INFORMATION: Where n is a, c, g or t
<221> NAME/KEY: modified_base
<222> LOCATION: (312)
<223> OTHER INFORMATION: Where n is a, c, g or t
<221> NAME/KEY: modified_base
<222> LOCATION: (315)
<223> OTHER INFORMATION: Where n is a, c, g or t
<221> NAME/KEY: modified_base
<222> LOCATION: (421)
<223> OTHER INFORMATION: Where n is a, c, g or t
<221> NAME/KEY: modified_base
<222> LOCATION: (432)
<223> OTHER INFORMATION: Where n is a, c, g or t
<221> NAME/KEY: modified_base
<222> LOCATION: (434)
<223> OTHER INFORMATION: Where n is a, c, g or t
<221> NAME/KEY: modified_base
<222> LOCATION: (501)
<223> OTHER INFORMATION: Where n is a, c, g or t
<221> NAME/KEY: modified_base
<222> LOCATION: (524)
<223> OTHER INFORMATION: Where n is a, c, g or t
<221> NAME/KEY: modified_base
<222> LOCATION: (569)
<223> OTHER INFORMATION: Where n is a, c, g or t
<221> NAME/KEY: modified_base
<222> LOCATION: (594)
<223> OTHER INFORMATION: Where n is a, c, g or t
<221> NAME/KEY: modified_base
<222> LOCATION: (607)
<223> OTHER INFORMATION: Where n is a, c, g or t
<221> NAME/KEY: modified_base
<222> LOCATION: (650)
<223> OTHER INFORMATION: Where n is a, c, g or t

<400> SEQUENCE: 41
gaaacatgca agtaccacac actgtttgaa ttttgcacaa aaagtgactg tagggatcag      60
gtgatagccc cggaatgtac agtgtcttgg tgcaccaaga tgccttctaa aggctgacat     120
accttgggac cctaatgggg cagagagtat agccctagcc cagtggtgac atgaccactc     180
cctttgggag gctgaagtta aagggaatgg tatgtgtttt ctcatggaag cagcacatga     240
atnggtnaca ngatgttaaa ntaaggntct antttgggtg tcttgtcatt tgaaaaantg     300
acacactcct ancanctggt aaagggggtgc tggaagccat ggaagaactc taaaaacatt   360
agcatgggct gatctgatta cttcctggca tcccgctcac ttttatggga agtcttatta    420
naaggatggg ananttttcc atatccttgc tgttggaact ctggaacact ctctaaattt    480
ccctctatta aaaatcactg nccttactac acttcctcct tganggaata gaaatggacc    540
tttctctgac ttagttcttg gcatgggganc cagcccaaat taaaatctga cttntccggt   600
ttctccngaa ctcacctact tgaattggta aaacctcctt tggaattagn aaaaacc       657

<210> SEQ ID NO 42
<211> LENGTH: 389
<212> TYPE: DNA
<213> ORGANISM: Homo sapiens
<220> FEATURE:
<221> NAME/KEY: modified_base
<222> LOCATION: (179)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (320)
<223> OTHER INFORMATION: Where n is a, c, g or t
```

<400> SEQUENCE: 42

```
actagtgctg aggaatgtaa acaagtttgc tgggccttgc gagacttcac caggttgttt      60
cgatagctca cactcctgca ctgtgcctgt cacccaggaa tgtcttttt  aattagaaga    120
caggaagaaa acaaaaacca gactgtgtcc cacaatcaga acctccgtt  gtggcagang    180
ggccttcacc gccaccaggg tgtcccgcca gacagggaga gactccagcc ttctgaggcc    240
atcctgaaga attcctgttt gggggttgtg aaggaaaatc acccggattt aaaaagatgc    300
tgttgcctgc ccgcgtngtn gggaagggac tggtttcctg gtgaatttct taaaagaaaa    360
atattttaag ttaagaaaaa aaaaaaaaa                                      389
```

<210> SEQ ID NO 43
<211> LENGTH: 279
<212> TYPE: DNA
<213> ORGANISM: Homo sapiens

<400> SEQUENCE: 43

```
actagtgaca agctcctggt cttgagatgt cttctcgtta aggagatggg cctttggag      60
gtaaaggata aatgaatga  gttctgtcat gattcactat tctagaactt gcatgacctt    120
tactgtgtta gctcttgaa  tgttcttgaa attttagact ttctttgtaa acaaataata    180
tgtccttatc attgtataaa agctgttatg tgcaacagtg tggagatcct tgtctgattt    240
aataaaatac ttaaacactg aaaaaaaaaa aaaaaaaa                            279
```

<210> SEQ ID NO 44
<211> LENGTH: 449
<212> TYPE: DNA
<213> ORGANISM: Homo sapiens
<220> FEATURE:
<221> NAME/KEY: modified_base
<222> LOCATION: (245)
<223> OTHER INFORMATION: Where n is a, c, g or t
<221> NAME/KEY: modified_base
<222> LOCATION: (256)
<223> OTHER INFORMATION: Where n is a, c, g or t
<221> NAME/KEY: modified_base
<222> LOCATION: (264)
<223> OTHER INFORMATION: Where n is a, c, g or t
<221> NAME/KEY: modified_base
<222> LOCATION: (266)
<223> OTHER INFORMATION: Where n is a, c, g or t
<221> NAME/KEY: modified_base
<222> LOCATION: (273)
<223> OTHER INFORMATION: Where n is a, c, g or t
<221> NAME/KEY: modified_base
<222> LOCATION: (281)
<223> OTHER INFORMATION: Where n is a, c, g or t
<221> NAME/KEY: modified_base
<222> LOCATION: (323)
<223> OTHER INFORMATION: Where n is a, c, g or t
<221> NAME/KEY: modified_base
<222> LOCATION: (325)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (393)
<223> OTHER INFORMATION: Where n is a, c, g or t

<400> SEQUENCE: 44

```
actagtagca tcttttctac aacgttaaaa ttgcagaagt agcttatcat taaaaaacaa      60
caacaacaac aataacaata aatcctaagt gtaaatcagt tattctaccc cctaccaagg    120
atatcagcct gttttttccc ttttttctcc tgggaataat tgtgggcttc ttcccaaatt    180
```

```
tctacagcct ctttcctctt ctcatgcttg agcttccctg tttgcacgca tgcgttgtgc    240
aagantgggc tgtttngctt ggantncggt ccnagtggaa ncatgctttc ccttgttact    300
gttggaagaa actcaaacct tcnaccccta ggtgttncca ttttgtcaag tcatcactgt    360 attttgtac tggcattaac aaaaaaagaa atnaaatatt gttccattaa actttaataa     420
aactttaaaa gggaaaaaaa aaaaaaaaa                                      449
```

<210> SEQ ID NO 45
<211> LENGTH: 559
<212> TYPE: DNA
<213> ORGANISM: Homo sapiens
<220> FEATURE:
<221> NAME/KEY: modified_base
<222> LOCATION: (263)
<223> OTHER INFORMATION: Where n is a, c, g or t

<400> SEQUENCE: 45

```
actagtgtgg gggaatcacg gacacttaaa gtcaatctgc gaaataattc ttttattaca    60
cactcactga agtttttgag tcccagagag ccattctatg tcaaacattc caagtactct   120
ttgagagccc agcattacat caacatgccc gtgcagttca aaccgaagtc cgcaggcaaa   180
tttgaagctt tgcttgtcat tcaaacagat gaaggcaaga gtattgctat tcgactaatt   240
ggtgaagctc ttggaaaaaa ttnactagaa tacttttgt gttaagttaa ttacataagt    300
tgtattttgt taactttatc tttctacact acaattatgc ttttgtatat atattttgta   360
tgatggatat ctataattgt agattttgtt tttacaagct aatactgaag actcgactga   420
aatattatgt atctagccca tagtattgta cttaactttt acagggtgaa aaaaaaattc   480
tgtgtttgca ttgattatga tattctgaat aaatatggga atatatttta atgtgggtaa   540
aaaaaaaaaa aaaaaggaa                                                559
```

<210> SEQ ID NO 46
<211> LENGTH: 731
<212> TYPE: DNA
<213> ORGANISM: Homo sapiens
<220> FEATURE:
<221> NAME/KEY: modified_base
<222> LOCATION: (270)
<223> OTHER INFORMATION: Where n is a, c, g or t
<221> NAME/KEY: modified_base
<222> LOCATION: (467)
<223> OTHER INFORMATION: Where n is a, c, g or t
<221> NAME/KEY: modified_base
<222> LOCATION: (477)
<223> OTHER INFORMATION: Where n is a, c, g or t
<221> NAME/KEY: modified_base
<222> LOCATION: (502)
<223> OTHER INFORMATION: Where n is a, c, g or t
<221> NAME/KEY: modified_base
<222> LOCATION: (635)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (671)
<223> OTHER INFORMATION: Where n is a, c, g or t
<221> NAME/KEY: modified_base
<222> LOCATION: (688)
<223> OTHER INFORMATION: Where n is a, c, g or t
<221> NAME/KEY: modified_base
<222> LOCATION: (695)
<223> OTHER INFORMATION: Where n is a, c, g or t
<221> NAME/KEY: modified_base
<222> LOCATION: (697)
<223> OTHER INFORMATION: Where n is a, c, g or t
<221> NAME/KEY: modified_base
<222> LOCATION: (725)
<223> OTHER INFORMATION: Where n is a, c, g or t

<400> SEQUENCE: 46

| | | | | | |
|---|---|---|---|---|---|
| actagttcta | gtaccatggc | tgtcatagat | gcaaccatta | tattccattt | agtttcttcc | 60 |
| tcaggttccc | taacaattgt | ttgaaactga | atatatatgt | ttatgtatgt | gtgtgtgttc | 120 |
| actgtcatgt | atatggtgta | tatgggatgt | gtgcagtttt | cagttatata | tatattcata | 180 |
| tatacatatg | catatatatg | tataaatatac | atatatacat | gcatacactt | gtataatata | 240 |
| catatatata | cacatatatg | cacacatatn | atcactgagt | tccaaagtga | gtctttattt | 300 |
| ggggcaattg | tattctctcc | ctctgtctgc | tcactgggcc | tttgcaagac | atagcaattg | 360 |
| cttgatttcc | tttggataag | agtcttatct | tcggcactct | tgactctagc | cttaacttta | 420 |
| gatttctatt | ccagaatacc | tctcatatct | atcttaaaac | ctaaganggg | taaagangtc | 480 |
| ataagattgt | agtatgaaag | antttgctta | gttaaattat | atctcaggaa | actcattcat | 540 |
| ctacaaatta | aattgtaaaa | tgatggtttg | ttgtatctga | aaaaatgttt | agaacaagaa | 600 |
| atgtaactgg | gtacctgtta | tatcaaagaa | cctcnattta | ttaagtctcc | tcatagccan | 660 |
| atccttatat | ngccctctct | gacctganttt | aatananact | tgaataatga | atagttaatt | 720 |
| taggnttggg | c | | | | | 731 |

<210> SEQ ID NO 47
<211> LENGTH: 640
<212> TYPE: DNA
<213> ORGANISM: Homo sapiens
<220> FEATURE:
<221> NAME/KEY: modified_base
<222> LOCATION: (5)
<223> OTHER INFORMATION: Where n is a, c, g or t
<221> NAME/KEY: modified_base
<222> LOCATION: (28)
<223> OTHER INFORMATION: Where n is a, c, g or t
<221> NAME/KEY: modified_base
<222> LOCATION: (106)
<223> OTHER INFORMATION: Where n is a, c, g or t
<221> NAME/KEY: modified_base
<222> LOCATION: (153)
<223> OTHER INFORMATION: Where n is a, c, g or t
<221> NAME/KEY: modified_base
<222> LOCATION: (158)
<223> OTHER INFORMATION: Where n is a, c, g or t
<221> NAME/KEY: modified_base
<222> LOCATION: (173)
<223> OTHER INFORMATION: Where n is a, c, g or t
<221> NAME/KEY: modified_base
<222> LOCATION: (176)
<223> OTHER INFORMATION: Where n is a, c, g or t
<221> NAME/KEY: modified_base
<222> LOCATION: (182)
<223> OTHER INFORMATION: Where n is a, c, g or t
<221> NAME/KEY: modified_base
<222> LOCATION: (189)
<223> OTHER INFORMATION: Where n is a, c, g or t
<221> NAME/KEY: modified_base
<222> LOCATION: (205)
<223> OTHER INFORMATION: Where n is a, c, g or t
<221> NAME/KEY: modified_base
<222> LOCATION: (210)
<223> OTHER INFORMATION: Where n is a, c, g or t
<221> NAME/KEY: modified_base
<222> LOCATION: (214)
<223> OTHER INFORMATION: Where n is a, c, g or t
<221> NAME/KEY: modified_base
<222> LOCATION: (225)
<223> OTHER INFORMATION: Where n is a, c, g or t
<221> NAME/KEY: modified_base
<222> LOCATION: (226)

-continued

```
<223> OTHER INFORMATION: Where n is a, c, g or t
<221> NAME/KEY: modified_base
<222> LOCATION: (229)
<223> OTHER INFORMATION: Where n is a, c, g or t
<221> NAME/KEY: modified_base
<222> LOCATION: (237)
<223> OTHER INFORMATION: Where n is a, c, g or t
<221> NAME/KEY: modified_base
<222> LOCATION: (260)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (269)
<223> OTHER INFORMATION: Where n is a, c, g or t
<221> NAME/KEY: modified_base
<222> LOCATION: (277)
<223> OTHER INFORMATION: Where n is a, c, g or t
<221> NAME/KEY: modified_base
<222> LOCATION: (281)
<223> OTHER INFORMATION: Where n is a, c, g or t
<221> NAME/KEY: modified_base
<222> LOCATION: (282)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (338)
<223> OTHER INFORMATION: Where n is a, c, g or t
<221> NAME/KEY: modified_base
<222> LOCATION: (354)
<223> OTHER INFORMATION: Where n is a, c, g or t
<221> NAME/KEY: modified_base
<222> LOCATION: (365)
<223> OTHER INFORMATION: Where n is a, c, g or t
<221> NAME/KEY: modified_base
<222> LOCATION: (428)
<223> OTHER INFORMATION: Where n is a, c, g or t
<221> NAME/KEY: modified_base
<222> LOCATION: (441)
<223> OTHER INFORMATION: Where n is a, c, g or t
<221> NAME/KEY: modified_base
<222> LOCATION: (443)
<223> OTHER INFORMATION: Where n is a, c, g or t
<221> NAME/KEY: modified_base
<222> LOCATION: (456)
<223> OTHER INFORMATION: Where n is a, c, g or t
<221> NAME/KEY: modified_base
<222> LOCATION: (467)
<223> OTHER INFORMATION: Where n is a, c, g or t
<221> NAME/KEY: modified_base
<222> LOCATION: (476)
<223> OTHER INFORMATION: Where n is a, c, g or t
<221> NAME/KEY: modified_base
<222> LOCATION: (484)
<223> OTHER INFORMATION: Where n is a, c, g or t
<221> NAME/KEY: modified_base
<222> LOCATION: (503)
<223> OTHER INFORMATION: Where n is a, c, g or t
<221> NAME/KEY: modified_base
<222> LOCATION: (508)
<223> OTHER INFORMATION: Where n is a, c, g or t
<221> NAME/KEY: modified_base
<222> LOCATION: (554)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (575)
<223> OTHER INFORMATION: Where n is a, c, g or t
<221> NAME/KEY: modified_base
<222> LOCATION: (579)
<223> OTHER INFORMATION: Where n is a, c, g or t
```

<221> NAME/KEY: modified_base
<222> LOCATION: (588)
<223> OTHER INFORMATION: Where n is a, c, g or t
<221> NAME/KEY: modified_base
<222> LOCATION: (601)
<223> OTHER INFORMATION: Where n is a, c, g or t
<221> NAME/KEY: modified_base
<222> LOCATION: (606)
<223> OTHER INFORMATION: Where n is a, c, g or t
<221> NAME/KEY: modified_base
<222> LOCATION: (609)
<223> OTHER INFORMATION: Where n is a, c, g or t
<221> NAME/KEY: modified_base
<222> LOCATION: (611)
<223> OTHER INFORMATION: Where n is a, c, g or t
<221> NAME/KEY: modified_base
<222> LOCATION: (621)
<223> OTHER INFORMATION: Where n is a, c, g or t
<221> NAME/KEY: modified_base
<222> LOCATION: (636)
<223> OTHER INFORMATION: Where n is a, c, g or t

<400> SEQUENCE: 47

```
tgcgngccgg tttggcccct ctttgtanga cactttcatc cgccctgaaa tcttcccgat    60
cgttaataac tcctcaggtc cctgcctgca cagggttttt tcttantttg ttgcctaaca   120
gtacaccaaa tgtgacatcc tttcaccaat atngattnct tcataccaca tcntcnatgg   180
anacgactnc aacaatttt tgatnacccn aaanactggg ggctnnaana agtacantct   240
ggagcagcat ggacctgtcn gcnactaang gaacaanagt nntgaacatt tacacaacct   300
ttggtatgtc ttactgaaag anagaaacat gcttctnncc ctagaccacg aggncaaccg   360
caganattgc caatgccaag tccgagcggt tagatcaggt aatacattcc atggatgcat   420
tacatacntt gtccccgaaa nanaagatgc cctaanggct tcttcanact ggtccngaaa   480
acanctacac ctggtgcttg ganaacanac tctttggaag atcatctggc acaagttccc   540
cccagtgggt tttnccttgg cacctancct accanatcna ttcggaancc attctttgcc   600
ntggcnttnt nttgggacca ntcttctcac aactgnaccc                          640
```

<210> SEQ ID NO 48
<211> LENGTH: 257
<212> TYPE: DNA
<213> ORGANISM: Homo sapiens

<400> SEQUENCE: 48

```
actagtatat gaaaatgtaa atatcacttg tgtactcaaa caaaagttgg tcttaagctt    60
ccaccttgag cagccttgga aacctaacct gcctctttta gcataatcac attttctaaa   120
tgattttctt tgttcctgaa aaagtgattt gtattagttt tacatttgtt ttttggaaga   180
ttatatttgt atatgtatca tcataaaata tttaaataaa aagtatcttt agagtgaaaa   240
aaaaaaaaaa aaaaaaa                                                  257
```

<210> SEQ ID NO 49
<211> LENGTH: 652
<212> TYPE: DNA
<213> ORGANISM: Homo sapiens
<220> FEATURE:
<221> NAME/KEY: modified_base
<222> LOCATION: (410)
<223> OTHER INFORMATION: Where n is a, c, g or t
<221> NAME/KEY: modified_base
<222> LOCATION: (428)
<223> OTHER INFORMATION: Where n is a, c, g or t
<221> NAME/KEY: modified_base
<222> LOCATION: (496)
<223> OTHER INFORMATION: Where n is a, c, g or t
<221> NAME/KEY: modified_base
<222> LOCATION: (571)
<223> OTHER INFORMATION: Where n is a, c, g or t
<221> NAME/KEY: modified_base
<222> LOCATION: (647)
<223> OTHER INFORMATION: Where n is a, c, g or t

<400> SEQUENCE: 49

```
actagttcag atgagtggct gctgaagggg cccccttgtc attttcatta taacccaatt     60
tccacttatt tgaactctta agtcataaat gtaatgac ttatgaatta gcacagttaa      120
gttgacacta gaaactgccc atttctgtat tacactatca aataggaaac attggaaaga    180
tggggaaaaa aatcttattt taaaatggct tagaaagttt tcagattact ttgaaaattc    240
taaacttctt tctgtttcca aaacttgaaa atatgtagat ggactcatgc attaagactg    300
ttttcaaagc tttcctcaca tttttaaagt gtgattttcc ttttaatata catatttatt    360
ttctttaaag cagctatatc ccaacccatg actttggaga tataccctatn aaaccaatat   420
aacagcangg ttattgaagc agctttctca aatgttgctt cagatgtgca agttgcaaat    480
tttattgtat ttgtanaata caattttgt tttaaactgt atttcaatct atttctccaa     540
gatgcttttc atatagagtg aaatatccca ngataactgc ttctgtgtcg tcgcatttga    600
cgcataactg cacaaatgaa cagtgtatac ctcttggttg tgcattnacc cc            652
```

<210> SEQ ID NO 50
<211> LENGTH: 650
<212> TYPE: DNA
<213> ORGANISM: Homo sapiens
<220> FEATURE:
<221> NAME/KEY: modified_base
<222> LOCATION: (237)
<223> OTHER INFORMATION: Where n is a, c, g or t
<221> NAME/KEY: modified_base
<222> LOCATION: (270)
<223> OTHER INFORMATION: Where n is a, c, g or t
<221> NAME/KEY: modified_base
<222> LOCATION: (311)
<223> OTHER INFORMATION: Where n is a, c, g or t
<221> NAME/KEY: modified_base
<222> LOCATION: (443)
<223> OTHER INFORMATION: Where n is a, c, g or t
<221> NAME/KEY: modified_base
<222> LOCATION: (454)
<223> OTHER INFORMATION: Where n is a, c, g or t
<221> NAME/KEY: modified_base
<222> LOCATION: (488)
<223> OTHER INFORMATION: Where n is a, c, g or t
<221> NAME/KEY: modified_base
<222> LOCATION: (520)
<223> OTHER INFORMATION: Where n is a, c, g or t
<221> NAME/KEY: modified_base
<222> LOCATION: (535)
<223> OTHER INFORMATION: Where n is a, c, g or t
<221> NAME/KEY: modified_base
<222> LOCATION: (539)
<223> OTHER INFORMATION: Where n is a, c, g or t
<221> NAME/KEY: modified_base
<222> LOCATION: (556)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (594)
<223> OTHER INFORMATION: Where n is a, c, g or t
<221> NAME/KEY: modified_base
<222> LOCATION: (603)
<223> OTHER INFORMATION: Where n is a, c, g or t
<221> NAME/KEY: modified_base
<222> LOCATION: (634)
<223> OTHER INFORMATION: Where n is a, c, g or t

<400> SEQUENCE: 50

```
ttgcgctttg attttttag ggcttgtgcc ctgtttcact tatagggtct agaatgcttg      60
tgttgagtaa aaaggagatg cccaatattc aaagctgcta aatgttctct ttgccataaa    120
gactccgtgt aactgtgtga acacttggga tttttctcct ctgtcccgag gtcgtcgtct    180
gctttctttt ttgggttctt tctagaagat tgagaaatgc atatgacagg ctgagancac    240
ctccccaaac acacaagctc tcagcccacan gcagcttctc cacagcccca gcttcgcaca    300
ggctcctgga nggctgcctg ggggaggcag acatgggagt gccaaggtgg ccagatggtt    360
ccaggactac aatgtcttta tttttaactg tttgccactg ctgccctcac ccctgcccgg    420
ctctggagta ccgtctgccc canacaagtg ggantgaaat gggggtgggg gggaacactg    480
attcccantt aggggtgcc taactgaaca gtagggatan aagtgtgaa cctgngaant     540
gcttttataa attatnttcc ttgttanatt tattttttaa tttaatctct gttnaactgc    600
ccngggaaaa gggaaaaaa aaaaaaaaat tctntttaaa cacatgaaca              650
```

<210> SEQ ID NO 51
<211> LENGTH: 545
<212> TYPE: DNA
<213> ORGANISM: Homo sapiens
<220> FEATURE:
<221> NAME/KEY: modified_base
<222> LOCATION: (66)
<223> OTHER INFORMATION: Where n is a, c, g or t
<221> NAME/KEY: modified_base
<222> LOCATION: (159)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (205)
<223> OTHER INFORMATION: Where n is a, c, g or t
<221> NAME/KEY: modified_base
<222> LOCATION: (214)
<223> OTHER INFORMATION: Where n is a, c, g or t
<221> NAME/KEY: modified_base
<222> LOCATION: (243)
<223> OTHER INFORMATION: Where n is a, c, g or t
<221> NAME/KEY: modified_base
<222> LOCATION: (278)
<223> OTHER INFORMATION: Where n is a, c, g or t
<221> NAME/KEY: modified_base
<222> LOCATION: (298)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (366)
<223> OTHER INFORMATION: Where n is a, c, g or t
<221> NAME/KEY: modified_base
<222> LOCATION: (375)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (405)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (477)
<223> OTHER INFORMATION: Where n is a, c, g or t -continued
<221> NAME/KEY: modified_base
<222> LOCATION: (492)
<223> OTHER INFORMATION: Where n is a, c, g or t
<221> NAME/KEY: modified_base
<222> LOCATION: (495)
<223> OTHER INFORMATION: Where n is a, c, g or t
<221> NAME/KEY: modified_base
<222> LOCATION: (503)
<223> OTHER INFORMATION: Where n is a, c, g or t
<221> NAME/KEY: modified_base
<222> LOCATION: (507)
<223> OTHER INFORMATION: Where n is a, c, g or t
<221> NAME/KEY: modified_base
<222> LOCATION: (508)
<223> OTHER INFORMATION: Where n is a, c, g or t
<221> NAME/KEY: modified_base
<222> LOCATION: (521)
<223> OTHER INFORMATION: Where n is a, c, g or t
<221> NAME/KEY: modified_base
<222> LOCATION: (537)
<223> OTHER INFORMATION: Where n is a, c, g or t

<400> SEQUENCE: 51

```
tggcgtgcaa ccagggtagc tgaagtttgg gtctgggact ggagattggc cattaggcct      60
cctganattc cagctcccct tccaccaagcc cagtcttgct acgtggcaca gggcaaacct    120
gactcccttt gggcctcagt ttcccctccc cttcatgana tgaaaagaat actactttt      180
cttgttggtc taacnttgct ggacncaaag tgtngtcatt attgttgtat tgggtgatgt    240
gtncaaaact gcagaagctc actgcctatg agaggaanta agagagatag tggatganag    300
ggacanaagg agtcattatt tggtatagat ccacccntcc caacctttct ctcctcagtc    360
cctgcncctc atgtntctgg tntggtgagt cctttgtgcc accanccatc atgctttgca    420
ttgctgccat cctgggaagg gggtgnatcg tctcacaact tgttgtcatc gtttganatg    480
catgctttct tnatnaaaca aanaaannaa tgtttgacag ngtttaaaat aaaaaanaaa    540
caaaa                                                                545
```

<210> SEQ ID NO 52
<211> LENGTH: 678
<212> TYPE: DNA
<213> ORGANISM: Homo sapiens
<220> FEATURE:
<221> NAME/KEY: modified_base
<222> LOCATION: (98)
<223> OTHER INFORMATION: Where n is a, c, g or t
<221> NAME/KEY: modified_base
<222> LOCATION: (119)
<223> OTHER INFORMATION: Where n is a, c, g or t
<221> NAME/KEY: modified_base
<222> LOCATION: (121)
<223> OTHER INFORMATION: Where n is a, c, g or t
<221> NAME/KEY: modified_base
<222> LOCATION: (131)
<223> OTHER INFORMATION: Where n is a, c, g or t
<221> NAME/KEY: modified_base
<222> LOCATION: (136)
<223> OTHER INFORMATION: Where n is a, c, g or t
<221> NAME/KEY: modified_base
<222> LOCATION: (139)
<223> OTHER INFORMATION: Where n is a, c, g or t
<221> NAME/KEY: modified_base
<222> LOCATION: (140)
<223> OTHER INFORMATION: Where n is a, c, g or t
<221> NAME/KEY: modified_base
<222> LOCATION: (142)
<223> OTHER INFORMATION: Where n is a, c, g or t
<221> NAME/KEY: modified_base
<222> LOCATION: (143)
<223> OTHER INFORMATION: Where n is a, c, g or t
<221> NAME/KEY: modified_base
<222> LOCATION: (163)

-continued

```
<223> OTHER INFORMATION: Where n is a, c, g or t
<221> NAME/KEY: modified_base
<222> LOCATION: (168)
<223> OTHER INFORMATION: Where n is a, c, g or t
<221> NAME/KEY: modified_base
<222> LOCATION: (172)
<223> OTHER INFORMATION: Where n is a, c, g or t
<221> NAME/KEY: modified_base
<222> LOCATION: (176)
<223> OTHER INFORMATION: Where n is a, c, g or t
<221> NAME/KEY: modified_base
<222> LOCATION: (184)
<223> OTHER INFORMATION: Where n is a, c, g or t
<221> NAME/KEY: modified_base
<222> LOCATION: (189)
<223> OTHER INFORMATION: Where n is a, c, g or t
<221> NAME/KEY: modified_base
<222> LOCATION: (190)
<223> OTHER INFORMATION: Where n is a, c, g or t
<221> NAME/KEY: modified_base
<222> LOCATION: (191)
<223> OTHER INFORMATION: Where n is a, c, g or t
<221> NAME/KEY: modified_base
<222> LOCATION: (200)
<223> OTHER INFORMATION: Where n is a, c, g or t
<221> NAME/KEY: modified_base
<222> LOCATION: (201)
<223> OTHER INFORMATION: Where n is a, c, g or t
<221> NAME/KEY: modified_base
<222> LOCATION: (205)
<223> OTHER INFORMATION: Where n is a, c, g or t
<221> NAME/KEY: modified_base
<222> LOCATION: (207)
<223> OTHER INFORMATION: Where n is a, c, g or t
<221> NAME/KEY: modified_base
<222> LOCATION: (221)
<223> OTHER INFORMATION: Where n is a, c, g or t
<221> NAME/KEY: modified_base
<222> LOCATION: (223)
<223> OTHER INFORMATION: Where n is a, c, g or t
<221> NAME/KEY: modified_base
<222> LOCATION: (229)
<223> OTHER INFORMATION: Where n is a, c, g or t
<221> NAME/KEY: modified_base
<222> LOCATION: (230)
<223> OTHER INFORMATION: Where n is a, c, g or t
<221> NAME/KEY: modified_base
<222> LOCATION: (237)
<223> OTHER INFORMATION: Where n is a, c, g or t
<221> NAME/KEY: modified_base
<222> LOCATION: (240)
<223> OTHER INFORMATION: Where n is a, c, g or t
<221> NAME/KEY: modified_base
<222> LOCATION: (241)
<223> OTHER INFORMATION: Where n is a, c, g or t
<221> NAME/KEY: modified_base
<222> LOCATION: (255)
<223> OTHER INFORMATION: Where n is a, c, g or t
<221> NAME/KEY: modified_base
<222> LOCATION: (264)
<223> OTHER INFORMATION: Where n is a, c, g or t
<221> NAME/KEY: modified_base
<222> LOCATION: (266)
<223> OTHER INFORMATION: Where n is a, c, g or t
<221> NAME/KEY: modified_base
<222> LOCATION: (267)
<223> OTHER INFORMATION: Where n is a, c, g or t
<221> NAME/KEY: modified_base
<222> LOCATION: (276)
<223> OTHER INFORMATION: Where n is a, c, g or t
<221> NAME/KEY: modified_base
<222> LOCATION: (280)
<223> OTHER INFORMATION: Where n is a, c, g or t
<221> NAME/KEY: modified_base
<222> LOCATION: (288)
<223> OTHER INFORMATION: Where n is a, c, g or t
<221> NAME/KEY: modified_base
<222> LOCATION: (289)
<223> OTHER INFORMATION: Where n is a, c, g or t
```

-continued

```
<221> NAME/KEY: modified_base
<222> LOCATION: (291)
<223> OTHER INFORMATION: Where n is a, c, g or t
<221> NAME/KEY: modified_base
<222> LOCATION: (297)
<223> OTHER INFORMATION: Where n is a, c, g or t
<221> NAME/KEY: modified_base
<222> LOCATION: (301)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (308)
<223> OTHER INFORMATION: Where n is a, c, g or t
<221> NAME/KEY: modified_base
<222> LOCATION: (314)
<223> OTHER INFORMATION: Where n is a, c, g or t
<221> NAME/KEY: modified_base
<222> LOCATION: (315)
<223> OTHER INFORMATION: Where n is a, c, g or t
<221> NAME/KEY: modified_base
<222> LOCATION: (326)
<223> OTHER INFORMATION: Where n is a, c, g or t
<221> NAME/KEY: modified_base
<222> LOCATION: (332)
<223> OTHER INFORMATION: Where n is a, c, g or t
<221> NAME/KEY: modified_base
<222> LOCATION: (335)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (339)
<223> OTHER INFORMATION: Where n is a, c, g or t
<221> NAME/KEY: modified_base
<222> LOCATION: (341)
<223> OTHER INFORMATION: Where n is a, c, g or t
<221> NAME/KEY: modified_base
<222> LOCATION: (343)
<223> OTHER INFORMATION: Where n is a, c, g or t
<221> NAME/KEY: modified_base
<222> LOCATION: (344)
<223> OTHER INFORMATION: Where n is a, c, g or t
<221> NAME/KEY: modified_base
<222> LOCATION: (345)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (350)
<223> OTHER INFORMATION: Where n is a, c, g or t
<221> NAME/KEY: modified_base
<222> LOCATION: (355)
<223> OTHER INFORMATION: Where n is a, c, g or t
<221> NAME/KEY: modified_base
<222> LOCATION: (356)
<223> OTHER INFORMATION: Where n is a, c, g or t
<221> NAME/KEY: modified_base
<222> LOCATION: (358)
<223> OTHER INFORMATION: Where n is a, c, g or t
<221> NAME/KEY: modified_base
<222> LOCATION: (362)
<223> OTHER INFORMATION: Where n is a, c, g or t
<221> NAME/KEY: modified_base
<222> LOCATION: (363)
<223> OTHER INFORMATION: Where n is a, c, g or t
<221> NAME/KEY: modified_base
<222> LOCATION: (372)
<223> OTHER INFORMATION: Where n is a, c, g or t
<221> NAME/KEY: modified_base
<222> LOCATION: (379)
<223> OTHER INFORMATION: Where n is a, c, g or t
<221> NAME/KEY: modified_base
<222> LOCATION: (395)
<223> OTHER INFORMATION: Where n is a, c, g or t
<221> NAME/KEY: modified_base
```

-continued

```
<222> LOCATION: (397)
<223> OTHER INFORMATION: Where n is a, c, g or t
<221> NAME/KEY: modified_base
<222> LOCATION: (398)
<223> OTHER INFORMATION: Where n is a, c, g or t
<221> NAME/KEY: modified_base
<222> LOCATION: (400)
<223> OTHER INFORMATION: Where n is a, c, g or t
<221> NAME/KEY: modified_base
<222> LOCATION: (403)
<223> OTHER INFORMATION: Where n is a, c, g or t
<221> NAME/KEY: modified_base
<222> LOCATION: (412)
<223> OTHER INFORMATION: Where n is a, c, g or t
<221> NAME/KEY: modified_base
<222> LOCATION: (414)
<223> OTHER INFORMATION: Where n is a, c, g or t
<221> NAME/KEY: modified_base
<222> LOCATION: (421)
<223> OTHER INFORMATION: Where n is a, c, g or t
<221> NAME/KEY: modified_base
<222> LOCATION: (423)
<223> OTHER INFORMATION: Where n is a, c, g or t
<221> NAME/KEY: modified_base
<222> LOCATION: (431)
<223> OTHER INFORMATION: Where n is a, c, g or t
<221> NAME/KEY: modified_base
<222> LOCATION: (435)
<223> OTHER INFORMATION: Where n is a, c, g or t
<221> NAME/KEY: modified_base
<222> LOCATION: (438)
<223> OTHER INFORMATION: Where n is a, c, g or t
<221> NAME/KEY: modified_base
<222> LOCATION: (439
<223> OTHER INFORMATION: Where n is a, c, g or t
<221> NAME/KEY: modified_base
<222> LOCATION: (457)
<223> OTHER INFORMATION: Where n is a, c, g or t
<221> NAME/KEY: modified_base
<222> LOCATION: (463)
<223> OTHER INFORMATION: Where n is a, c, g or t
<221> NAME/KEY: modified_base
<222> LOCATION: (467)
<223> OTHER INFORMATION: Where n is a, c, g or t
<221> NAME/KEY: modified_base
<222> LOCATION: (471)
<223> OTHER INFORMATION: Where n is a, c, g or t
<221> NAME/KEY: modified_base
<222> LOCATION: (474)
<223> OTHER INFORMATION: Where n is a, c, g or t
<221> NAME/KEY: modified_base
<222> LOCATION: (480)
<223> OTHER INFORMATION: Where n is a, c, g or t
<221> NAME/KEY: modified_base
<222> LOCATION: (483)
<223> OTHER INFORMATION: Where n is a, c, g or t
<221> NAME/KEY: modified_base
<222> LOCATION: (484)
<223> OTHER INFORMATION: Where n is a, c, g or t
<221> NAME/KEY: modified_base
<222> LOCATION: (487)
<223> OTHER INFORMATION: Where n is a, c, g or t
<221> NAME/KEY: modified_base
<222> LOCATION: (490)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (492)
<223> OTHER INFORMATION: Where n is a, c, g or t
<221> NAME/KEY: modified_base
<222> LOCATION: (493)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (500)
```

-continued

```
<223> OTHER INFORMATION: Where n is a, c, g or t
<221> NAME/KEY: modified_base
<222> LOCATION: (504)
<223> OTHER INFORMATION: Where n is a, c, g or t
<221> NAME/KEY: modified_base
<222> LOCATION: (508)
<223> OTHER INFORMATION: Where n is a, c, g or t
<221> NAME/KEY: modified_base
<222> LOCATION: (518)
<223> OTHER INFORMATION: Where n is a, c, g or t
<221> NAME/KEY: modified_base
<222> LOCATION: (536)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (549)
<223> OTHER INFORMATION: Where n is a, c, g or t
<221> NAME/KEY: modified_base
<222> LOCATION: (551)
<223> OTHER INFORMATION: Where n is a, c, g or t
<221> NAME/KEY: modified_base
<222> LOCATION: (552)
<223> OTHER INFORMATION: Where n is a, c, g or t
<221> NAME/KEY: modified_base
<222> LOCATION: (554)
<223> OTHER INFORMATION: Where n is a, c, g or t
<221> NAME/KEY: modified_base
<222> LOCATION: (556)
<223> OTHER INFORMATION: Where n is a, c, g or t
<221> NAME/KEY: modified_base
<222> LOCATION: (557)
<223> OTHER INFORMATION: Where n is a, c, g or t
<221> NAME/KEY: modified_base
<222> LOCATION: (562)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (571)
<223> OTHER INFORMATION: Where n is a, c, g or t
<221> NAME/KEY: modified_base
<222> LOCATION: (572)
<223> OTHER INFORMATION: Where n is a, c, g or t
<221> NAME/KEY: modified_base
<222> LOCATION: (576)
<223> OTHER INFORMATION: Where n is a, c, g or t
<221> NAME/KEY: modified_base
<222> LOCATION: (579)
<223> OTHER INFORMATION: Where n is a, c, g or t
<221> NAME/KEY: modified_base
<222> LOCATION: (590)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (595)
<223> OTHER INFORMATION: Where n is a, c, g or t
<221> NAME/KEY: modified_base
<222> LOCATION: (598)
<223> OTHER INFORMATION: Where n is a, c, g or t
<221> NAME/KEY: modified_base
<222> LOCATION: (606)
<223> OTHER INFORMATION: Where n is a, c, g or t
<221> NAME/KEY: modified_base
<222> LOCATION: (609)
<223> OTHER INFORMATION: Where n is a, c, g or t
<221> NAME/KEY: modified_base
<222> LOCATION: (613)
<223> OTHER INFORMATION: Where n is a, c, g or t
<221> NAME/KEY: modified_base
<222> LOCATION: (620)
<223> OTHER INFORMATION: Where n is a, c, g or t
```

<221> NAME/KEY: modified_base
<222> LOCATION: (622)
<223> OTHER INFORMATION: Where n is a, c, g or t
<221> NAME/KEY: modified_base
<222> LOCATION: (624)
<223> OTHER INFORMATION: Where n is a, c, g or t
<221> NAME/KEY: modified_base
<222> LOCATION: (626)
<223> OTHER INFORMATION: Where n is a, c, g or t
<221> NAME/KEY: modified_base
<222> LOCATION: (631)
<223> OTHER INFORMATION: Where n is a, c, g or t
<221> NAME/KEY: modified_base
<222> LOCATION: (634)
<223> OTHER INFORMATION: Where n is a, c, g or t
<221> NAME/KEY: modified_base
<222> LOCATION: (638)
<223> OTHER INFORMATION: Where n is a, c, g or t
<221> NAME/KEY: modified_base
<222> LOCATION: (641)
<223> OTHER INFORMATION: Where n is a, c, g or t
<221> NAME/KEY: modified_base
<222> LOCATION: (647)
<223> OTHER INFORMATION: Where n is a, c, g or t
<221> NAME/KEY: modified_base
<222> LOCATION: (654)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (661)
<223> OTHER INFORMATION: Where n is a, c, g or t
<221> NAME/KEY: modified_base
<222> LOCATION: (664)
<223> OTHER INFORMATION: Where n is a, c, g or t

<400> SEQUENCE: 52

| | | | | | |
|---|---|---|---|---|---|
| actagtagaa | gaactttgcc | gcttttgtgc | ctctcacagg | cgcctaaagt | cattgccatg | 60 |
| ggaggaagac | gatttggggg | gggagggggg | gggggcangg | tccgtggggc | tttccctant | 120 |
| ntatctccat | ntccantgnn | cnntgtcgcc | tcttccctcg | tcncattnga | anttantccc | 180 |
| tggncccnn | ncctctccn | ncctncncct | cccccctccg | ncncctccnn | cttttttntan | 240 |
| ncttccccat | ctccntcccc | cctnanngtc | ccaacnccgn | cagcaatnnc | ncacttnctc | 300 |
| nctccncncc | tccnnccgtt | cttctnttct | cnacntntnc | ncnnntnccn | tgccnntnaa | 360 |
| annctctccc | cnctgcaanc | gattctctcc | ctccncnnan | ctntccactc | cntncttctc | 420 |
| ncncgctcct | nttcntcnnc | ccacctctcn | ccttcgnccc | cantacnctc | nccncccttn | 480 |
| cgnntcnttn | nnntcctcnn | accncccncc | tcccttcncc | cctcttctcc | ccggtntntc | 540 |
| tctctcccnc | nncncnncct | cnncccntcc | nngcgnccnt | ttccgccccn | cnccnccntt | 600 |
| ccttcntcnc | cantccatcn | cntntnccat | nctcctncc | nctcacnccc | gctncccccn | 660 |
| ntctctttca | cacngtcc | | | | | 678 |

<210> SEQ ID NO 53
<211> LENGTH: 502
<212> TYPE: DNA
<213> ORGANISM: Homo sapiens
<220> FEATURE:
<221> NAME/KEY: modified_base
<222> LOCATION: (139)
<223> OTHER INFORMATION: Where n is a, c, g or t
<221> NAME/KEY: modified_base
<222> LOCATION: (146)
<223> OTHER INFORMATION: Where n is a, c, g or t
<221> NAME/KEY: modified_base
<222> LOCATION: (215)
<223> OTHER INFORMATION: Where n is a, c, g or t
<221> NAME/KEY: modified_base

```
<222> LOCATION: (217)
<223> OTHER INFORMATION: Where n is a, c, g or t
<221> NAME/KEY: modified_base
<222> LOCATION: (257)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (289)
<223> OTHER INFORMATION: Where n is a, c, g or t
<221> NAME/KEY: modified_base
<222> LOCATION: (386)
<223> OTHER INFORMATION: Where n is a, c, g or t
<221> NAME/KEY: modified_base
<222> LOCATION: (420)
<223> OTHER INFORMATION: Where n is a, c, g or t
<221> NAME/KEY: modified_base
<222> LOCATION: (452)
<223> OTHER INFORMATION: Where n is a, c, g or t
<221> NAME/KEY: modified_base
<222> LOCATION: (457)
<223> OTHER INFORMATION: Where n is a, c, g or t
<221> NAME/KEY: modified_base
<222> LOCATION: (461)
<223> OTHER INFORMATION: Where n is a, c, g or t
<221> NAME/KEY: modified_base
<222> LOCATION: (466)
<223> OTHER INFORMATION: Where n is a, c, g or t
<221> NAME/KEY: modified_base
<222> LOCATION: (482)
<223> OTHER INFORMATION: Where n is a, c, g or t
<221> NAME/KEY: modified_base
<222> LOCATION: (486)
<223> OTHER INFORMATION: Where n is a, c, g or t

<400> SEQUENCE: 53
tgaagatcct ggtgtcgcca tgggccgccg ccccgcccgt tgttaccggt attgtaagaa      60
caagccgtac ccaaagtctc gcttctgccg aggtgtccct gatgccaaaa ttcgcatttt     120
tgacctgggg cggaaaaang caaaantgga tgagtctccg ctttgtggcc acatggtgtc     180
agatcaatat gagcagctgt cctctgaagc cctgnangct gcccgaattt gtgccaataa     240
gtacatggta aaaagtngtg gcnaagatgc ttccatatcc gggtgcggnt ccacccctctc    300 cacgtcatcc gcatcaacaa gatgttgtcc tgtgctgggg ctgacaggct cccaacaggc    360
atgcgaagtg cctttggaaa acccanggca ctgtggccag ggttcacatt gggccaattn    420
atcatgttca tccgcaccaa ctgcagaaca angaacntgt naattnaagc cctgcccagg    480
gncaanttca aatttcccgg cc                                             502

<210> SEQ ID NO 54
<211> LENGTH: 494
<212> TYPE: DNA
<213> ORGANISM: Homo sapiens
<220> FEATURE:
<221> NAME/KEY: modified_base
<222> LOCATION: (431)
<223> OTHER INFORMATION: Where n is a, c, g or t
<221> NAME/KEY: modified_base
<222> LOCATION: (442)
<223> OTHER INFORMATION: Where n is a, c, g or t
<221> NAME/KEY: modified_base
<222> LOCATION: (445)
<223> OTHER INFORMATION: Where n is a, c, g or t

<400> SEQUENCE: 54
actagtccaa gaaaaatatg cttaatgtat attacaaagg ctttgtatat gttaacctgt      60
tttaatgcca aaagtttgct tgtccacaa tttccttaag acctcttcag aaagggattt     120
gtttgcctta atgaatactg ttgggaaaaa acacagtata atgagtgaaa agggcagaag    180
```

```
caagaaattt ctacatctta gcgactccaa gaagaatgag tatccacatt tagatggcac      240
attatgagga ctttaatctt tccttaaaca caataatgtt ttcttttttc ttttattcac      300
atgatttcta agtatatttt tcatgcagga cagttttca accttgatgt acagtgactg      360
tgttaaattt ttctttcagt ggcaacctct ataatcttta aaatatggtg agcatcttgt      420
ctgttttgaa ngggatatga cnatnaatct atcagatggg aaatcctgtt tccaagttag      480
aaaaaaaaaa aaaa                                                        494

<210> SEQ ID NO 55
<211> LENGTH: 606
<212> TYPE: DNA
<213> ORGANISM: Homo sapiens
<220> FEATURE:
<221> NAME/KEY: modified_base
<222> LOCATION: (375)
<223> OTHER INFORMATION: Where n is a, c, g or t
<221> NAME/KEY: modified_base
<222> LOCATION: (395)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (559)
<223> OTHER INFORMATION: Where n is a, c, g or t
<221> NAME/KEY: modified_base
<222> LOCATION: (569)
<223> OTHER INFORMATION: Where n is a, c, g or t
<221> NAME/KEY: modified_base
<222> LOCATION: (578)
<223> OTHER INFORMATION: Where n is a, c, g or t
<221> NAME/KEY: modified_base
<222> LOCATION: (581)
<223> OTHER INFORMATION: Where n is a, c, g or t

<400> SEQUENCE: 55
actagtaaaa agcagcattg ccaaataatc cctaattttc cactaaaaat ataatgaaat       60
gatgttaagc ttttttgaaaa gtttaggtta aacctactgt tgttagatta atgtatttgt      120 tgcttcccctt tatctggaat gtggcattag ctttttttatt ttaaccctct ttaattctta    180
ttcaattcca tgacttaagg ttggagagct aaacactggg attttttggat aacagactga     240 cagttttgca taattataat cggcattgta catagaaagg atatggctac cttttgttaa      300
atctgcactt tctaaatatc aaaaaaggga aatgaagtat aaatcaattt ttgtataatc      360
tgtttgaaac atganttta tttgcttaat attanggctt tgcccttttc tgttagtctc       420
ttgggatcct gtgtaaaact gttctcatta acaccaaac agttaagtcc attctctggt       480
actagctaca aattccgttt catattctac ntaacaattt aaattaactg aaatatttct      540
anatggtcta cttctgtcnt ataaaaacna aacttgantt nccaaaaaaa aaaaaaaaaa      600
aaaaaa                                                                606

<210> SEQ ID NO 56
<211> LENGTH: 183
<212> TYPE: DNA
<213> ORGANISM: Homo sapiens

<400> SEQUENCE: 56
actagtatat ttaaacttac aggcttattt gtaatgtaaa ccaccatttt aatgtactgt       60
aattaacatg gttataatac gtacaatcct tccctcatcc catcacacaa cttttttttgt    120
```

```
gtgtgataaa ctgattttgg tttgcaataa aaccttgaaa aataaaaaaa aaaaaaaaaa    180
aaa                                                                  183

<210> SEQ ID NO 57
<211> LENGTH: 622
<212> TYPE: DNA
<213> ORGANISM: Homo sapiens
<220> FEATURE:
<221> NAME/KEY: modified_base
<222> LOCATION: (358)
<223> OTHER INFORMATION: Where n is a, c, g or t
<221> NAME/KEY: modified_base
<222> LOCATION: (368)
<223> OTHER INFORMATION: Where n is a, c, g or t
<221> NAME/KEY: modified_base
<222> LOCATION: (412)
<223> OTHER INFORMATION: Where n is a, c, g or t
<221> NAME/KEY: modified_base
<222> LOCATION: (414)
<223> OTHER INFORMATION: Where n is a, c, g or t
<221> NAME/KEY: modified_base
<222> LOCATION: (425)
<223> OTHER INFORMATION: Where n is a, c, g or t
<221> NAME/KEY: modified_base
<222> LOCATION: (430)
<223> OTHER INFORMATION: Where n is a, c, g or t
<221> NAME/KEY: modified_base
<222> LOCATION: (453)
<223> OTHER INFORMATION: Where n is a, c, g or t
<221> NAME/KEY: modified_base
<222> LOCATION: (455)
<223> OTHER INFORMATION: Where n is a, c, g or t
<221> NAME/KEY: modified_base
<222> LOCATION: (469)
<223> OTHER INFORMATION: Where n is a, c, g or t
<221> NAME/KEY: modified_base
<222> LOCATION: (475)
<223> OTHER INFORMATION: Where n is a, c, g or t
<221> NAME/KEY: modified_base
<222> LOCATION: (495)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (529)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (564)
<223> OTHER INFORMATION: Where n is a, c, g or t
<221> NAME/KEY: modified_base
<222> LOCATION: (575)
<223> OTHER INFORMATION: Where n is a, c, g or t
<221> NAME/KEY: modified_base
<222> LOCATION: (590)
<223> OTHER INFORMATION: Where n is a, c, g or t

<400> SEQUENCE: 57
actagtcact actgtcttct ccttgtagct aatcaatcaa tattcttccc ttgcctgtgg     60
gcagtggaga gtgctgctgg gtgtacgctg cacctgccca ctgagttggg gaaagaggat    120
aatcagtgag cactgttctg ctcagagctc ctgatctacc ccaccccta ggatccagga    180 ctgggtcaaa gctgcatgaa accaggccct ggcagcaacc tgggaatggc tggaggtggg    240
agagaacctg acttctcttt ccctctccct cctccaacat tactggaact ctatcctgtt    300
agggatcttc tgagcttgtt tccctgctgg gtgggacaga agacaaagga gaagggangg    360
tctacaanaa gcagcccttc tttgtcctct ggggttaatg agcttgacct ananttcatg    420
```

| | | |
|---|---|---|
| gaganaccan aagcctctga ttttaattt ccntnaaatg tttgaagtnt atatntacat | 480 | |
| atatatattt ctttnaatnt ttgagtcttt gatatgtctt aaaatccant ccctctgccn | 540 | |
| gaaacctgaa ttaaaaccat gaanaaaaat gtttnccttta aagatgttan taattaattg | 600 | |
| aaacttgaaa aaaaaaaaaa aa | 622 | |

<210> SEQ ID NO 58
<211> LENGTH: 433
<212> TYPE: DNA
<213> ORGANISM: Homo sapiens

<400> SEQUENCE: 58

| | | |
|---|---|---|
| gaacaaattc tgattggtta tgtaccgtca aaagacttga agaaatttca tgattttgca | 60 | |
| gtgtggaagc gttgaaaatt gaaagttact gcttttccac ttgctcatat agtaaaggga | 120 | |
| tcctttcagc tgccagtgtt gaataatgta tcatccagag tgatgttatc tgtgacagtc | 180 | |
| accagcttta agctgaacca ttttatgaat accaaataaa tagacctctt gtactgaaaa | 240 | |
| catatttgtg actttaatcg tgctgcttgg atagaaatat ttttactggt tcttctgaat | 300 | |
| tgacagtaaa cctgtccatt atgaatggcc tactgttcta ttatttgttt tgacttgaat | 360 | |
| ttatccacca aagacttcat ttgtgtatca tcaataaagt tgtatgtttc aactgaaaaa | 420 | |
| aaaaaaaaaa aaa | 433 | |

<210> SEQ ID NO 59
<211> LENGTH: 649
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<221> NAME/KEY: modified_base
<222> LOCATION: (190)
<223> OTHER INFORMATION: Where n is a, c, g or t
<221> NAME/KEY: modified_base
<222> LOCATION: (217)
<223> OTHER INFORMATION: Where n is a, c, g or t
<221> NAME/KEY: modified_base
<222> LOCATION: (430)
<223> OTHER INFORMATION: Where n is a, c, g or t
<221> NAME/KEY: modified_base
<222> LOCATION: (433)
<223> OTHER INFORMATION: Where n is a, c, g or t
<221> NAME/KEY: modified_base
<222> LOCATION: (484)
<223> OTHER INFORMATION: Where n is a, c, g or t
<221> NAME/KEY: modified_base
<222> LOCATION: (544)
<223> OTHER INFORMATION: Where n is a, c, g or t
<221> NAME/KEY: modified_base
<222> LOCATION: (550)
<223> OTHER INFORMATION: Where n is a, c, g or t
<221> NAME/KEY: modified_base
<222> LOCATION: (577)
<223> OTHER INFORMATION: Where n is a, c, g or t
<221> NAME/KEY: modified_base
<222> LOCATION: (583)
<223> OTHER INFORMATION: Where n is a, c, g or t
<221> NAME/KEY: modified_base
<222> LOCATION: (594)
<223> OTHER INFORMATION: Where n is a, c, g or t

<400> SEQUENCE: 59

| | | |
|---|---|---|
| actagttatt atctgacttt cnggttataa tcattctaat gagtgtgaag tagcctctgg | 60 | |
| tgtcatttgg atttgcattt ctctgatgag tgatgctatc aagcaccttt gctggtgctg | 120 | |
| ttggccatat gtgtatgttc cctggagaag tgtctgtgct gagccttggc ccacttttta | 180 | |

```
attaggcgtn tgtctttta ttactgagtt gtaaganttc tttatatatt ctggattcta     240
gacccttatc agatacatgg tttgcaaata ttttctccca ttctgtgggt tgtgttttca    300
ctttatcgat aatgtcctta gacatataat aaatttgtat tttaaaagtg acttgatttg   360
ggctgtgcaa ggtgggctca cgcttgtaat cccagcactt tgggagactg aggtgggtgg   420
atcatatgan gangctagga gttcgaggtc agcctggcca gcatagcgaa aacttgtctc   480
tacnaaaaat acaaaaatta gtcaggcatg gtggtgcacg tctgtaatac cagcttctca   540
ggangctgan gcacaaggat cacttgaacc ccagaangaa gangttgcag tganctgaag   600
atcatgccag ggcaacaaaa atgagaactt gtttaaaaaa aaaaaaaaa               649
```

```
<210> SEQ ID NO 60
<211> LENGTH: 423
<212> TYPE: DNA
<213> ORGANISM: Homo sapiens
<220> FEATURE:
<221> NAME/KEY: modified_base
<222> LOCATION: (209)
<223> OTHER INFORMATION: Where n is a, c, g or t
<221> NAME/KEY: modified_base
<222> LOCATION: (222)
<223> OTHER INFORMATION: Where n is a, c, g or t
<221> NAME/KEY: modified_base
<222> LOCATION: (277)
<223> OTHER INFORMATION: Where n is a, c, g or t
<221> NAME/KEY: modified_base
<222> LOCATION: (389)
<223> OTHER INFORMATION: Where n is a, c, g or t
<221> NAME/KEY: modified_base
<222> LOCATION: (398)
<223> OTHER INFORMATION: Where n is a, c, g or t

<400> SEQUENCE: 60
```

```
actagttcag gccttccagt tcactgacaa acatggggaa gtgtgcccag ctggctggaa    60
acctggcagt gataccatca agcctgatgt ccaaaagagc aaagaatatt tctccaagca   120
gaagtgagcg ctgggctgtt ttagtgccag gctgcggtgg gcagccatga gaacaaaacc   180
tcttctgtat tttttttttc cattagtana acacaagact cngattcagc cgaattgtgg   240
tgtcttacaa ggcagggctt tcctacaggg ggtgganaaa acagcctttc ttcctttggt   300
aggaatggcc tgagttggcg ttgtgggcag gctactggtt tgtatgatgt attagtagag   360
caacccatta atcttttgta gtttgtatna aacttganct gagaccttaa acaaaaaaaa   420
aaa                                                                423
```

```
<210> SEQ ID NO 61
<211> LENGTH: 423
<212> TYPE: DNA
<213> ORGANISM: Homo sapiens
<220> FEATURE:
<221> NAME/KEY: modified_base
<222> LOCATION: (195)
<223> OTHER INFORMATION: Where n is a, c, g or t
<221> NAME/KEY: modified_base
<222> LOCATION: (285)
<223> OTHER INFORMATION: Where n is a, c, g or t
<221> NAME/KEY: modified_base
<222> LOCATION: (295)
<223> OTHER INFORMATION: Where n is a, c, g or t
<221> NAME/KEY: modified_base
<222> LOCATION: (329)
<223> OTHER INFORMATION: Where n is a, c, g or t
<221> NAME/KEY: modified_base
<222> LOCATION: (335)
<223> OTHER INFORMATION: Where n is a, c, g or t
<221> NAME/KEY: modified_base
```

```
<222> LOCATION: (340)
<223> OTHER INFORMATION: Where n is a, c, g or t
<221> NAME/KEY: modified_base
<222> LOCATION: (347)
<223> OTHER INFORMATION: Where n is a, c, g or t
<221> NAME/KEY: modified_base
<222> LOCATION: (367)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (383)
<223> OTHER INFORMATION: Where n is a, c, g or t
<221> NAME/KEY: modified_base
<222> LOCATION: (391)
<223> OTHER INFORMATION: Where n is a, c, g or t
<221> NAME/KEY: modified_base
<222> LOCATION: (396)
<223> OTHER INFORMATION: Where n is a, c, g or t
<221> NAME/KEY: modified_base
<222> LOCATION: (418)
<223> OTHER INFORMATION: Where n is a, c, g or t

<400> SEQUENCE: 61
cgggactgga atgtaaagtg aagttcggag ctctgagcac gggctcttcc cgccgggtcc      60
tccctcccca gacccagag ggagaggccc accccgccca gccccgcccc agccctgct       120 caggtctgag tatggctggg agtcgggggc cacaggcctc tagctgtgct gctcaagaag    180
actggatcag ggtanctaca agtggccggg ccttgccttt gggattctac cctgttccta    240
atttggtgtt ggggtgcggg gtccctggcc ccctttccca cactncctcc ctccngacag    300
caacctccct tggggcaatt gggcctggnt ctccncccgn tgttgcnacc ctttgttggt    360
ttaaggnctt taaaaatgtt annttttccc ntgccngggt taaaaagga aaaactnaa     420 aaa                                                                  423

<210> SEQ ID NO 62
<211> LENGTH: 683
<212> TYPE: DNA
<213> ORGANISM: Homo sapiens
<220> FEATURE:
<221> NAME/KEY: modified_base
<222> LOCATION: (218)
<223> OTHER INFORMATION: Where n is a, c, g or t
<221> NAME/KEY: modified_base
<222> LOCATION: (291)
<223> OTHER INFORMATION: Where n is a, c, g or t
<221> NAME/KEY: modified_base
<222> LOCATION: (305)
<223> OTHER INFORMATION: Where n is a, c, g or t
<221> NAME/KEY: modified_base
<222> LOCATION: (411)
<223> OTHER INFORMATION: Where n is a, c, g or t
<221> NAME/KEY: modified_base
<222> LOCATION: (416)
<223> OTHER INFORMATION: Where n is a, c, g or t
<221> NAME/KEY: modified_base
<222> LOCATION: (441)
<223> OTHER INFORMATION: Where n is a, c, g or t
<221> NAME/KEY: modified_base
<222> LOCATION: (443)
<223> OTHER INFORMATION: Where n is a, c, g or t
<221> NAME/KEY: modified_base
<222> LOCATION: (453)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (523)
<223> OTHER INFORMATION: Where n is a, c, g or t
<221> NAME/KEY: modified_base
```

-continued

```
<222> LOCATION: (536)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (547)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (588)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (595)
<223> OTHER INFORMATION: Where n is a, c, g or t
<221> NAME/KEY: modified_base
<222> LOCATION: (603)
<223> OTHER INFORMATION: Where n is a, c, g or t
<221> NAME/KEY: modified_base
<222> LOCATION: (621)
<223> OTHER INFORMATION: Where n is a, c, g or t
<221> NAME/KEY: modified_base
<222> LOCATION: (628)
<223> OTHER INFORMATION: Where n is a, c, g or t
<221> NAME/KEY: modified_base
<222> LOCATION: (630)
<223> OTHER INFORMATION: Where n is a, c, g or t
<221> NAME/KEY: modified_base
<222> LOCATION: (632)
<223> OTHER INFORMATION: Where n is a, c, g or t
<221> NAME/KEY: modified_base
<222> LOCATION: (644)
<223> OTHER INFORMATION: Where n is a, c, g or t
<221> NAME/KEY: modified_base
<222> LOCATION: (645)
<223> OTHER INFORMATION: Where n is a, c, g or t
<221> NAME/KEY: modified_base
<222> LOCATION: (648)
<223> OTHER INFORMATION: Where n is a, c, g or t
<221> NAME/KEY: modified_base
<222> LOCATION: (655)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (672)
<223> OTHER INFORMATION: Where n is a, c, g or t
<221> NAME/KEY: modified_base
<222> LOCATION: (674)
<223> OTHER INFORMATION: Where n is a, c, g or t
<221> NAME/KEY: modified_base
<222> LOCATION: (676)
<223> OTHER INFORMATION: Where n is a, c, g or t
<221> NAME/KEY: modified_base
<222> LOCATION: (677)
<223> OTHER INFORMATION: Where n is a, c, g or t
<221> NAME/KEY: modified_base
<222> LOCATION: (683)
<223> OTHER INFORMATION: Where n is a, c, g or t

<400> SEQUENCE: 62
gctggagagg ggtacggact ttcttggagt tgtcccaggt tggaatgaga ctgaactcaa      60 gaagaccc taagagactg gggaatggtt cctgccttca ggaaagtgaa agacgcttag      120
gctgtcaaca cttaaaggaa gtccccttga agcccagagt ggacagacta gacccattga    180
tggggccact ggccatggtc cgtggacaag acattccngt gggccatggc acaccggggg    240
ggatcaaaat gtgtacttgt ggggtctcgc cccttgccaa aaccaaacca ntcccactcc    300
tgtcnttgga cttttcttccc attccctcct ccccaaatgc acttcccctc ctccctctgc    360
```

```
ccctcctgtg tttttggaat tctgtttccc tcaaaattgt taattttta nttttngacc    420 atgaacttat gtttggggtc nangttcccc ttnccaatgc atactaatat attaatggtt    480 atttatttt gaaatatttt ttaatgaact tggaaaaaat tnntggaatt tccttncttc    540
cnttttnttt ggggggggtg gggggntggg ttaaaatttt tttggaancc cnatnggaaa    600
ttnttacttg gggcccccct naaaaantn anttccaatt cttnnatngc ccctnttccn    660
ctaaaaaaaa ananannaaa aan                                            683
```

```
<210> SEQ ID NO 63
<211> LENGTH: 731
<212> TYPE: DNA
<213> ORGANISM: Homo sapiens
<220> FEATURE:
<221> NAME/KEY: modified_base
<222> LOCATION: (236)
<223> OTHER INFORMATION: Where n is a, c, g or t
<221> NAME/KEY: modified_base
<222> LOCATION: (249)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (288)
<223> OTHER INFORMATION: Where n is a, c, g or t
<221> NAME/KEY: modified_base
<222> LOCATION: (312)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (323)
<223> OTHER INFORMATION: Where n is a, c, g or t
<221> NAME/KEY: modified_base
<222> LOCATION: (326)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (362)
<223> OTHER INFORMATION: Where n is a, c, g or t
<221> NAME/KEY: modified_base
<222> LOCATION: (370)
<223> OTHER INFORMATION: Where n is a, c, g or t
<221> NAME/KEY: modified_base
<222> LOCATION: (376)
<223> OTHER INFORMATION: Where n is a, c, g or t
<221> NAME/KEY: modified_base
<222> LOCATION: (400)
<223> OTHER INFORMATION: Where n is a, c, g or t
<221> NAME/KEY: modified_base
<222> LOCATION: (411)
<223> OTHER INFORMATION: Where n is a, c, g or t
<221> NAME/KEY: modified_base
<222> LOCATION: (414)
<223> OTHER INFORMATION: Where n is a, c, g or t
<221> NAME/KEY: modified_base
<222> LOCATION: (434)
<223> OTHER INFORMATION: Where n is a, c, g or t
<221> NAME/KEY: modified_base
<222> LOCATION: (436)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (457)
<223> OTHER INFORMATION: Where n is a, c, g or t
```

```
<221> NAME/KEY: modified_base
<222> LOCATION: (473)
<223> OTHER INFORMATION: Where n is a, c, g or t
<221> NAME/KEY: modified_base
<222> LOCATION: (486)
<223> OTHER INFORMATION: Where n is a, c, g or t
<221> NAME/KEY: modified_base
<222> LOCATION: (497)
<223> OTHER INFORMATION: Where n is a, c, g or t
<221> NAME/KEY: modified_base
<222> LOCATION: (498)
<223> OTHER INFORMATION: Where n is a, c, g or t
<221> NAME/KEY: modified_base
<222> LOCATION: (502)
<223> OTHER INFORMATION: Where n is a, c, g or t
<221> NAME/KEY: modified_base
<222> LOCATION: (512)
<223> OTHER INFORMATION: Where n is a, c, g or t
<221> NAME/KEY: modified_base
<222> LOCATION: (531)
<223> OTHER INFORMATION: Where n is a, c, g or t
<221> NAME/KEY: modified_base
<222> LOCATION: (546)
<223> OTHER INFORMATION: Where n is a, c, g or t
<221> NAME/KEY: modified_base
<222> LOCATION: (554)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (565)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (588)
<223> OTHER INFORMATION: Where n is a, c, g or t
<221> NAME/KEY: modified_base
<222> LOCATION: (597)
<223> OTHER INFORMATION: Where n is a, c, g or t
<221> NAME/KEY: modified_base
<222> LOCATION: (608)
<223> OTHER INFORMATION: Where n is a, c, g or t
<221> NAME/KEY: modified_base
<222> LOCATION: (611)
<223> OTHER INFORMATION: Where n is a, c, g or t
<221> NAME/KEY: modified_base
<222> LOCATION: (613)
<223> OTHER INFORMATION: Where n is a, c, g or t
<221> NAME/KEY: modified_base
<222> LOCATION: (615)
<223> OTHER INFORMATION: Where n is a, c, g or t
<221> NAME/KEY: modified_base
<222> LOCATION: (627)
<223> OTHER INFORMATION: Where n is a, c, g or t
<221> NAME/KEY: modified_base
<222> LOCATION: (632)
<223> OTHER INFORMATION: Where n is a, c, g or t
<221> NAME/KEY: modified_base
<222> LOCATION: (640)
<223> OTHER INFORMATION: Where n is a, c, g or t
<221> NAME/KEY: modified_base
<222> LOCATION: (641)
<223> OTHER INFORMATION: Where n is a, c, g or t
<221> NAME/KEY: modified_base
<222> LOCATION: (644)
<223> OTHER INFORMATION: Where n is a, c, g or t
<221> NAME/KEY: modified_base
<222> LOCATION: (654)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (663)
<223> OTHER INFORMATION: Where n is a, c, g or t
<221> NAME/KEY: modified_base
```

```
<222> LOCATION: (665)
<223> OTHER INFORMATION: Where n is a, c, g or t
<221> NAME/KEY: modified_base
<222> LOCATION: (671)
<223> OTHER INFORMATION: Where n is a, c, g or t
<221> NAME/KEY: modified_base
<222> LOCATION: (678)
<223> OTHER INFORMATION: Where n is a, c, g or t
<221> NAME/KEY: modified_base
<222> LOCATION: (692)
<223> OTHER INFORMATION: Where n is a, c, g or t
<221> NAME/KEY: modified_base
<222> LOCATION: (697)
<223> OTHER INFORMATION: Where n is a, c, g or t
<221> NAME/KEY: modified_base
<222> LOCATION: (698)
<223> OTHER INFORMATION: Where n is a, c, g or t
<221> NAME/KEY: modified_base
<222> LOCATION: (699)
<223> OTHER INFORMATION: Where n is a, c, g or t
<221> NAME/KEY: modified_base
<222> LOCATION: (704)
<223> OTHER INFORMATION: Where n is a, c, g or t
<221> NAME/KEY: modified_base
<222> LOCATION: (705)
<223> OTHER INFORMATION: Where n is a, c, g or t
<221> NAME/KEY: modified_base
<222> LOCATION: (712)
<223> OTHER INFORMATION: Where n is a, c, g or t
<221> NAME/KEY: modified_base
<222> LOCATION: (714)
<223> OTHER INFORMATION: Where n is a, c, g or t
<221> NAME/KEY: modified_base
<222> LOCATION: (717)
<223> OTHER INFORMATION: Where n is a, c, g or t
<221> NAME/KEY: modified_base
<222> LOCATION: (718)
<223> OTHER INFORMATION: Where n is a, c, g or t
<221> NAME/KEY: modified_base
<222> LOCATION: (719)
<223> OTHER INFORMATION: Where n is a, c, g or t
<221> NAME/KEY: modified_base
<222> LOCATION: (723)
<223> OTHER INFORMATION: Where n is a, c, g or t
<221> NAME/KEY: modified_base
<222> LOCATION: (725)
<223> OTHER INFORMATION: Where n is a, c, g or t
<221> NAME/KEY: modified_base
<222> LOCATION: (730)
<223> OTHER INFORMATION: Where n is a, c, g or t
<221> NAME/KEY: modified_base
<222> LOCATION: (731)
<223> OTHER INFORMATION: Where n is a, c, g or t

<400> SEQUENCE: 63
actagtcata aagggtgtgc gcgtcttcga cgtggcggtc ttggcgccac tgctgcgaga      60
cccggccctg gacctcaagg tcatccactt ggtgcgtgat cccgcgcgg tggcgagttc     120 acggatccgc tcgcgccacg gcctcatccg tgagagccta caggtggtgc gcagccgaga    180
ccgcgagctc accgcatgcc cttcttggag gccgcgggcc acaagcttgg cgcccanaaa    240
gaaggcgtng ggggcccgca aantaccacg ctctgggcgc tatggaangt cctcttgcaa    300
taatattggt tnaaaanctg canaanagcc cctgcanccc cctgaactgg gntgcagggc    360
cncttacctn gtttggntgc ggttacaaag aacctgtttn ggaaaccct nccnaaaacc    420 ttccgggaaa attntncaaa ttttnttgg ggaattnttg ggtaaacccc ccnaaaatgg    480
gaaacntttt tgccctnnaa antaaaccat tnggttccgg gggcccccc ncaaaaccct    540 tttttnttt tttntgcccc cantnnnccc ccggggcccc tttttttngg ggaaaanccc    600
cccccctncc nananttta aaagggnggg anaattttt nttncccccc gggncccccn    660 gggngntaaaa nggtttcncc ccccgaggg gngggnnnc ctcnnaaaacc cntntcnnna    720
```

```
ccncnttttn n                                                         731
```

<210> SEQ ID NO 64
<211> LENGTH: 313
<212> TYPE: DNA
<213> ORGANISM: Homo sapiens
<220> FEATURE:
<221> NAME/KEY: modified_base
<222> LOCATION: (240)
<223> OTHER INFORMATION: Where n is a, c, g or t

<400> SEQUENCE: 64

```
actagttgtg caaaccacga ctgaagaaag acgaaaagtg ggaaataact tgcaacgtct    60
gttagagatg gttgctacac atgttgggtc tgtagagaaa catcttgagg agcagattgc   120
taaagttgat agagaatatg aagaatgcat gtcagaagat ctctcggaaa atattaaaga   180
gattagagat aagtatgaga agaaagctac tctaattaag tcttctgaag aatgaagatn   240
aaatgttgat catgtatata tatccatagt gaataaaatt gtctcagtaa agttgtaaaa   300
aaaaaaaaaa aaa                                                     313
```

<210> SEQ ID NO 65
<211> LENGTH: 420
<212> TYPE: DNA
<213> ORGANISM: Homo sapiens
<220> FEATURE:
<221> NAME/KEY: modified_base
<222> LOCATION: (400)
<223> OTHER INFORMATION: Where n is a, c, g or t
<221> NAME/KEY: modified_base
<222> LOCATION: (402)
<223> OTHER INFORMATION: Where n is a, c, g or t
<221> NAME/KEY: modified_base
<222> LOCATION: (403)
<223> OTHER INFORMATION: Where n is a, c, g or t
<221> NAME/KEY: modified_base
<222> LOCATION: (404)
<223> OTHER INFORMATION: Where n is a, c, g or t
<221> NAME/KEY: modified_base
<222> LOCATION: (405)
<223> OTHER INFORMATION: Where n is a, c, g or t
<221> NAME/KEY: modified_base
<222> LOCATION: (406)
<223> OTHER INFORMATION: Where n is a, c, g or t
<221> NAME/KEY: modified_base
<222> LOCATION: (409)
<223> OTHER INFORMATION: Where n is a, c, g or t
<221> NAME/KEY: modified_base
<222> LOCATION: (411)
<223> OTHER INFORMATION: Where n is a, c, g or t
<221> NAME/KEY: modified_base
<222> LOCATION: (412)
<223> OTHER INFORMATION: Where n is a, c, g or t
<221> NAME/KEY: modified_base
<222> LOCATION: (414)
<223> OTHER INFORMATION: Where n is a, c, g or t
<221> NAME/KEY: modified_base
<222> LOCATION: (415)
<223> OTHER INFORMATION: Where n is a, c, g or t
<221> NAME/KEY: modified_base
<222> LOCATION: (416)
<223> OTHER INFORMATION: Where n is a, c, g or t

<400> SEQUENCE: 65

```
actagttccc tggcaggcaa gggcttccaa ctgaggcagt gcatgtgtgg cagagagagg    60
caggaagctg gcagtggcag cttctgtgtc tagggagggg tgtggctccc tccttccctg   120
tctgggaggt tggagggaag aatctaggcc ttagcttgcc ctcctgccac ccttcccctt   180
gtagatactg ccttaacact ccctcctctc tcagctgtgg ctgccaccca agccaggttt   240
```

```
ctccgtgctc actaatttat ttccaggaaa ggtgtgtgga agacatgagc cgtgtataat        300
atttgtttta acattttcat tgcaagtatt gaccatcatc cttggttgtg tatcgttgta        360
acacaaatta atgatattaa aaagcatcca aacaaagccn annnnnaana nnannngaaa        420
```

<210> SEQ ID NO 66
<211> LENGTH: 676
<212> TYPE: DNA
<213> ORGANISM: Homo sapiens
<220> FEATURE:
<221> NAME/KEY: modified_base
<222> LOCATION: (328)
<223> OTHER INFORMATION: Where n is a, c, g or t
<221> NAME/KEY: modified_base
<222> LOCATION: (454)
<223> OTHER INFORMATION: Where n is a, c, g or t
<221> NAME/KEY: modified_base
<222> LOCATION: (505)
<223> OTHER INFORMATION: Where n is a, c, g or t
<221> NAME/KEY: modified_base
<222> LOCATION: (555)
<223> OTHER INFORMATION: Where n is a, c, g or t
<221> NAME/KEY: modified_base
<222> LOCATION: (586)
<223> OTHER INFORMATION: Where n is a, c, g or t
<221> NAME/KEY: modified_base
<222> LOCATION: (612)
<223> OTHER INFORMATION: Where n is a, c, g or t
<221> NAME/KEY: modified_base
<222> LOCATION: (636)
<223> OTHER INFORMATION: Where n is a, c, g or t
<221> NAME/KEY: modified_base
<222> LOCATION: (641)
<223> OTHER INFORMATION: Where n is a, c, g or t

<400> SEQUENCE: 66

```
actagttttcc tatgatcatt aaactcattc tcagggttaa gaaaggaatg taaatttctg        60
cctcaatttg tacttcatca ataagttttt gaagagtgca gatttttagt caggtcttaa        120
aaataaactc acaaatctgg atgcatttct aaattctgca aatgtttcct ggggtgactt        180
aacaaggaat aatcccacaa tatacctagc tacctaatac atggagctgg ggctcaaccc        240
actgttttta aggatttgcg cttacttgtg gctgaggaaa aataagtagt tccgagggaa        300
gtagttttta aatgtgagct tatagatngg aaacagaata tcaacttaat tatgaaattt        360
gttagaaacc tgttctcttg ttatctgaat cttgattgca attactattg tactggatag        420
actccagccc attgcaaagt ctcagatatc ttanctgtgt agttgaattc cttgaaaatt        480 cttttttaaga aaaattgga gtttnaaaga aataaacccc tttgttaaat gaagcttggc        540
tttttggtga aaaanaatca tcccgcaggg cttattgttt aaaaanggaa ttttaagcct        600
ccctggaaaa anttgttaat taaatgggga aaatgntggg naaaaattat ccgttagggt        660
ttaaagggaa aactta                                                      676
```

<210> SEQ ID NO 67
<211> LENGTH: 620
<212> TYPE: DNA
<213> ORGANISM: Homo sapiens
<220> FEATURE:
<221> NAME/KEY: modified_base
<222> LOCATION: (419)
<223> OTHER INFORMATION: Where n is a, c, g or t
<221> NAME/KEY: modified_base
<222> LOCATION: (493)
<223> OTHER INFORMATION: Where n is a, c, g or t
<221> NAME/KEY: modified_base
<222> LOCATION: (519)
<223> OTHER INFORMATION: Where n is a, c, g or t
<221> NAME/KEY: modified_base
<222> LOCATION: (568)
<223> OTHER INFORMATION: Where n is a, c, g or t
<221> NAME/KEY: modified_base
<222> LOCATION: (605)
<223> OTHER INFORMATION: Where n is a, c, g or t
<221> NAME/KEY: modified_base
<222> LOCATION: (610)
<223> OTHER INFORMATION: Where n is a, c, g or t

<400> SEQUENCE: 67

```
caccattaaa gctgcttacc aagaacttcc ccagcatttt gacttccttg tttgatagct    60
gaattgtgag caggtgatag aagagccttt ctagttgaac atacagataa tttgctgaat   120
acattccatt taatgaaggg gttacatctg ttacgaagct actaagaagg agcaagagca   180
tagggaaaaa aaatctgatc agaacgcatc aaactcacat gtgcccctc tactacaaac    240
agattgtagt gctgtggtgg tttattccgt tgtgcagaac ttgcaagctg agtcactaaa   300
cccaaagaga ggaaattata ggttagttaa acattgtaat cccaggaact aagtttaatt   360
cactttgaa gtgttttgtt ttttattttt ggtttgtctg atttactttg ggggaaaang   420
ctaaaaaaaa agggatatca atctctaatt cagtgcccac taaaagttgt ccctaaaaag   480
tctttactgg aanttatggg acttttaag ctccaggtnt tttggtcctc caaattaacc    540
ttgcatgggc cccttaaaat tgttgaangg cattcctgcc tctaagtttg gggaaaattc   600
ccccnttttn aaaatttgga                                              620
```

<210> SEQ ID NO 68
<211> LENGTH: 551
<212> TYPE: DNA
<213> ORGANISM: Homo sapiens
<220> FEATURE:
<221> NAME/KEY: modified_base
<222> LOCATION: (286)
<223> OTHER INFORMATION: Where n is a, c, g or t
<221> NAME/KEY: modified_base
<222> LOCATION: (464)
<223> OTHER INFORMATION: Where n is a, c, g or t
<221> NAME/KEY: modified_base
<222> LOCATION: (480)
<223> OTHER INFORMATION: Where n is a, c, g or t
<221> NAME/KEY: modified_base
<222> LOCATION: (501)
<223> OTHER INFORMATION: Where n is a, c, g or t
<221> NAME/KEY: modified_base
<222> LOCATION: (502)
<223> OTHER INFORMATION: Where n is a, c, g or t
<221> NAME/KEY: modified_base
<222> LOCATION: (518)
<223> OTHER INFORMATION: Where n is a, c, g or t
<221> NAME/KEY: modified_base
<222> LOCATION: (528)
<223> OTHER INFORMATION: Where n is a, c, g or t
<221> NAME/KEY: modified_base
<222> LOCATION: (533)
<223> OTHER INFORMATION: Where n is a, c, g or t
<221> NAME/KEY: modified_base
<222> LOCATION: (536)
<223> OTHER INFORMATION: Where n is a, c, g or t
<221> NAME/KEY: modified_base
<222> LOCATION: (537)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (539)
<223> OTHER INFORMATION: Where n is a, c, g or t
<221> NAME/KEY: modified_base
<222> LOCATION: (540)
<223> OTHER INFORMATION: Where n is a, c, g or t

```
<221> NAME/KEY: modified_base
<222> LOCATION: (541)
<223> OTHER INFORMATION: Where n is a, c, g or t
<221> NAME/KEY: modified_base
<222> LOCATION: (543)
<223> OTHER INFORMATION: Where n is a, c, g or t
<221> NAME/KEY: modified_base
<222> LOCATION: (544)
<223> OTHER INFORMATION: Where n is a, c, g or t
<221> NAME/KEY: modified_base
<222> LOCATION: (545)
<223> OTHER INFORMATION: Where n is a, c, g or t
<221> NAME/KEY: modified_base
<222> LOCATION: (547)
<223> OTHER INFORMATION: Where n is a, c, g or t
<221> NAME/KEY: modified_base
<222> LOCATION: (548)
<223> OTHER INFORMATION: Where n is a, c, g or t
<221> NAME/KEY: modified_base
<222> LOCATION: (549)
<223> OTHER INFORMATION: Where n is a, c, g or t

<400> SEQUENCE: 68
actagtagct ggtacataat cactgaggag ctatttctta acatgctttt atagaccatg      60
ctaatgctag accagtattt aagggctaat ctcacacctc cttagctgta agagtctggc     120
ttagaacaga cctctctgtg caataacttg tggccactgg aaatccctgg gccggcattt     180
gtattggggt tgcaatgact cccaagggcc aaaagagtta aaggcacgac tgggatttct     240
tctgagactg tggtgaaact ccttccaagg ctgaggggt cagtangtgc tctgggaggg      300
actcggcacc actttgatat tcaacaagcc acttgaagcc caattataaa attgttattt     360
tacagctgat ggaactcaat ttgaaccttc aaaactttgt tagtttatcc tattatattg     420
ttaaacctaa ttcatttgt ctagcattgg atttggttcc tgtngcatat gttttttcn      480 cctatgtgct cccctccccc nnatcttaat ttaaaccnca attttgcnat tcnccnnnnn    540
nannnannna a                                                          551

<210> SEQ ID NO 69
<211> LENGTH: 396
<212> TYPE: DNA
<213> ORGANISM: Homo sapiens
<220> FEATURE:
<221> NAME/KEY: modified_base
<222> LOCATION: (255)
<223> OTHER INFORMATION: Where n is a, c, g or t
<221> NAME/KEY: modified_base
<222> LOCATION: (310)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (381)
<223> OTHER INFORMATION: Where n is a, c, g or t

<400> SEQUENCE: 69
cagaaatgga aagcagagtt ttcatttctg tttataaacg tctccaaaca aaatggaaa       60 gcagagtttt cattaaatcc ttttaccttt ttttttctt ggtaatcccc tcaaataaca     120
gtatgtggga tattgaatgt taagggata ttttttcta ttattttat aattgtacaa       180 aattaagcaa atgttaaaag ttttatatgc tttattaatg tttcaaaag gtatnataca     240 tgtgatacat tttttaagct tcagttgctt gtcttctggt actttctgtt atgggctttt    300
ggggagccan aaaccaatct acnatctctt tttgtttgcc aggacatgca ataaaattta    360
aaaaataaat aaaaactatt nagaaattga aaaaaa                              396
```

<210> SEQ ID NO 70
<211> LENGTH: 536
<212> TYPE: DNA
<213> ORGANISM: Homo sapiens
<220> FEATURE:
<221> NAME/KEY: modified_base
<222> LOCATION: (388)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (455)
<223> OTHER INFORMATION: Where n is a, c, g or t

<400> SEQUENCE: 70

```
actagtgcaa aagcaaatat aaacatcgaa aaggcgttcc tcacgttagc tgaagatatc      60
cttcgaaaga cccctgtaaa agagcccaac agtgaaaatg tagatatcag cagtggagga     120
ggcgtgacag gctggaagag caaatgctgc tgagcattct cctgttccat cagttgccat     180
ccactacccc gttttctctt cttgctgcaa aataaaccac tctgtccatt tttaactcta     240
aacagatatt tttgtttctc atcttaacta tccaagccac ctatttatt tgttctttca      300
tctgtgactg cttgctgact ttatcataat tttcttcaaa caaaaaatg tatagaaaaa      360
tcatgtctgt gacttcattt ttaaatgnta cttgctcagc tcaactgcat ttcagttgtt     420
ttatagtcca gttcttatca acattnaaac ctatngcaat catttcaaat ctattctgca     480
aattgtataa gaataaaagt tagaatttaa caattaaaaa aaaaaaaaa aaaaaa          536
```

<210> SEQ ID NO 71
<211> LENGTH: 865
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<221> NAME/KEY: modified_base
<222> LOCATION: (35)
<223> OTHER INFORMATION: Where n is a, c, g or t
<221> NAME/KEY: modified_base
<222> LOCATION: (39)
<223> OTHER INFORMATION: Where n is a, c, g or t
<221> NAME/KEY: modified_base
<222> LOCATION: (56)
<223> OTHER INFORMATION: Where n is a, c, g or t
<221> NAME/KEY: modified_base
<222> LOCATION: (131)
<223> OTHER INFORMATION: Where n is a, c, g or t
<221> NAME/KEY: modified_base
<222> LOCATION: (138)
<223> OTHER INFORMATION: Where n is a, c, g or t
<221> NAME/KEY: modified_base
<222> LOCATION: (146)
<223> OTHER INFORMATION: Where n is a, c, g or t
<221> NAME/KEY: modified_base
<222> LOCATION: (183)
<223> OTHER INFORMATION: Where n is a, c, g or t
<221> NAME/KEY: modified_base
<222> LOCATION: (194)
<223> OTHER INFORMATION: Where n is a, c, g or t
<221> NAME/KEY: modified_base
<222> LOCATION: (197)
<223> OTHER INFORMATION: Where n is a, c, g or t
<221> NAME/KEY: modified_base
<222> LOCATION: (238)
<223> OTHER INFORMATION: Where n is a, c, g or t
<221> NAME/KEY: modified_base
<222> LOCATION: (269)
<223> OTHER INFORMATION: Where n is a, c, g or t
<221> NAME/KEY: modified_base -continued

```
<222> LOCATION: (277)
<223> OTHER INFORMATION: Where n is a, c, g or t
<221> NAME/KEY: modified_base
<222> LOCATION: (282)
<223> OTHER INFORMATION: Where n is a, c, g or t
<221> NAME/KEY: modified_base
<222> LOCATION: (297)
<223> OTHER INFORMATION: Where n is a, c, g or t
<221> NAME/KEY: modified_base
<222> LOCATION: (316)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (336)
<223> OTHER INFORMATION: Where n is a, c, g or t
<221> NAME/KEY: modified_base
<222> LOCATION: (340)
<223> OTHER INFORMATION: Where n is a, c, g or t
<221> NAME/KEY: modified_base
<222> LOCATION: (341)
<223> OTHER INFORMATION: Where n is a, c, g or t
<221> NAME/KEY: modified_base
<222> LOCATION: (346)
<223> OTHER INFORMATION: Where n is a, c, g or t
<221> NAME/KEY: modified_base
<222> LOCATION: (349)
<223> OTHER INFORMATION: Where n is a, c, g or t
<221> NAME/KEY: modified_base
<222> LOCATION: (370)
<223> OTHER INFORMATION: Where n is a, c, g or t
<221> NAME/KEY: modified_base
<222> LOCATION: (376)
<223> OTHER INFORMATION: Where n is a, c, g or t
<221> NAME/KEY: modified_base
<222> LOCATION: (381)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (392)
<223> OTHER INFORMATION: Where n is a, c, g or t
<221> NAME/KEY: modified_base
<222> LOCATION: (396)
<223> OTHER INFORMATION: Where n is a, c, g or t
<221> NAME/KEY: modified_base
<222> LOCATION: (397)
<223> OTHER INFORMATION: Where n is a, c, g or t
<221> NAME/KEY: modified_base
<222> LOCATION: (401)
<223> OTHER INFORMATION: Where n is a, c, g or t
<221> NAME/KEY: modified_base
<222> LOCATION: (433)
<223> OTHER INFORMATION: Where n is a, c, g or t
<221> NAME/KEY: modified_base
<222> LOCATION: (444)
<223> OTHER INFORMATION: Where n is a, c, g or t
<221> NAME/KEY: modified_base
<222> LOCATION: (445)
<223> OTHER INFORMATION: Where n is a, c, g or t
<221> NAME/KEY: modified_base
<222> LOCATION: (454)
<223> OTHER INFORMATION: Where n is a, c, g or t
<221> NAME/KEY: modified_base
<222> LOCATION: (455)
<223> OTHER INFORMATION: Where n is a, c, g or t
<221> NAME/KEY: modified_base
<222> LOCATION: (469)
<223> OTHER INFORMATION: Where n is a, c, g or t
<221> NAME/KEY: modified_base
<222> LOCATION: (472)
<223> OTHER INFORMATION: Where n is a, c, g or t
<221> NAME/KEY: modified_base
<222> LOCATION: (477)
<223> OTHER INFORMATION: Where n is a, c, g or t
<221> NAME/KEY: modified_base
<222> LOCATION: (480)
```

-continued

```
<223> OTHER INFORMATION: Where n is a, c, g or t
<221> NAME/KEY: modified_base
<222> LOCATION: (482)
<223> OTHER INFORMATION: Where n is a, c, g or t
<221> NAME/KEY: modified_base
<222> LOCATION: (489)
<223> OTHER INFORMATION: Where n is a, c, g or t
<221> NAME/KEY: modified_base
<222> LOCATION: (497)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (526)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (545)
<223> OTHER INFORMATION: Where n is a, c, g or t
<221> NAME/KEY: modified_base
<222> LOCATION: (553)
<223> OTHER INFORMATION: Where n is a, c, g or t
<221> NAME/KEY: modified_base
<222> LOCATION: (556)
<223> OTHER INFORMATION: Where n is a, c, g or t
<221> NAME/KEY: modified_base
<222> LOCATION: (567)
<223> OTHER INFORMATION: Where n is a, c, g or t
<221> NAME/KEY: modified_base
<222> LOCATION: (574)
<223> OTHER INFORMATION: Where n is a, c, g or t
<221> NAME/KEY: modified_base
<222> LOCATION: (580)
<223> OTHER INFORMATION: Where n is a, c, g or t
<221> NAME/KEY: modified_base
<222> LOCATION: (610)
<223> OTHER INFORMATION: Where n is a, c, g or t
<221> NAME/KEY: modified_base
<222> LOCATION: (613)
<223> OTHER INFORMATION: Where n is a, c, g or t
<221> NAME/KEY: modified_base
<222> LOCATION: (634)
<223> OTHER INFORMATION: Where n is a, c, g or t
<221> NAME/KEY: modified_base
<222> LOCATION: (638)
<223> OTHER INFORMATION: Where n is a, c, g or t
<221> NAME/KEY: modified_base
<222> LOCATION: (639)
<223> OTHER INFORMATION: Where n is a, c, g or t
<221> NAME/KEY: modified_base
<222> LOCATION: (663)
<223> OTHER INFORMATION: Where n is a, c, g or t
<221> NAME/KEY: modified_base
<222> LOCATION: (672)
<223> OTHER INFORMATION: Where n is a, c, g or t
<221> NAME/KEY: modified_base
<222> LOCATION: (689)
<223> OTHER INFORMATION: Where n is a, c, g or t
<221> NAME/KEY: modified_base
<222> LOCATION: (693)
<223> OTHER INFORMATION: Where n is a, c, g or t
<221> NAME/KEY: modified_base
<222> LOCATION: (694)
<223> OTHER INFORMATION: Where n is a, c, g or t
<221> NAME/KEY: modified_base
<222> LOCATION: (701)
<223> OTHER INFORMATION: Where n is a, c, g or t
<221> NAME/KEY: modified_base
<222> LOCATION: (704)
<223> OTHER INFORMATION: Where n is a, c, g or t
```

-continued

```
<221> NAME/KEY: modified_base
<222> LOCATION: (713)
<223> OTHER INFORMATION: Where n is a, c, g or t
<221> NAME/KEY: modified_base
<222> LOCATION: (723)
<223> OTHER INFORMATION: Where n is a, c, g or t
<221> NAME/KEY: modified_base
<222> LOCATION: (729)
<223> OTHER INFORMATION: Where n is a, c, g or t
<221> NAME/KEY: modified_base
<222> LOCATION: (732)
<223> OTHER INFORMATION: Where n is a, c, g or t
<221> NAME/KEY: modified_base
<222> LOCATION: (743)
<223> OTHER INFORMATION: Where n is a, c, g or t
<221> NAME/KEY: modified_base
<222> LOCATION: (744)
<223> OTHER INFORMATION: Where n is a, c, g or t
<221> NAME/KEY: modified_base
<222> LOCATION: (749)
<223> OTHER INFORMATION: Where n is a, c, g or t
<221> NAME/KEY: modified_base
<222> LOCATION: (761)
<223> OTHER INFORMATION: Where n is a, c, g or t
<221> NAME/KEY: modified_base
<222> LOCATION: (765)
<223> OTHER INFORMATION: Where n is a, c, g or t
<221> NAME/KEY: modified_base
<222> LOCATION: (767)
<223> OTHER INFORMATION: Where n is a, c, g or t
<221> NAME/KEY: modified_base
<222> LOCATION: (769)
<223> OTHER INFORMATION: Where n is a, c, g or t
<221> NAME/KEY: modified_base
<222> LOCATION: (772)
<223> OTHER INFORMATION: Where n is a, c, g or t
<221> NAME/KEY: modified_base
<222> LOCATION: (774)
<223> OTHER INFORMATION: Where n is a, c, g or t
<221> NAME/KEY: modified_base
<222> LOCATION: (780)
<223> OTHER INFORMATION: Where n is a, c, g or t
<221> NAME/KEY: modified_base
<222> LOCATION: (783)
<223> OTHER INFORMATION: Where n is a, c, g or t
<221> NAME/KEY: modified_base
<222> LOCATION: (788)
<223> OTHER INFORMATION: Where n is a, c, g or t
<221> NAME/KEY: modified_base
<222> LOCATION: (792)
<223> OTHER INFORMATION: Where n is a, c, g or t
<221> NAME/KEY: modified_base
<222> LOCATION: (803)
<223> OTHER INFORMATION: Where n is a, c, g or t
<221> NAME/KEY: modified_base
<222> LOCATION: (810)
<223> OTHER INFORMATION: Where n is a, c, g or t
<221> NAME/KEY: modified_base
<222> LOCATION: (824)
<223> OTHER INFORMATION: Where n is a, c, g or t
<221> NAME/KEY: modified_base
<222> LOCATION: (840)
<223> OTHER INFORMATION: Where n is a, c, g or t
<221> NAME/KEY: modified_base
<222> LOCATION: (848)
<223> OTHER INFORMATION: Where n is a, c, g or t

<400> SEQUENCE: 71
gacaaagcgt taggagaaga anagaggcag ggaanactnc ccaggcacga tggccncctt     60
cccaccagca accagcgccc cccaccagcc cccaggcccg gacgacgaag actccatcct    120
ggattaatct nacctctntc gcctgnccca ttcctacctc ggaggtggag gccggaaagg    180
tcncaccaag aganaanctg ctgccaacac caaccgcccc agccctggcg ggcacganag    240
gaaactggtg accaatctgc agaattctna gaggaanaag cnaggggccc cgcgctnaga    300
```

-continued

```
cagagctgga tatgangcca gaccatggac nctacncccn ncaatncana cgggactgcg    360
gaagatggan gacccncgac nngatcaggc cngctnncca nccccccacc cctatgaatt    420
attcccgctg aangaatctc tganngctt ccannaaagc gcctcccnc cnaacgnaan     480 tncaacatng ggattanang ctgggaactg naaggggcaa ancctnnaat atccccagaa    540
acaanctctc ccnaanaaac tgggcncct catngtggn accaactatt aactaaaccg     600
cacgccaagn aantataaaa gggggcccc tccnggnng acccccttttt gtcccttaat    660 ganggttatc cnccttgcgt accatggtnc ccnnttctgt ntgnatgttt ccnctcccct   720
ccncctatnt cnagccgaac tcnnatttnc ccggggtgc natcnantng tncnccttn    780 ttngttgncc cngcccttc cgncggaacn cgtttccccg ttantaacgg cacccggggn    840
aagggtgntt ggcccctcc ctccc                                         865
```

```
<210> SEQ ID NO 72
<211> LENGTH: 560
<212> TYPE: DNA
<213> ORGANISM: Homo sapiens
<220> FEATURE:
<221> NAME/KEY: modified_base
<222> LOCATION: (83)
<223> OTHER INFORMATION: Where n is a, c, g or t
<221> NAME/KEY: modified_base
<222> LOCATION: (173)
<223> OTHER INFORMATION: Where n is a, c, g or t
<221> NAME/KEY: modified_base
<222> LOCATION: (183)
<223> OTHER INFORMATION: Where n is a, c, g or t
<221> NAME/KEY: modified_base
<222> LOCATION: (186)
<223> OTHER INFORMATION: Where n is a, c, g or t
<221> NAME/KEY: modified_base
<222> LOCATION: (209)
<223> OTHER INFORMATION: Where n is a, c, g or t
<221> NAME/KEY: modified_base
<222> LOCATION: (211)
<223> OTHER INFORMATION: Where n is a, c, g or t
<221> NAME/KEY: modified_base
<222> LOCATION: (215)
<223> OTHER INFORMATION: Where n is a, c, g or t
<221> NAME/KEY: modified_base
<222> LOCATION: (255)
<223> OTHER INFORMATION: Where n is a, c, g or t
<221> NAME/KEY: modified_base
<222> LOCATION: (321)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (323)
<223> OTHER INFORMATION: Where n is a, c, g or t
<221> NAME/KEY: modified_base
<222> LOCATION: (335)
<223> OTHER INFORMATION: Where n is a, c, g or t
<221> NAME/KEY: modified_base
<222> LOCATION: (344)
<223> OTHER INFORMATION: Where n is a, c, g or t
<221> NAME/KEY: modified_base
<222> LOCATION: (357)
<223> OTHER INFORMATION: Where n is a, c, g or t
<221> NAME/KEY: modified_base
<222> LOCATION: (361)
<223> OTHER INFORMATION: Where n is a, c, g or t
<221> NAME/KEY: modified_base
<222> LOCATION: (368)
<223> OTHER INFORMATION: Where n is a, c, g or t
<221> NAME/KEY: modified_base
<222> LOCATION: (394)
<223> OTHER INFORMATION: Where n is a, c, g or t
<221> NAME/KEY: modified_base
<222> LOCATION: (412)
```

```
<223> OTHER INFORMATION: Where n is a, c, g or t
<221> NAME/KEY: modified_base
<222> LOCATION: (415)
<223> OTHER INFORMATION: Where n is a, c, g or t
<221> NAME/KEY: modified_base
<222> LOCATION: (442)
<223> OTHER INFORMATION: Where n is a, c, g or t
<221> NAME/KEY: modified_base
<222> LOCATION: (455)
<223> OTHER INFORMATION: Where n is a, c, g or t
<221> NAME/KEY: modified_base
<222> LOCATION: (469)
<223> OTHER INFORMATION: Where n is a, c, g or t
<221> NAME/KEY: modified_base
<222> LOCATION: (472)
<223> OTHER INFORMATION: Where n is a, c, g or t
<221> NAME/KEY: modified_base
<222> LOCATION: (475)
<223> OTHER INFORMATION: Where n is a, c, g or t
<221> NAME/KEY: modified_base
<222> LOCATION: (487)
<223> OTHER INFORMATION: Where n is a, c, g or t
<221> NAME/KEY: modified_base
<222> LOCATION: (513)
<223> OTHER INFORMATION: Where n is a, c, g or t
<221> NAME/KEY: modified_base
<222> LOCATION: (522)
<223> OTHER INFORMATION: Where n is a, c, g or t
<221> NAME/KEY: modified_base
<222> LOCATION: (528)
<223> OTHER INFORMATION: Where n is a, c, g or t
<221> NAME/KEY: modified_base
<222> LOCATION: (531)
<223> OTHER INFORMATION: Where n is a, c, g or t
<221> NAME/KEY: modified_base
<222> LOCATION: (534)
<223> OTHER INFORMATION: Where n is a, c, g or t
<221> NAME/KEY: modified_base
<222> LOCATION: (546)
<223> OTHER INFORMATION: Where n is a, c, g or t

<400> SEQUENCE: 72
cctggacttg tcttggttcc agaacctgac gacccggcga cggcgacgtc tcttttgact      60
aaaagacagt gtccagtgct ccngcctagg agtctacggg gaccgcctcc cgcgccgcca     120
ccatgcccaa cttctctggc aactggaaaa tcatccgatc ggaaaacttc gangaattgc     180
tcnaantgct gggggtgaat gtgatgctna ngaanattgc tgtggctgca gcgtccaagc     240
cagcagtgga gatcnaacag gagggagaca ctttctacat caaaacctcc accaccgtgc     300
gcaccacaaa gattaacttc nnngttgggg agganttga ggancaaact gtggatggga      360
ngcctgtnaa aacctggtga aatgggagaa tganaataaa atggtctgtg ancanaaact     420
cctgaaagga gaaggccccc anaactcctg gaccngaaaa actgacccnc cnatnggga      480 actgatnctt gaaccctgaa cggcgggat gancctttt tnttgccnc naangggttc        540 tttccntttc cccaaaaaaa                                                 560

<210> SEQ ID NO 73
<211> LENGTH: 379
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (17)
<223> OTHER INFORMATION: Where n is a, c, g or t
<221> NAME/KEY: modified_base
<222> LOCATION: (18)
<223> OTHER INFORMATION: Where n is a, c, g or t
<221> NAME/KEY: modified_base
```

-continued

```
<222> LOCATION: (21)
<223> OTHER INFORMATION: Where n is a, c, g or t
<221> NAME/KEY: modified_base
<222> LOCATION: (26)
<223> OTHER INFORMATION: Where n is a, c, g or t
<221> NAME/KEY: modified_base
<222> LOCATION: (29)
<223> OTHER INFORMATION: Where n is a, c, g or t
<221> NAME/KEY: modified_base
<222> LOCATION: (30)
<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (53)
<223> OTHER INFORMATION: Where n is a, c, g or t
<221> NAME/KEY: modified_base
<222> LOCATION: (56)
<223> OTHER INFORMATION: Where n is a, c, g or t
<221> NAME/KEY: modified_base
<222> LOCATION: (67)
<223> OTHER INFORMATION: Where n is a, c, g or t
<221> NAME/KEY: modified_base
<222> LOCATION: (71)
<223> OTHER INFORMATION: Where n is a, c, g or t
<221> NAME/KEY: modified_base
<222> LOCATION: (81)
<223> OTHER INFORMATION: Where n is a, c, g or t
<221> NAME/KEY: modified_base
<222> LOCATION: (102)
<223> OTHER INFORMATION: Where n is a, c, g or t
<221> NAME/KEY: modified_base
<222> LOCATION: (104)
<223> OTHER INFORMATION: Where n is a, c, g or t
<221> NAME/KEY: modified_base
<222> LOCATION: (111)
<223> OTHER INFORMATION: Where n is a, c, g or t
<221> NAME/KEY: modified_base
<222> LOCATION: (112)
<223> OTHER INFORMATION: Where n is a, c, g or t
<221> NAME/KEY: modified_base
<222> LOCATION: (114)
<223> OTHER INFORMATION: Where n is a, c, g or t
<221> NAME/KEY: modified_base
<222> LOCATION: (119)
<223> OTHER INFORMATION: Where n is a, c, g or t
<221> NAME/KEY: modified_base
<222> LOCATION: (122)
<223> OTHER INFORMATION: Where n is a, c, g or t
<221> NAME/KEY: modified_base
<222> LOCATION: (124)
<223> OTHER INFORMATION: Where n is a, c, g or t
<221> NAME/KEY: modified_base
<222> LOCATION: (125)
<223> OTHER INFORMATION: Where n is a, c, g or t
<221> NAME/KEY: modified_base
<222> LOCATION: (134)
<223> OTHER INFORMATION: Where n is a, c, g or t
<221> NAME/KEY: modified_base
<222> LOCATION: (144)
<223> OTHER INFORMATION: Where n is a, c, g or t
<221> NAME/KEY: modified_base
<222> LOCATION: (146)
<223> OTHER INFORMATION: Where n is a, c, g or t
<221> NAME/KEY: modified_base
<222> LOCATION: (189)
<223> OTHER INFORMATION: Where n is a, c, g or t
<221> NAME/KEY: modified_base
<222> LOCATION: (190)
<223> OTHER INFORMATION: Where n is a, c, g or t
<221> NAME/KEY: modified_base
<222> LOCATION: (214)
<223> OTHER INFORMATION: Where n is a, c, g or t
<221> NAME/KEY: modified_base
<222> LOCATION: (215)
<223> OTHER INFORMATION: Where n is a, c, g or t
<221> NAME/KEY: modified_base
<222> LOCATION: (219)
```

```
<223> OTHER INFORMATION: Where n is a, c, g or t
<221> NAME/KEY: modified_base
<222> LOCATION: (222)
<223> OTHER INFORMATION: Where n is a, c, g or t
<221> NAME/KEY: modified_base
<222> LOCATION: (235)
<223> OTHER INFORMATION: Where n is a, c, g or t
<221> NAME/KEY: modified_base
<222> LOCATION: (237)
<223> OTHER INFORMATION: Where n is a, c, g or t
<221> NAME/KEY: modified_base
<222> LOCATION: (246)
<223> OTHER INFORMATION: Where n is a, c, g or t
<221> NAME/KEY: modified_base
<222> LOCATION: (280)
<223> OTHER INFORMATION: Where n is a, c, g or t
<221> NAME/KEY: modified_base
<222> LOCATION: (288)
<223> OTHER INFORMATION: Where n is a, c, g or t
<221> NAME/KEY: modified_base
<222> LOCATION: (302)
<223> OTHER INFORMATION: Where n is a, c, g or t
<221> NAME/KEY: modified_base
<222> LOCATION: (310)
<223> OTHER INFORMATION: Where n is a, c, g or t
<221> NAME/KEY: modified_base
<222> LOCATION: (313)
<223> OTHER INFORMATION: Where n is a, c, g or t
<221> NAME/KEY: modified_base
<222> LOCATION: (319)
<223> OTHER INFORMATION: Where n is a, c, g or t
<221> NAME/KEY: modified_base
<222> LOCATION: (322)
<223> OTHER INFORMATION: Where n is a, c, g or t
<221> NAME/KEY: modified_base
<222> LOCATION: (343)
<223> OTHER INFORMATION: Where n is a, c, g or t
<221> NAME/KEY: modified_base
<222> LOCATION: (353)
<223> OTHER INFORMATION: Where n is a, c, g or t
<221> NAME/KEY: modified_base
<222> LOCATION: (354)
<223> OTHER INFORMATION: Where n is a, c, g or t

<400> SEQUENCE: 73
ctggggancc ggcggtnngc nccatntcnn gncgcgaagg tggcaataaa aanccnctga      60
aaccgcncaa naaacatgcc naagatatgg acgaggaaga tngngctttc nngnacaanc    120
gnanngagga acanaacaaa ctcnangagc tctcaagcta atgccgcggg gaaggggccc    180
ttggccacnn gtggaattaa gaaatctggc aaanngtann tgttccttgt gcctnangag    240
ataagngacc cttttatttca tctgtattta aacctctctn ttccctgnca taacttcttt    300
tnccacgtan agntggaant anttgttgtc ttggactgtt gtncatttta gannaaactt    360
ttgttcaaaa aaaaaataa                                                 379

<210> SEQ ID NO 74
<211> LENGTH: 437
<212> TYPE: DNA
<213> ORGANISM: Homo sapiens
<220> FEATURE:
<221> NAME/KEY: modified_base
<222> LOCATION: (145)
<223> OTHER INFORMATION: Where n is a, c, g or t
<221> NAME/KEY: modified_base
<222> LOCATION: (355)
<223> OTHER INFORMATION: Where n is a, c, g or t

<400> SEQUENCE: 74
actagttcag actgccacgc caaccccaga aaatacccca catgccagaa aagtgaagtc     60
ctaggtgttt ccatctatgt ttcaatctgt ccatctacca ggcctcgcga taaaaacaaa   120
```

| | | |
|---|---|---|
| acaaaaaaac gctgccaggt tttanaagca gttctggtct caaaaccatc aggatcctgc | 180 | |
| caccagggtt cttttgaaat agtaccacat gtaaaaggga atttggcttt cacttcatct | 240 | |
| aatcactgaa ttgtcaggct ttgattgata attgtagaaa taagtagcct tctgttgtgg | 300 | |
| gaataagtta taatcagtat tcatctcttt gttttttgtc actcttttct ctctnattgt | 360 | |
| gtcatttgta ctgtttgaaa aatatttctt ctataaaatt aaactaacct gccttaaaaa | 420 | |
| aaaaaaaaaa aaaaaaa | 437 | |

```
<210> SEQ ID NO 75
<211> LENGTH: 579
<212> TYPE: DNA
<213> ORGANISM: Homo sapiens
<220> FEATURE:
<221> NAME/KEY: modified_base
<222> LOCATION: (440)
<223> OTHER INFORMATION: Where n is a, c, g or t
<221> NAME/KEY: modified_base
<222> LOCATION: (513)
<223> OTHER INFORMATION: Where n is a, c, g or t
<221> NAME/KEY: modified_base
<222> LOCATION: (539)
<223> OTHER INFORMATION: Where n is a, c, g or t
<221> NAME/KEY: modified_base
<222> LOCATION: (551)
<223> OTHER INFORMATION: Where n is a, c, g or t

<400> SEQUENCE: 75
```

| | | |
|---|---|---|
| ctccgtcgcc gccaagatga tgtgcgggc gccctccgcc acgcagccgg ccaccgccga | 60 | |
| gacccagcac atcgccgacc aggtgaggtc ccagcttgaa gagaaagaaa acaagaagtt | 120 | |
| ccctgtgttt aaggccgtgt cattcaagag ccaggtggtc gcggggacaa actacttcat | 180 | |
| caaggtgcac gtcggcgacg aggacttcgt acacctgcga gtgttccaat ctctccctca | 240 | |
| tgaaaacaag cccttgacct tatctaacta ccagaccaac aaagccaagc atgatgagct | 300 | |
| gacctatttc tgatcctgac tttggacaag gcccttcagc cagaagactg acaaagtcat | 360 | |
| cctccgtcta ccagagcgtg cacttgtgat cctaaaataa gcttcatctc cgggctgtgc | 420 | |
| ccttggggtg aaggggcan gatctgcact gcttttgcat ttctcttcct aaatttcatt | 480 | |
| gtgttgattc tttccttcca ataggtgatc ttnattactt tcagaatatt ttccaaatna | 540 | |
| gatatatttt naaaatcctt aaaaaaaaaa aaaaaaaa | 579 | |

```
<210> SEQ ID NO 76
<211> LENGTH: 666
<212> TYPE: DNA
<213> ORGANISM: Homo sapiens
<220> FEATURE:
<221> NAME/KEY: modified_base
<222> LOCATION: (411)
<223> OTHER INFORMATION: Where n is a, c, g or t
<221> NAME/KEY: modified_base
<222> LOCATION: (470)
<223> OTHER INFORMATION: Where n is a, c, g or t
<221> NAME/KEY: modified_base
<222> LOCATION: (476)
<223> OTHER INFORMATION: Where n is a, c, g or t
<221> NAME/KEY: modified_base
<222> LOCATION: (491)
<223> OTHER INFORMATION: Where n is a, c, g or t
<221> NAME/KEY: modified_base
<222> LOCATION: (506)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (560)
```

<223> OTHER INFORMATION: Where n is a, c, g or t
<221> NAME/KEY: modified_base
<222> LOCATION: (570)
<223> OTHER INFORMATION: Where n is a, c, g or t
<221> NAME/KEY: modified_base
<222> LOCATION: (632)
<223> OTHER INFORMATION: Where n is a, c, g or t
<221> NAME/KEY: modified_base
<222> LOCATION: (636)
<223> OTHER INFORMATION: Where n is a, c, g or t
<221> NAME/KEY: modified_base
<222> LOCATION: (643)
<223> OTHER INFORMATION: Where n is a, c, g or t
<221> NAME/KEY: modified_base
<222> LOCATION: (650)
<223> OTHER INFORMATION: Where n is a, c, g or t
<221> NAME/KEY: modified_base
<222> LOCATION: (654)
<223> OTHER INFORMATION: Where n is a, c, g or t
<221> NAME/KEY: modified_base
<222> LOCATION: (658)
<223> OTHER INFORMATION: Where n is a, c, g or t

<400> SEQUENCE: 76

```
gtttatccta tctctccaac cagattgtca gctccttgag ggcaagagcc acagtatatt     60
tccctgtttc ttccacagtg cctaataata ctgtggaact aggttttaat aattttttaa    120
ttgatgttgt tatgggcagg atggcaacca gaccattgtc tcagagcagg tgctggctct    180
ttcctggcta ctccatgttg gctagcctct ggtaacctct tacttattat cttcaggaca    240
ctcactacag ggaccaggga tgatgcaaca tccttgtctt tttatgacag gatgtttgct    300
cagcttctcc aacaataaaa agcacgtggt aaaacacttg cggatattct ggactgtttt    360
taaaaaatat acagtttacc gaaaatcata ttatcttaca atgaaaagga ntttatagat    420
cagccagtga acaaccttt ccaccatac aaaaattcct tttcccgaan gaaaanggct      480
ttctcaataa nnctcacttt cttaanatct tacaagatag ccccganatc ttatcgaaac    540
tcattttagg caaatatgan ttttattgtn cgttacttgt ttcaaaattt ggtattgtga    600
atatcaatta ccacccccat ctcccatgaa anaaanggga aanggtgaan ttcntaancg    660
cttaaa                                                              666
```

<210> SEQ ID NO 77
<211> LENGTH: 396
<212> TYPE: DNA
<213> ORGANISM: Homo sapiens
<220> FEATURE:
<221> NAME/KEY: modified_base
<222> LOCATION: (31)
<223> OTHER INFORMATION: Where n is a, c, g or t
<221> NAME/KEY: modified_base
<222> LOCATION: (54)
<223> OTHER INFORMATION: Where n is a, c, g or t
<221> NAME/KEY: modified_base
<222> LOCATION: (125)
<223> OTHER INFORMATION: Where n is a, c, g or t
<221> NAME/KEY: modified_base
<222> LOCATION: (128)
<223> OTHER INFORMATION: Where n is a, c, g or t
<221> NAME/KEY: modified_base
<222> LOCATION: (136)
<223> OTHER INFORMATION: Where n is a, c, g or t
<221> NAME/KEY: modified_base
<222> LOCATION: (163)
<223> OTHER INFORMATION: Where n is a, c, g or t
<221> NAME/KEY: modified_base
<222> LOCATION: (168)
<223> OTHER INFORMATION: Where n is a, c, g or t
<221> NAME/KEY: modified_base
<222> LOCATION: (198)
<223> OTHER INFORMATION: Where n is a, c, g or t

<400> SEQUENCE: 77

```
ctgcagcccg ggggatccac taatctacca nggttatttg gcagctaatt ctanatttgg      60
atcattgccc aaagttgcac ttgctggtct cttgggattt ggccttggaa aggtatcata     120
catanganta tgccanaata aattccattt ttttgaaaat canctccntg gggctggttt     180
tggtccacag cataacangc actgcctcct tacctgtgag gaatgcaaaa taaagcatgg     240
attaagtgag aagggagact ctcagccttc agcttcctaa attctgtgtc tgtgactttc     300
gaagttttt aaacctctga atttgtacac atttaaaatt tcaagtgtac tttaaaataa      360
aatacttcta atgggaacaa aaaaaaaaaa aaaaaa                               396
```

<210> SEQ ID NO 78
<211> LENGTH: 793
<212> TYPE: DNA
<213> ORGANISM: Homo sapiens
<220> FEATURE:
<221> NAME/KEY: modified_base
<222> LOCATION: (309)
<223> OTHER INFORMATION: Where n is a, c, g or t
<221> NAME/KEY: modified_base
<222> LOCATION: (492)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (657)
<223> OTHER INFORMATION: Where n is a, c, g or t
<221> NAME/KEY: modified_base
<222> LOCATION: (660)
<223> OTHER INFORMATION: Where n is a, c, g or t
<221> NAME/KEY: modified_base
<222> LOCATION: (703)
<223> OTHER INFORMATION: Where n is a, c, g or t
<221> NAME/KEY: modified_base
<222> LOCATION: (708)
<223> OTHER INFORMATION: Where n is a, c, g or t
<221> NAME/KEY: modified_base
<222> LOCATION: (710)
<223> OTHER INFORMATION: Where n is a, c, g or t
<221> NAME/KEY: modified_base
<222> LOCATION: (711)
<223> OTHER INFORMATION: Where n is a, c, g or t
<221> NAME/KEY: modified_base
<222> LOCATION: (732)
<223> OTHER INFORMATION: Where n is a, c, g or t
<221> NAME/KEY: modified_base
<222> LOCATION: (740)
<223> OTHER INFORMATION: Where n is a, c, g or t
<221> NAME/KEY: modified_base
<222> LOCATION: (748)
<223> OTHER INFORMATION: Where n is a, c, g or t
<221> NAME/KEY: modified_base
<222> LOCATION: (758)
<223> OTHER INFORMATION: Where n is a, c, g or t
<221> NAME/KEY: modified_base
<222> LOCATION: (762)
<223> OTHER INFORMATION: Where n is a, c, g or t
<221> NAME/KEY: modified_base
<222> LOCATION: (765)
<223> OTHER INFORMATION: Where n is a, c, g or t
<221> NAME/KEY: modified_base
<222> LOCATION: (787)
<223> OTHER INFORMATION: Where n is a, c, g or t

<400> SEQUENCE: 78

```
gcatcctagc cgccgactca cacaaggcag gtgggtgagg aaatccagag ttgccatgga      60
gaaaattcca gtgtcagcat tcttgctcct tgtggccctc tcctacactc tggcagaga     120
taccacagtc aaacctggag ccaaaaagga cacaaaggac tctcgaccca aactgcccca    180
```

-continued

| | | |
|---|---|---|
| gaccctctcc agaggttggg gtgaccaact catctggact cagacatatg aagaagctct | 240 | |
| atataaatcc aagacaagca acaaaccctt gatgattatt catcacttgg atgagtgccc | 300 | |
| acacagtcna gctttaaaga aagtgtttgc tgaaaataaa gaaatccaga aattggcaga | 360 | |
| gcagtttgtc ctcctcaatc tggtttatga acaactgac aaacacctt ctcctgatgg | 420 | |
| ccagtatgtc ccaggattat gtttgttgac ccatctctga cagttgaagc cgatatcctg | 480 | |
| ggaagatatt cnaaccgtct ctatgcttac aaactgcaga tacgctctgt tgcttgacac | 540 | |
| atgaaaaagc tctcaagttg ctnaaaatga attgtaagaa aaaaaatctc cagccttctg | 600 | |
| tctgtcggct tgaaaattga aaccagaaaa atgtgaaaaa tggctattgt ggaacanatn | 660 | |
| gacacctgat taggttttgg ttatgttcac cactatttt aanaaaanan nttttaaaat | 720 | |
| ttggttcaat tntctttttn aaacaatntg tttctacntt gnganctgat ttctaaaaaa | 780 | |
| aataatnttt ggc | 793 | |

```
<210> SEQ ID NO 79
<211> LENGTH: 456
<212> TYPE: DNA
<213> ORGANISM: Homo sapiens
<220> FEATURE:
<221> NAME/KEY: modified_base
<222> LOCATION: (89)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (255)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (266)
<223> OTHER INFORMATION: Where n is a, c, g or t
<221> NAME/KEY: modified_base
<222> LOCATION: (286)
<223> OTHER INFORMATION: Where n is a, c, g or t
<221> NAME/KEY: modified_base
<222> LOCATION: (353)
<223> OTHER INFORMATION: Where n is a, c, g or t
<221> NAME/KEY: modified_base
<222> LOCATION: (384)
<223> OTHER INFORMATION: Where n is a, c, g or t
<221> NAME/KEY: modified_base
<222> LOCATION: (423)
<223> OTHER INFORMATION: Where n is a, c, g or t
<221> NAME/KEY: modified_base
<222> LOCATION: (425)
<223> OTHER INFORMATION: Where n is a, c, g or t
<221> NAME/KEY: modified_base
<222> LOCATION: (436)
<223> OTHER INFORMATION: Where n is a, c, g or t
<221> NAME/KEY: modified_base
<222> LOCATION: (441)
<223> OTHER INFORMATION: Where n is a, c, g or t
```

<400> SEQUENCE: 79

| | | |
|---|---|---|
| actagtatgg ggtgggaggc cccacccttc tcccctaggc gctgttcttg ctccaaaggg | 60 | |
| ctccgtggag agggactggc agagctgang ccacctgggg ctgggatcc cactcttctt | 120 | |
| gcagctgttg agcgcaccta accactggtc atgcccccac ccctgctctc cgcacccgct | 180 | |
| tcctcccgac cccangacca ggctacttct ccctcctct tgcctccctc ctgcccctgc | 240 | |
| tgcctctgat cgtangaatt gangantgtc ccgccttgtg gctganaatg gacagtggca | 300 | |
| ggggctggaa atgggtgtgt gtgtgtgtgt gtgtgtgtgt gtgtgtgtgt gcncccccc | 360 | |

```
tgcaagaccg agattgaggg aaancatgtc tgctgggtgt gaccatgttt cctctccata    420
aantncccct gtgacnctca naaaaaaaaa aaaaaa                              456
```

<210> SEQ ID NO 80
<211> LENGTH: 284
<212> TYPE: DNA
<213> ORGANISM: Homo sapiens
<220> FEATURE:
<221> NAME/KEY: modified_base
<222> LOCATION: (283)
<223> OTHER INFORMATION: Where n is a, c, g or t

<400> SEQUENCE: 80

```
ctttgtacct ctagaaaaga taggtattgt gtcatgaaac ttgagtttaa attttatata     60
taaaactaaa agtaatgctc actttagcaa cacatactaa aattggaacc atactgagaa    120
gaatagcatg acctccgtgc aaacaggaca agcaaatttg tgatgtgttg attaaaaaga    180
aataaataaa tgtgtatatg tgtaacttgt atgtttatgt ggaatacaga ttgggaaata    240
aaatgtattt cttactgtga aaaaaaaaaa aaaaaaaaa aana                      284
```

<210> SEQ ID NO 81
<211> LENGTH: 671
<212> TYPE: DNA
<213> ORGANISM: Homo sapiens
<220> FEATURE:
<221> NAME/KEY: modified_base
<222> LOCATION: (388)
<223> OTHER INFORMATION: Where n is a, c, g or t
<221> NAME/KEY: modified_base
<222> LOCATION: (505)
<223> OTHER INFORMATION: Where n is a, c, g or t
<221> NAME/KEY: modified_base
<222> LOCATION: (600)
<223> OTHER INFORMATION: Where n is a, c, g or t
<221> NAME/KEY: modified_base
<222> LOCATION: (603)
<223> OTHER INFORMATION: Where n is a, c, g or t
<221> NAME/KEY: modified_base
<222> LOCATION: (615)
<223> OTHER INFORMATION: Where n is a, c, g or t
<221> NAME/KEY: modified_base
<222> LOCATION: (642)
<223> OTHER INFORMATION: Where n is a, c, g or t
<221> NAME/KEY: modified_base
<222> LOCATION: (644)
<223> OTHER INFORMATION: Where n is a, c, g or t
<221> NAME/KEY: modified_base
<222> LOCATION: (660)
<223> OTHER INFORMATION: Where n is a, c, g or t

<400> SEQUENCE: 81

```
gccaccaaca ttccaagcta ccctgggtac ctttgtgcag tagaagctag tgagcatgtg     60
agcaagcggt gtgcacacgg agactcatcg ttataattta ctatctgcca agagtagaaa    120
gaaaggctgg ggatatttgg gttggcttgg ttttgatttt ttgcttgttt gtttgttttg    180
tactaaaaca gtattatctt ttgaatatcg tagggacata agtatataca tgttatccaa    240
tcaagatggc tagaatggtg cctttctgag tgtctaaaac ttgacacccc tggtaaatct    300
ttcaacacac ttccactgcc tgcgtaatga agttttgatt cattttaac cactggaatt    360 tttcaatgcc gtcattttca gttagatnat tttgcactt gagattaaaa tgccatgtct    420
atttgattag tcttattttt ttatttttac aggcttatca gtctcactgt tggctgtcat    480
tgtgacaaag tcaaataaac ccccnaggac aacacacagt atgggatcac atattgtttg    540
acattaagct ttggccaaaa aatgttgcat gtgttttacc tcgacttgct aaatcaatan    600
```

```
canaaaggct ggctnataat gttggtggtg aaataattaa tnantaacca aaaaaaaaan      660
aaaaaaaaaa a                                                          671

<210> SEQ ID NO 82
<211> LENGTH: 217
<212> TYPE: DNA
<213> ORGANISM: Homo sapiens
<220> FEATURE:
<221> NAME/KEY: modified_base
<222> LOCATION: (35)
<223> OTHER INFORMATION: Where n is a, c, g or t

<400> SEQUENCE: 82
ctgcagatgt tcttgaatg ctttgtcaaa ttaanaaagt taaagtgcaa taatgtttga       60
agacaataag tggtggtgta tcttgtttct aataagataa acttttttgt ctttgcttta     120
tcttattagg gagttgtatg tcagtgtata aaacatactg tgtggtataa caggcttaat     180
aaattcttta aaggaaaaa aaaaaaaaaa aaaaaaa                               217

<210> SEQ ID NO 83
<211> LENGTH: 460
<212> TYPE: DNA
<213> ORGANISM: Homo sapiens
<220> FEATURE:
<221> NAME/KEY: modified_base
<222> LOCATION: (104)
<223> OTHER INFORMATION: Where n is a, c, g or t
<221> NAME/KEY: modified_base
<222> LOCATION: (118)
<223> OTHER INFORMATION: Where n is a, c, g or t
<221> NAME/KEY: modified_base
<222> LOCATION: (172)
<223> OTHER INFORMATION: Where n is a, c, g or t
<221> NAME/KEY: modified_base
<222> LOCATION: (401)
<223> OTHER INFORMATION: Where n is a, c, g or t
<221> NAME/KEY: modified_base
<222> LOCATION: (422)
<223> OTHER INFORMATION: Where n is a, c, g or t
<221> NAME/KEY: modified_base
<222> LOCATION: (423)
<223> OTHER INFORMATION: Where n is a, c, g or t
<221> NAME/KEY: modified_base
<222> LOCATION: (444)
<223> OTHER INFORMATION: Where n is a, c, g or t
<221> NAME/KEY: modified_base
<222> LOCATION: (449)
<223> OTHER INFORMATION: Where n is a, c, g or t

<400> SEQUENCE: 83
cgcgagtggg agcaccagga tctcgggctc ggaacgagac tgcacggatt gttttaagaa      60
aatggcagac aaaccagaca tgggggaaat cgccagcttc gatnaggcca agctgaanaa     120
aacggagacg caggagaaga acaccctgcc gaccaaagag accattgagc angaagcg      180 gagtgaaatt tcctaagatc ctggaggatt tcctaccccc gtcctcttcg agaccccagt     240
cgtgatgtgg aggaagagcc acctgcaaga tggacacgag ccacaagctg cactgtgaac     300
ctgggcactc cgcgccgatg ccaccggcct gtgggtctct gaagggaccc cccccaatcg     360
gactgccaaa ttctccggtt tgccccggga tattatacaa nattatttgt atgaataatg     420
annataaaac acacctcgtg gcancaaana aaaaaaaaa                            460

<210> SEQ ID NO 84
<211> LENGTH: 323
<212> TYPE: DNA
<213> ORGANISM: Homo sapiens
```

```
<220> FEATURE:
<221> NAME/KEY: modified_base
<222> LOCATION: (70)
<223> OTHER INFORMATION: Where n is a, c, g or t
<221> NAME/KEY: modified_base
<222> LOCATION: (138)
<223> OTHER INFORMATION: Where n is a, c, g or t
<221> NAME/KEY: modified_base
<222> LOCATION: (178)
<223> OTHER INFORMATION: Where n is a, c, g or t
<221> NAME/KEY: modified_base
<222> LOCATION: (197)
<223> OTHER INFORMATION: Where n is a, c, g or t
<221> NAME/KEY: modified_base
<222> LOCATION: (228)
<223> OTHER INFORMATION: Where n is a, c, g or t
<221> NAME/KEY: modified_base
<222> LOCATION: (242)
<223> OTHER INFORMATION: Where n is a, c, g or t
<221> NAME/KEY: modified_base
<222> LOCATION: (244)
<223> OTHER INFORMATION: Where n is a, c, g or t
<221> NAME/KEY: modified_base
<222> LOCATION: (287)
<223> OTHER INFORMATION: Where n is a, c, g or t
<221> NAME/KEY: modified_base
<222> LOCATION: (311)
<223> OTHER INFORMATION: Where n is a, c, g or t

<400> SEQUENCE: 84
tggtggatct tggctctgtg gagctgctgg gacgggatct aaaagactat tctggaagct    60
gtggtccaan gcattttgct ggcttaacgg gtcccggaac aaaggacacc agctctctaa   120
aattgaagtt tacccganat aacaatcttt tgggcagaga tgcctatttt aacaaacncc   180
gtccctgcgc aacaacnaac aatctctggg aaataccggc catgaacntg ctgtctcaat   240
cnancatctc tctagctgac cgatcatatc gtcccagatt actacanatc ataataattg   300
atttcctgta naaaaaaaaa aaa                                           323

<210> SEQ ID NO 85
<211> LENGTH: 771
<212> TYPE: DNA
<213> ORGANISM: Homo sapiens
<220> FEATURE:
<221> NAME/KEY: modified_base
<222> LOCATION: (63)
<223> OTHER INFORMATION: Where n is a, c, g or t
<221> NAME/KEY: modified_base
<222> LOCATION: (426)
<223> OTHER INFORMATION: Where n is a, c, g or t
<221> NAME/KEY: modified_base
<222> LOCATION: (471)
<223> OTHER INFORMATION: Where n is a, c, g or t
<221> NAME/KEY: modified_base
<222> LOCATION: (487)
<223> OTHER INFORMATION: Where n is a, c, g or t
<221> NAME/KEY: modified_base
<222> LOCATION: (521)
<223> OTHER INFORMATION: Where n is a, c, g or t
<221> NAME/KEY: modified_base
<222> LOCATION: (554)
<223> OTHER INFORMATION: Where n is a, c, g or t
<221> NAME/KEY: modified_base
<222> LOCATION: (583)
<223> OTHER INFORMATION: Where n is a, c, g or t
<221> NAME/KEY: modified_base
<222> LOCATION: (586)
<223> OTHER INFORMATION: Where n is a, c, g or t
<221> NAME/KEY: modified_base
<222> LOCATION: (606)
<223> OTHER INFORMATION: Where n is a, c, g or t
<221> NAME/KEY: modified_base
<222> LOCATION: (609)
<223> OTHER INFORMATION: Where n is a, c, g or t
```

-continued

```
<221> NAME/KEY: modified_base
<222> LOCATION: (615)
<223> OTHER INFORMATION: Where n is a, c, g or t
<221> NAME/KEY: modified_base
<222> LOCATION: (652)
<223> OTHER INFORMATION: Where n is a, c, g or t
<221> NAME/KEY: modified_base
<222> LOCATION: (686)
<223> OTHER INFORMATION: Where n is a, c, g or t
<221> NAME/KEY: modified_base
<222> LOCATION: (691)
<223> OTHER INFORMATION: Where n is a, c, g or t
<221> NAME/KEY: modified_base
<222> LOCATION: (694)
<223> OTHER INFORMATION: Where n is a, c, g or t
<221> NAME/KEY: modified_base
<222> LOCATION: (695)
<223> OTHER INFORMATION: Where n is a, c, g or t
<221> NAME/KEY: modified_base
<222> LOCATION: (706)
<223> OTHER INFORMATION: Where n is a, c, g or t
<221> NAME/KEY: modified_base
<222> LOCATION: (713)
<223> OTHER INFORMATION: Where n is a, c, g or t
<221> NAME/KEY: modified_base
<222> LOCATION: (730)
<223> OTHER INFORMATION: Where n is a, c, g or t
<221> NAME/KEY: modified_base
<222> LOCATION: (732)
<223> OTHER INFORMATION: Where n is a, c, g or t
<221> NAME/KEY: modified_base
<222> LOCATION: (743)
<223> OTHER INFORMATION: Where n is a, c, g or t
<221> NAME/KEY: modified_base
<222> LOCATION: (751)
<223> OTHER INFORMATION: Where n is a, c, g or t

<400> SEQUENCE: 85
aaactgggta ctcaacactg agcagatctg ttctttgagc taaaaaccat gtgctgtacc      60
aanagtttgc tcctggctgc tttgatgtca gtgctgctac tccacctctg cggcgaatca    120
gaagcaagca actttgactg ctgtcttgga tacacagacc gtattcttca tcctaaattt    180
attgtgggct tcacacggca gctggccaat gaaggctgtg acatcaatgc tatcatcttt    240
cacacaaaga aaaagttgtc tgtgtgcgca atccaaaac agacttgggt gaaatatatt     300
gtgcgtctcc tcagtaaaaa agtcaagaac atgtaaaaac tgtggctttt ctggaatgga    360
attggacata gcccaagaac agaaagaact tgctggggtt ggaggtttca cttgcacatc    420
atgganggtt tagtgcttat cttatttgtg cctcctggac ttgtccaatt natgaagtta    480
atcatattgc atcatanttt gctttgttta acatcacatt naaattaaac tgtatttat     540 gttatttata gctntaggtt ttctgtgttt aactttttat acnaantttc ctaaactatt    600
ttggtntant gcaanttaaa aattatattt gggggggaa taaatattgg antttctgca     660
gccacaagct tttttaaaa aaccantaca nccnngttaa atggtnggtc ccnaatggtt     720
tttgcttttn antagaaaat ttnttagaac natttgaaaa aaaaaaaaa a               771

<210> SEQ ID NO 86
<211> LENGTH: 628
<212> TYPE: DNA
<213> ORGANISM: Homo sapiens
<220> FEATURE:
<221> NAME/KEY: modified_base
<222> LOCATION: (162)
<223> OTHER INFORMATION: Where n is a, c, g or t
<221> NAME/KEY: modified_base
<222> LOCATION: (249)
<223> OTHER INFORMATION: Where n is a, c, g or t
<221> NAME/KEY: modified_base
<222> LOCATION: (266)
```

<223> OTHER INFORMATION: Where n is a, c, g or t
<221> NAME/KEY: modified_base
<222> LOCATION: (348)
<223> OTHER INFORMATION: Where n is a, c, g or t
<221> NAME/KEY: modified_base
<222> LOCATION: (407)
<223> OTHER INFORMATION: Where n is a, c, g or t
<221> NAME/KEY: modified_base
<222> LOCATION: (427)
<223> OTHER INFORMATION: Where n is a, c, g or t
<221> NAME/KEY: modified_base
<222> LOCATION: (488)
<223> OTHER INFORMATION: Where n is a, c, g or t
<221> NAME/KEY: modified_base
<222> LOCATION: (518)
<223> OTHER INFORMATION: Where n is a, c, g or t
<221> NAME/KEY: modified_base
<222> LOCATION: (545)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (569)
<223> OTHER INFORMATION: Where n is a, c, g or t
<221> NAME/KEY: modified_base
<222> LOCATION: (597)
<223> OTHER INFORMATION: Where n is a, c, g or t
<221> NAME/KEY: modified_base
<222> LOCATION: (598)
<223> OTHER INFORMATION: Where n is a, c, g or t
<221> NAME/KEY: modified_base
<222> LOCATION: (611)
<223> OTHER INFORMATION: Where n is a, c, g or t
<221> NAME/KEY: modified_base
<222> LOCATION: (617)
<223> OTHER INFORMATION: Where n is a, c, g or t
<221> NAME/KEY: modified_base
<222> LOCATION: (621)
<223> OTHER INFORMATION: Where n is a, c, g or t
<221> NAME/KEY: modified_base
<222> LOCATION: (624)
<223> OTHER INFORMATION: Where n is a, c, g or t

<400> SEQUENCE: 86

```
actagtttgc tttacatttt tgaaaagtat tatttttgtc caagtgctta tcaactaaac    60
cttgtgttag gtaagaatgg aatttattaa gtgaatcagt gtgacccttc ttgtcataag   120
attatcttaa agctgaagcc aaaatatgct tcaaaagaaa angactttat tgttcattgt   180
agttcataca ttcaaagcat ctgaactgta gtttctatag caagccaatt acatccataa   240
gtggagaang aaatagatta atgtcnaagt atgattggtg gagggagcaa ggttgaagat   300
aatctggggt tgaaattttc tagttttcat tctgtacatt tttagttnga catcagattt   360
gaaatattaa tgtttacctt tcaatgtgtg gtatcagctg gactcantaa cacccctttc   420
ttccctnggg gatggggaat ggattattgg aaaatggaaa gaaaaagta cttaaagcct   480
tcctttcnca gtttctggct cctaccctac tgatttancc agaataagaa aacattttat   540
catcntctgc tttattccca ttaatnaant tttgatgaat aaatctgctt ttatgcnnac   600
ccaaggaatt nagtggnttc ntcnttgt                                     628
```

<210> SEQ ID NO 87
<211> LENGTH: 518
<212> TYPE: DNA
<213> ORGANISM: Homo sapiens
<220> FEATURE:
<221> NAME/KEY: modified_base
<222> LOCATION: (384)
<223> OTHER INFORMATION: Where n is a, c, g or t
<221> NAME/KEY: modified_base
<222> LOCATION: (421)

<223> OTHER INFORMATION: Where n is a, c, g or t
<221> NAME/KEY: modified_base
<222> LOCATION: (486)
<223> OTHER INFORMATION: Where n is a, c, g or t

<400> SEQUENCE: 87

| | | | | | |
|---|---|---|---|---|---|
| tttttttattt | tttttagaga | gtagttcagc | ttttatttat | aaatttattg | cctgttttat | 60 |
| tataacaaca | ttatactgtt | tatggtttaa | tacatatggt | tcaaaatgta | taatacatca | 120 |
| agtagtacag | ttttaaaatt | ttatgcttaa | aacaagtttt | gtgtaaaaaa | tgcagataca | 180 |
| ttttacatgg | caaatcaatt | tttaagtcat | cctaaaaatt | gattttttt | tgaaatttaa | 240 |
| aaacacattt | aatttcaatt | tctctcttat | ataaccttta | ttactatagc | atggtttcca | 300 |
| ctacagttta | acaatgcagc | aaaattccca | tttcacggta | aattgggttt | taagcggcaa | 360 |
| ggttaaaatg | ctttgaggat | cctnaatacc | ctttgaactt | caaatgaagg | ttatggttgt | 420 |
| naatttaacc | ctcatgccat | aagcagaagc | acaagtttag | ctgcattttg | ctctaaactg | 480 |
| taaaancgag | cccccgttg | aaaaagcaaa | agggaccc | | | 518 |

<210> SEQ ID NO 88
<211> LENGTH: 1844
<212> TYPE: DNA
<213> ORGANISM: Homo sapiens

<400> SEQUENCE: 88

| | | | | | |
|---|---|---|---|---|---|
| gagacagtga | atcctagtat | caaaggattt | ttggcctcag | aaaaagttgt | tgattatttt | 60 |
| tatttttattt | tattttttcga | gactccgtct | caaaaaaaaa | aaaaaaaaaa | agaatcacaa | 120 |
| ggtatttgct | aaagcatttt | gagctgcttg | gaaaaaggga | agtagttgca | gtagagtttc | 180 |
| ttccatcttc | ttggtgctgg | gaagccatat | atgtgtcttt | tactcaagct | aagggtata | 240 |
| agcttatgtg | ttgaatttgc | tacatctata | tttcacatat | tctcacaata | agagaatttt | 300 |
| gaaatagaaa | tatcatagaa | catttaagaa | agtttagtat | aaataatatt | ttgtgtgttt | 360 |
| taatcccttt | gaagggatct | atccaaagaa | aatattttac | actgagctcc | ttcctacacg | 420 |
| tctcagtaac | agatcctgtg | ttagtctttg | aaaatagctc | atttttaaa | tgtcagtgag | 480 |
| tagatgtagc | atacatatga | tgtataatga | cgtgtattat | gttaacaatg | tctgcagatt | 540 |
| ttgtaggaat | acaaacatg | gcctttttta | taagcaaaac | gggccaatga | ctagaataac | 600 |
| acatagggca | atctgtgaat | atgtattata | agcagcattc | cagaaaagta | gttggtgaaa | 660 |
| taattttcaa | gtcaaaaagg | gatatggaaa | gggaattatg | agtaacctct | attttttaag | 720 |
| ccttgctttt | aaattaaacg | ctacagccat | ttaagccttg | aggataataa | agcttgagag | 780 |
| taataatgtt | aggttagcaa | aggtttagat | gtatcacttc | atgcatgcta | ccatgatagt | 840 |
| aatgcagctc | ttcgagtcat | ttctggtcat | tcaagatatt | caccttttg | cccatagaaa | 900 |
| gcaccctacc | tcacctgctt | actgacattg | tcttagctga | tcacaagatc | attatcagcc | 960 |
| tccattattc | cttactgtat | ataaaataca | gagttttata | ttttcctttc | ttcgtttttc | 1020 |
| accatattca | aaacctaaat | ttgttttttgc | agatggaatg | caaagtaatc | aagtgttcgt | 1080 |
| gctttcacct | agaagggtgt | ggtcctgaag | gaaagaggtc | cctaaatatc | ccccaccctg | 1140 |
| ggtgctcctc | cttccctggt | accctgacta | ccagaagtca | ggtgctagag | cagctggaga | 1200 |
| agtgcagcag | cctgtgcttc | cacagatggg | ggtgctgctg | caacaaggct | ttcaatgtgc | 1260 |
| ccatcttagg | gggagaagct | agatcctgtg | cagcagcctg | gtaagtcctg | aggaggttcc | 1320 |
| attgctcttc | ctgctgctgt | cctttgcttc | tcaacggggc | tcgctctaca | gtctagagca | 1380 |

```
catgcagcta acttgtgcct ctgcttatgc atgagggtta aattaacaac cataaccttc    1440
atttgaagtt caaaggtgta ttcaggatcc tcaaagcatt ttaaccttgc cgcttaaaac    1500
ccaatttacc gtgaaatggg aattttgctg cattgttaaa ctgtagtgga aaccatgcta    1560
tagtaataaa ggttatataa gagagaaatt gaaattaaat gtgttttaa atttcaaaaa      1620 aaaatcaatc tttaggatga cttaaaaatt gatttgccat gtaaaatgta tctgcatttt    1680
ttacacaaaa cttgttttaa gcataaaatt ttaaaactgt actacttgat gtattataca    1740
ttttgaacca tatgtattaa accataaaca gtataatgtt gttataataa aacaggcaat    1800
aaatttataa ataaaagctg aaaaaaaaaa aaaaaaaaa aaaa                       1844
```

<210> SEQ ID NO 89
<211> LENGTH: 523
<212> TYPE: DNA
<213> ORGANISM: Homo sapiens
<220> FEATURE:
<221> NAME/KEY: modified_base
<222> LOCATION: (288)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (369)
<223> OTHER INFORMATION: Where n is a, c, g or t
<221> NAME/KEY: modified_base
<222> LOCATION: (398)
<223> OTHER INFORMATION: Where n is a, c, g or t
<221> NAME/KEY: modified_base
<222> LOCATION: (475)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (513)
<223> OTHER INFORMATION: Where n is a, c, g or t

<400> SEQUENCE: 89

```
tttttttttt ttttttagt caatccacat ttattgatca cttattatgt accaggcact       60
gggataaaga tgactgttag tcactcacag taaggaagaa aactagcaaa taagacgatt      120
acaatatgat gtagaaaatg ctaagccaga gatatagaaa ggtcctattg ggtccttctg      180
tcaccttgtc tttccacatc cctacccttc acaggccttc cctccagctt cctgcccccg      240
ctccccactg cagatcccct gggattttgc ctagagctaa acgagganat gggcccctg       300 gccctggcat gacttgaacc caaccacaga ctgggaaagg gagcctttcg anagtggatc      360
actttgatna gaaaacacat agggaattga agagaaantc cccaaatggc cacccgtgct     420
ggtgctcaag aaaagtttgc agaatggata aatgaaggat caagggaatt aatanatgaa      480
taattgaatg gtggctcaat aagaatgact ncnttgaatg acc                        523
```

<210> SEQ ID NO 90
<211> LENGTH: 604
<212> TYPE: DNA
<213> ORGANISM: Homo sapiens
<220> FEATURE:
<221> NAME/KEY: modified_base
<222> LOCATION: (563)
<223> OTHER INFORMATION: Where n is a, c, g or t

<400> SEQUENCE: 90

```
ccagtgtggt ggaatgcaaa gattacccccg gaagctttcg agaagctggg attccctgca     60
gcaaaggaaa tagccaatat gtgtcgtttc tatgaaatga agccagaccg agatgtcaat     120
```

```
ctcacccacc aactaaatcc caaagtcaaa agcttcagcc agtttatctc agagaaccag      180
gggagccttc aagggcatgt agaaaatcag ctgttcagat aggcctctgc accacacagc      240
ctctttcctc tctgatcctt ttcctcttta cggcacaaca ttcatgtttg acagaacatg      300
ctggaatgca attgtttgca acaccgaagg atttcctgcg gtcgcctctt cagtaggaag      360
cactgcattg gtgataggac acggtaattt gattcacatt taacttgcta gttagtgata      420 agggtggta cacctgtttg gtaaaatgag aagcctcgga aacttgggag cttctctcct       480
accactaatg gggagggcag attattactg ggatttctcc tggggtgaat taatttcaag      540
ccctaattgc tgaaattccc ctnggcaggc tccagttttc tcaactgcat tgcaaaattc      600
cccc                                                                   604
```

```
<210> SEQ ID NO 91
<211> LENGTH: 858
<212> TYPE: DNA
<213> ORGANISM: Homo sapiens
<220> FEATURE:
<221> NAME/KEY: modified_base
<222> LOCATION: (570)
<223> OTHER INFORMATION: Where n is a, c, g or t
<221> NAME/KEY: modified_base
<222> LOCATION: (591)
<223> OTHER INFORMATION: Where n is a, c, g or t
<221> NAME/KEY: modified_base
<222> LOCATION: (655)
<223> OTHER INFORMATION: Where n is a, c, g or t
<221> NAME/KEY: modified_base
<222> LOCATION: (664)
<223> OTHER INFORMATION: Where n is a, c, g or t
<221> NAME/KEY: modified_base
<222> LOCATION: (667)
<223> OTHER INFORMATION: Where n is a, c, g or t
<221> NAME/KEY: modified_base
<222> LOCATION: (683)
<223> OTHER INFORMATION: Where n is a, c, g or t
<221> NAME/KEY: modified_base
<222> LOCATION: (711)
<223> OTHER INFORMATION: Where n is a, c, g or t
<221> NAME/KEY: modified_base
<222> LOCATION: (759)
<223> OTHER INFORMATION: Where n is a, c, g or t
<221> NAME/KEY: modified_base
<222> LOCATION: (760)
<223> OTHER INFORMATION: Where n is a, c, g or t
<221> NAME/KEY: modified_base
<222> LOCATION: (765)
<223> OTHER INFORMATION: Where n is a, c, g or t
<221> NAME/KEY: modified_base
<222> LOCATION: (777)
<223> OTHER INFORMATION: Where n is a, c, g or t
<221> NAME/KEY: modified_base
<222> LOCATION: (787)
<223> OTHER INFORMATION: Where n is a, c, g or t
<221> NAME/KEY: modified_base
<222> LOCATION: (792)
<223> OTHER INFORMATION: Where n is a, c, g or t
<221> NAME/KEY: modified_base
<222> LOCATION: (794)
<223> OTHER INFORMATION: Where n is a, c, g or t
<221> NAME/KEY: modified_base
<222> LOCATION: (801)
<223> OTHER INFORMATION: Where n is a, c, g or t
<221> NAME/KEY: modified_base
<222> LOCATION: (804)
<223> OTHER INFORMATION: Where n is a, c, g or t
<221> NAME/KEY: modified_base
<222> LOCATION: (809)
<223> OTHER INFORMATION: Where n is a, c, g or t
<221> NAME/KEY: modified_base
<222> LOCATION: (817)
<223> OTHER INFORMATION: Where n is a, c, g or t
```

<221> NAME/KEY: modified_base
<222> LOCATION: (820)
<223> OTHER INFORMATION: Where n is a, c, g or t

<400> SEQUENCE: 91

```
tttttttttt ttttttttta tgattattat tttttttatt gatctttaca tcctcagtgt      60
tggcagagtt tctgatgctt aataaacatt tgttctgatc agataagtgg aaaaaattgt     120
catttcctta ttcaagccat gcttttctgt gatattctga tcctagttga acatacagaa     180
ataaatgtct aaaacagcac ctcgattctc gtctataaca ggactaagtt cactgtgatc     240
ttaaataagc ttggctaaaa tgggacatga gtggaggtag tcacacttca gcgaagaaag     300
agaatctcct gtataatctc accaggagat tcaacgaatt ccaccacact ggactagtgg     360
atcccccggg ctgcaggaat tcgatatcaa gcttatcgat accgtcgacc tcgaggggg      420
gcccggtacc caattcgccc tatagtgagt cgtattacgc gcgctcactg gccgtcgttt     480
tacaacgtcg tgactgggaa accctggcg ttacccaact taatcgcctt gcagcacatc      540
cccctttcgc cagctggcgt aatagcgaan agcccgcacc gatcgccctt ncaacagttg     600
cgcagcctga atggcgaatg ggacgcgccc tgtagcggcg cattaaagcg cggcngggtg     660
tggnggntcc cccacgtgac cgntacactt ggcagcgcct tacgccggtc nttcgctttc     720
ttcccttcct ttctcgcacc gttcgccggg ttttcccgnn agctnttaat cggggnctc      780
cctttanggg tncnaattaa nggnttacng gaccttngan cccaaaaact ttgattaggg     840
ggaaggtccc cgaagggg                                                   858
```

<210> SEQ ID NO 92
<211> LENGTH: 585
<212> TYPE: DNA
<213> ORGANISM: Homo sapiens
<220> FEATURE:
<221> NAME/KEY: modified_base
<222> LOCATION: (317)
<223> OTHER INFORMATION: Where n is a, c, g or t
<221> NAME/KEY: modified_base
<222> LOCATION: (319)
<223> OTHER INFORMATION: Where n is a, c, g or t
<221> NAME/KEY: modified_base
<222> LOCATION: (320)
<223> OTHER INFORMATION: Where n is a, c, g or t
<221> NAME/KEY: modified_base
<222> LOCATION: (321)
<223> OTHER INFORMATION: Where n is a, c, g or t
<221> NAME/KEY: modified_base
<222> LOCATION: (325)
<223> OTHER INFORMATION: Where n is a, c, g or t
<221> NAME/KEY: modified_base
<222> LOCATION: (327)
<223> OTHER INFORMATION: Where n is a, c, g or t
<221> NAME/KEY: modified_base
<222> LOCATION: (328)
<223> OTHER INFORMATION: Where n is a, c, g or t
<221> NAME/KEY: modified_base
<222> LOCATION: (330)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (332)
<223> OTHER INFORMATION: Where n is a, c, g or t
<221> NAME/KEY: modified_base
<222> LOCATION: (460)
<223> OTHER INFORMATION: Where n is a, c, g or t
<221> NAME/KEY: modified_base
<222> LOCATION: (462)
<223> OTHER INFORMATION: Where n is a, c, g or t
<221> NAME/KEY: modified_base

```
<222> LOCATION: (483)
<223> OTHER INFORMATION: Where n is a, c, g or t
<221> NAME/KEY: modified_base
<222> LOCATION: (485)
<223> OTHER INFORMATION: Where n is a, c, g or t
<221> NAME/KEY: modified_base
<222> LOCATION: (487)
<223> OTHER INFORMATION: Where n is a, c, g or t
<221> NAME/KEY: modified_base
<222> LOCATION: (523)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (584)
<223> OTHER INFORMATION: Where n is a, c, g or t

<400> SEQUENCE: 92
gttgaatctc ctggtgagat tatacaggag attctctttc ttcgctgaag tgtgactacc      60
tccactcatg tcccatttta gccaagctta tttaagatca cagtgaactt agtcctgtta     120
tagacgagaa tcgaggtgct gttttagaca tttatttctg tatgttcaac taggatcaga     180
atatcacaga aaagcatggc ttgaataagg aaatgacaat tttttccact tatctgatca     240
gaacaaatgt ttattaagca tcagaaactc tgccaacact gaggatgtaa agatcaataa     300
aaaaaataat aatcatnann naaanannan nngaagggcg gccgccaccg cggtggagct     360
ccagcttttg ttccctttag tgagggttaa ttgcgcgctt ggcgttaatc atggtcatag     420
ctgtttcctg tgtgaaattg ttatccggct cacaattccn cncaacatac gagccgggaa     480
gcntnangtg taaaagcctg ggggtgccta attgagtgag ctnactcaca ttaattgngt     540
tgcgctccac ttgcccgctt ttccantccg ggaaacctgt tcgnc                    585

<210> SEQ ID NO 93
<211> LENGTH: 567
<212> TYPE: DNA
<213> ORGANISM: Homo sapiens
<220> FEATURE:
<221> NAME/KEY: modified_base
<222> LOCATION: (82)
<223> OTHER INFORMATION: Where n is a, c, g or t
<221> NAME/KEY: modified_base
<222> LOCATION: (158)
<223> OTHER INFORMATION: Where n is a, c, g or t
<221> NAME/KEY: modified_base
<222> LOCATION: (230)
<223> OTHER INFORMATION: Where n is a, c, g or t
<221> NAME/KEY: modified_base
<222> LOCATION: (232)
<223> OTHER INFORMATION: Where n is a, c, g or t
<221> NAME/KEY: modified_base
<222> LOCATION: (253)
<223> OTHER INFORMATION: Where n is a, c, g or t
<221> NAME/KEY: modified_base
<222> LOCATION: (266)..(287)
<223> OTHER INFORMATION: Where n is a, c, g or t
<221> NAME/KEY: modified_base
<222> LOCATION: (295)
<223> OTHER INFORMATION: Where n is a, c, g or t
<221> NAME/KEY: modified_base
<222> LOCATION: (303)
<223> OTHER INFORMATION: Where n is a, c, g or t
<221> NAME/KEY: modified_base
<222> LOCATION: (307)
<223> OTHER INFORMATION: Where n is a, c, g or t
<221> NAME/KEY: modified_base
<222> LOCATION: (314)
<223> OTHER INFORMATION: Where n is a, c, g or t
```

```
<221> NAME/KEY: modified_base
<222> LOCATION: (349)
<223> OTHER INFORMATION: Where n is a, c, g or t
<221> NAME/KEY: modified_base
<222> LOCATION: (352)
<223> OTHER INFORMATION: Where n is a, c, g or t
<221> NAME/KEY: modified_base
<222> LOCATION: (354)
<223> OTHER INFORMATION: Where n is a, c, g or t
<221> NAME/KEY: modified_base
<222> LOCATION: (356)
<223> OTHER INFORMATION: Where n is a, c, g or t
<221> NAME/KEY: modified_base
<222> LOCATION: (366)
<223> OTHER INFORMATION: Where n is a, c, g or t
<221> NAME/KEY: modified_base
<222> LOCATION: (369)
<223> OTHER INFORMATION: Where n is a, c, g or t
<221> NAME/KEY: modified_base
<222> LOCATION: (379)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (386)
<223> OTHER INFORMATION: Where n is a, c, g or t
<221> NAME/KEY: modified_base
<222> LOCATION: (393)
<223> OTHER INFORMATION: Where n is a, c, g or t
<221> NAME/KEY: modified_base
<222> LOCATION: (404)
<223> OTHER INFORMATION: Where n is a, c, g or t
<221> NAME/KEY: modified_base
<222> LOCATION: (427)
<223> OTHER INFORMATION: Where n is a, c, g or t
<221> NAME/KEY: modified_base
<222> LOCATION: (428)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (452)
<223> OTHER INFORMATION: Where n is a, c, g or t
<221> NAME/KEY: modified_base
<222> LOCATION: (453)
<223> OTHER INFORMATION: Where n is a, c, g or t
<221> NAME/KEY: modified_base
<222> LOCATION: (454)
<223> OTHER INFORMATION: Where n is a, c, g or t
<221> NAME/KEY: modified_base
<222> LOCATION: (459)
<223> OTHER INFORMATION: Where n is a, c, g or t
<221> NAME/KEY: modified_base
<222> LOCATION: (462)
<223> OTHER INFORMATION: Where n is a, c, g or t
<221> NAME/KEY: modified_base
<222> LOCATION: (480)
<223> OTHER INFORMATION: Where n is a, c, g or t
<221> NAME/KEY: modified_base
<222> LOCATION: (481)
<223> OTHER INFORMATION: Where n is a, c, g or t
<221> NAME/KEY: modified_base
<222> LOCATION: (483)
<223> OTHER INFORMATION: Where n is a, c, g or t
<221> NAME/KEY: modified_base
<222> LOCATION: (488)
<223> OTHER INFORMATION: Where n is a, c, g or t
<221> NAME/KEY: modified_base
<222> LOCATION: (493)
<223> OTHER INFORMATION: Where n is a, c, g or t
<221> NAME/KEY: modified_base
<222> LOCATION: (501)
<223> OTHER INFORMATION: Where n is a, c, g or t
<221> NAME/KEY: modified_base
```

```
<222> LOCATION: (509)
<223> OTHER INFORMATION: Where n is a, c, g or t
<221> NAME/KEY: modified_base
<222> LOCATION: (511)
<223> OTHER INFORMATION: Where n is a, c, g or t
<221> NAME/KEY: modified_base
<222> LOCATION: (512)
<223> OTHER INFORMATION: Where n is a, c, g or t
<221> NAME/KEY: modified_base
<222> LOCATION: (518)
<223> OTHER INFORMATION: Where n is a, c, g or t
<221> NAME/KEY: modified_base
<222> LOCATION: (520)
<223> OTHER INFORMATION: Where n is a, c, g or t
<221> NAME/KEY: modified_base
<222> LOCATION: (525)
<223> OTHER INFORMATION: Where n is a, c, g or t
<221> NAME/KEY: modified_base
<222> LOCATION: (526)
<223> OTHER INFORMATION: Where n is a, c, g or t
<221> NAME/KEY: modified_base
<222> LOCATION: (532)
<223> OTHER INFORMATION: Where n is a, c, g or t
<221> NAME/KEY: modified_base
<222> LOCATION: (541)
<223> OTHER INFORMATION: Where n is a, c, g or t
<221> NAME/KEY: modified_base
<222> LOCATION: (557)
<223> OTHER INFORMATION: Where n is a, c, g or t

<400> SEQUENCE: 93
cggcagtgtt gctgtctgcg tgtccacctt ggaatctggc tgaactggct gggaggacca      60
agactgcggc tggggtgggc anggaaggga accgggggct gctgtgaagg atcttggaac     120
ttccctgtac ccaccttccc cttgcttcat gtttgtanag gaaccttgtg ccggccaagc     180
ccagtttcct tgtgtgatac actaatgtat ttgcttttt tgggaaatan anaaaaatca     240
attaaattgc tantgtttct ttgaannnnn nnnnnnnnnn nnnnnnnggg ggggncgccc     300
ccncggngga aacnccccct tttgttccct ttaattgaaa ggttaattng cncncntggc     360
gttaanccnt gggccaaanc tngttncccg tgntgaaatt gttnatcccc tcccaaattc     420
ccccccnncc ttccaaaccc ggaaancctn annntgttna ancccggggg gttgcctaan     480
ngnaattnaa ccnaacccccc ntttaaatng nntttgcncn ccacnngccc cncttccca     540 nttcggggaa aaccctntcc gtgccca                                         567

<210> SEQ ID NO 94
<211> LENGTH: 620
<212> TYPE: DNA
<213> ORGANISM: Homo sapiens
<220> FEATURE:
<221> NAME/KEY: modified_base
<222> LOCATION: (169)
<223> OTHER INFORMATION: Where n is a, c, g or t
<221> NAME/KEY: modified_base
<222> LOCATION: (171)
<223> OTHER INFORMATION: Where n is a, c, g or t
<221> NAME/KEY: modified_base
<222> LOCATION: (222)
<223> OTHER INFORMATION: Where n is a, c, g or t
<221> NAME/KEY: modified_base
<222> LOCATION: (472)
<223> OTHER INFORMATION: Where n is a, c, g or t
<221> NAME/KEY: modified_base
<222> LOCATION: (528)
<223> OTHER INFORMATION: Where n is a, c, g or t
<221> NAME/KEY: modified_base
<222> LOCATION: (559)
<223> OTHER INFORMATION: Where n is a, c, g or t
<221> NAME/KEY: modified_base
<222> LOCATION: (599)
<223> OTHER INFORMATION: Where n is a, c, g or t
```

<400> SEQUENCE: 94

```
actagtcaaa aatgctaaaa taatttggga gaaaatattt tttaagtagt gttatagttt      60
catgtttatc ttttattatg ttttgtgaag ttgtgtcttt tcactaatta cctatactat     120
gccaatattt ccttatatct atccataaca tttatactac atttgtaana naatatgcac     180
gtgaaactta acactttata aggtaaaaat gaggtttcca anatttaata atctgatcaa     240
gttcttgtta tttccaaata gaatggactt ggtctgttaa gggctaagga gaagaggaag     300
ataaggttaa aagttgttaa tgaccaaaca ttctaaaaga aatgcaaaaa aaaagtttat     360
tttcaagcct tcgaactatt taaggaaagc aaaatcattt cctaaatgca tatcatttgt     420
gagaatttct cattaatatc ctgaatcatt catttcacta aggctcatgt tnactccgat     480
atgtctctaa gaaagtacta tttcatggtc caaacctggt tgccatantt gggtaaaggc     540
tttcccttaa gtgtgaaant atttaaaatg aaattttcct ctttttaaaa attctttana     600
agggttaagg gtgttgggga                                                 620
```

<210> SEQ ID NO 95
<211> LENGTH: 470
<212> TYPE: DNA
<213> ORGANISM: Homo sapiens
<220> FEATURE:
<221> NAME/KEY: modified_base
<222> LOCATION: (61)
<223> OTHER INFORMATION: Where n is a, c, g or t
<221> NAME/KEY: modified_base
<222> LOCATION: (67)
<223> OTHER INFORMATION: Where n is a, c, g or t
<221> NAME/KEY: modified_base
<222> LOCATION: (79)
<223> OTHER INFORMATION: Where n is a, c, g or t
<221> NAME/KEY: modified_base
<222> LOCATION: (89)
<223> OTHER INFORMATION: Where n is a, c, g or t
<221> NAME/KEY: modified_base
<222> LOCATION: (106)
<223> OTHER INFORMATION: Where n is a, c, g or t
<221> NAME/KEY: modified_base
<222> LOCATION: (213)
<223> OTHER INFORMATION: Where n is a, c, g or t
<221> NAME/KEY: modified_base
<222> LOCATION: (271)
<223> OTHER INFORMATION: Where n is a, c, g or t
<221> NAME/KEY: modified_base
<222> LOCATION: (281)
<223> OTHER INFORMATION: Where n is a, c, g or t
<221> NAME/KEY: modified_base
<222> LOCATION: (330)
<223> OTHER INFORMATION: Where n is a, c, g or t
<221> NAME/KEY: modified_base
<222> LOCATION: (356)
<223> OTHER INFORMATION: Where n is a, c, g or t
<221> NAME/KEY: modified_base
<222> LOCATION: (387)
<223> OTHER INFORMATION: Where n is a, c, g or t
<221> NAME/KEY: modified_base
<222> LOCATION: (432)
<223> OTHER INFORMATION: Where n is a, c, g or t
<221> NAME/KEY: modified_base
<222> LOCATION: (448)
<223> OTHER INFORMATION: Where n is a, c, g or t

<400> SEQUENCE: 95

```
ctcgaccttc tctgcacagc ggatgaaccc tgagcagctg aagaccagaa aagccactat      60
nactttntgc ttaattcang agcttacang attcttcaaa gagtgngtcc agcatccttt     120
gaaacatgag ttcttaccag cagaagcaga cctttacccc accacctcag cttcaacagc     180
```

```
agcaggtgaa acaacccatc cagcctccac ctnaggaaat atttgttccc acaaccaagg    240
agccatgcca ctcaaaggtt ccacaacctg naaacacaaa nattccagag ccaggctgta    300
ccaaggtccc tgagccaggg ctgtaccaan gtccctgagc caggttgtac caangtccct    360
gagccaggat gtaccaaggt ccctgancca ggttgtccaa ggtccctgag ccaggctaca    420
ccaagggcct gngccaggca gcatcaangt ccctgaccaa ggcttatcaa               470
```

```
<210> SEQ ID NO 96
<211> LENGTH: 718
<212> TYPE: DNA
<213> ORGANISM: Homo sapiens
<220> FEATURE:
<221> NAME/KEY: modified_base
<222> LOCATION: (299)
<223> OTHER INFORMATION: Where n is a, c, g or t
<221> NAME/KEY: modified_base
<222> LOCATION: (311)
<223> OTHER INFORMATION: Where n is a, c, g or t
<221> NAME/KEY: modified_base
<222> LOCATION: (360)
<223> OTHER INFORMATION: Where n is a, c, g or t
<221> NAME/KEY: modified_base
<222> LOCATION: (426)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (540)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (553)
<223> OTHER INFORMATION: Where n is a, c, g or t
<221> NAME/KEY: modified_base
<222> LOCATION: (563)
<223> OTHER INFORMATION: Where n is a, c, g or t
<221> NAME/KEY: modified_base
<222> LOCATION: (565)
<223> OTHER INFORMATION: Where n is a, c, g or t
<221> NAME/KEY: modified_base
<222> LOCATION: (592)
<223> OTHER INFORMATION: Where n is a, c, g or t
<221> NAME/KEY: modified_base
<222> LOCATION: (603)
<223> OTHER INFORMATION: Where n is a, c, g or t
<221> NAME/KEY: modified_base
<222> LOCATION: (604)
<223> OTHER INFORMATION: Where n is a, c, g or t
<221> NAME/KEY: modified_base
<222> LOCATION: (618)
<223> OTHER INFORMATION: Where n is a, c, g or t
<221> NAME/KEY: modified_base
<222> LOCATION: (633)
<223> OTHER INFORMATION: Where n is a, c, g or t
<221> NAME/KEY: modified_base
<222> LOCATION: (647)
<223> OTHER INFORMATION: Where n is a, c, g or t
<221> NAME/KEY: modified_base
<222> LOCATION: (649)
<223> OTHER INFORMATION: Where n is a, c, g or t
<221> NAME/KEY: modified_base
<222> LOCATION: (651)
<223> OTHER INFORMATION: Where n is a, c, g or t
<221> NAME/KEY: modified_base
<222> LOCATION: (653)
<223> OTHER INFORMATION: Where n is a, c, g or t
<221> NAME/KEY: modified_base
<222> LOCATION: (662)
<223> OTHER INFORMATION: Where n is a, c, g or t
<221> NAME/KEY: modified_base
<222> LOCATION: (668)
<223> OTHER INFORMATION: Where n is a, c, g or t
```

<221> NAME/KEY: modified_base
<222> LOCATION: (682)
<223> OTHER INFORMATION: Where n is a, c, g or t
<221> NAME/KEY: modified_base
<222> LOCATION: (691)
<223> OTHER INFORMATION: Where n is a, c, g or t
<221> NAME/KEY: modified_base
<222> LOCATION: (710)
<223> OTHER INFORMATION: Where n is a, c, g or t
<221> NAME/KEY: modified_base
<222> LOCATION: (715)
<223> OTHER INFORMATION: Where n is a, c, g or t

<400> SEQUENCE: 96

| | | | | | |
|---|---|---|---|---|---|
| ttttttttt | tttttttttt | ggaattaaaa | gcaatttaat | gagggcagag | caggaaacat | 60 |
| gcatttcttt | tcattcgaat | cttcagatga | accctgagca | gccgaagacc | agaaaagcca | 120 |
| tgaagacttt | ctgcttaatt | cagggcttta | caggattctt | cagagtgtgt | gtgaacaaaa | 180 |
| gctttatagt | acgtattttt | aggatacaaa | taagagagag | actatggctt | ggggtgagaa | 240 |
| tgtactgatt | acaaggtcta | cagacaatta | agacacagaa | acagatggga | agagggtgnc | 300 |
| cagcatctgg | nggttggctt | ctcaagggct | tgtctgtgca | ccaaattact | tctgcttggn | 360 |
| cttctgctga | gctgggcctg | gagtgaccgt | tgaaggacat | ggctctggta | cctttgtgta | 420 |
| gcctgncaca | ggaactttgg | tgtatccttg | ctcaggaact | ttgatggcac | ctggctcagg | 480 |
| aaacttgatg | aagccttggt | caagggacct | tgatgcttgc | tggctcaggg | accttggngn | 540 |
| anccTgggct | canggacctt | tgncncaacc | ttggcttcaa | gggacccttg | gnacatcctg | 600 |
| gcnnagggac | ccttgggncc | aaccctgggc | ttnagggacc | ctttggntnc | nanccttggc | 660 |
| tnaagggnac | ccttggcaac | anccTgggct | ntggaaaatc | ttttggggtn | cccngggr | 718 |

<210> SEQ ID NO 97
<211> LENGTH: 441
<212> TYPE: DNA
<213> ORGANISM: Homo sapiens
<220> FEATURE:
<221> NAME/KEY: modified_base
<222> LOCATION: (12)
<223> OTHER INFORMATION: Where n is a, c, g or t
<221> NAME/KEY: modified_base
<222> LOCATION: (308)
<223> OTHER INFORMATION: Where n is a, c, g or t

<400> SEQUENCE: 97

| | | | | | |
|---|---|---|---|---|---|
| gggaccatac | anagtattcc | tctcttcaca | ccaggaccag | ccactgttgc | agcatgagtt | 60 |
| cccagcagca | gaagcagccc | tgcatcccac | cccctcagct | tcagcagcag | caggtgaaac | 120 |
| agccttgcca | gcctccacct | caggaaccat | gcatccccaa | aaccaaggag | ccctgccacc | 180 |
| ccaaggtgcc | tgagccctgc | caccccaaag | tgcctgagcc | ctgccagccc | aaggttccag | 240 |
| agccatgcca | ccccaaggtg | cctgagccct | gcccttcaat | agtcactcca | gcaccagccc | 300 |
| agcagaanac | caagcagaag | taatgtggtc | cacagccatg | cccttgagga | gccggccacc | 360 |
| agatgctgaa | tccctatcc | cattctgtgt | atgagtccca | tttgccttgc | aattagcatt | 420 |
| ctgtctcccc | caaaaaaaaa | a | | | | 441 |

<210> SEQ ID NO 98
<211> LENGTH: 600
<212> TYPE: DNA
<213> ORGANISM: Homo sapiens
<220> FEATURE:
<221> NAME/KEY: modified_base
<222> LOCATION: (285)
<223> OTHER INFORMATION: Where n is a, c, g or t
<221> NAME/KEY: modified_base
<222> LOCATION: (349)
<223> OTHER INFORMATION: Where n is a, c, g or t
<221> NAME/KEY: modified_base
<222> LOCATION: (489)
<223> OTHER INFORMATION: Where n is a, c, g or t
<221> NAME/KEY: modified_base
<222> LOCATION: (496)
<223> OTHER INFORMATION: Where n is a, c, g or t
<221> NAME/KEY: modified_base
<222> LOCATION: (583)
<223> OTHER INFORMATION: Where n is a, c, g or t

<400> SEQUENCE: 98

```
gtattcctct cttcacacca ggaccagcca ctgttgcagc atgagttccc agcagcagaa    60
gcagccctgc atcccacccc ctcagcttca gcagcagcag gtgaaacagc cttgccagcc   120
tccacctcag gaaccatgca tccccaaaac caaggagccc tgccaccccca aggtgcctga   180
gccctgccac cccaaagtgc ctgagccctg ccagcccaag gttccagagc catgccaccc   240
caaggtgcct gagccctgcc cttcaatagt cactccagca ccagcccagc agaanaccaa   300
gcagaagtaa tgtggtccac agccatgccc ttgaggagcc ggccaccana tgctgaatcc   360
cctatcccat tctgtgtatg agtcccattt gccttgcaat tagcattctg tctcccccaa   420
aaagaatgt gctatgaagc tttctttcct acacactctg agtctctgaa tgaagctgaa   480
ggtcttaant acaganctag ttttcagctg ctcagaattc tctgaagaaa agatttaaga   540
tgaaaggcaa atgattcagc tccttattac cccattaaat tcnctttcaa ttccaaaaaa   600
```

<210> SEQ ID NO 99
<211> LENGTH: 667
<212> TYPE: DNA
<213> ORGANISM: Homo sapiens
<220> FEATURE:
<221> NAME/KEY: modified_base
<222> LOCATION: (345)
<223> OTHER INFORMATION: Where n is a, c, g or t
<221> NAME/KEY: modified_base
<222> LOCATION: (562)
<223> OTHER INFORMATION: Where n is a, c, g or t
<221> NAME/KEY: modified_base
<222> LOCATION: (635)
<223> OTHER INFORMATION: Where n is a, c, g or t

<400> SEQUENCE: 99

```
actagtgact gagttcctgg caaagaaatt tgacctggac cagttgataa ctcatgtttt    60
accatttaaa aaaatcagtg aaggatttga gctgctcaat tcaggacaaa gcattcgaac   120
ggtcctgacg ttttgagatc caaagtggca ggaggtctgt gttgtcatgg tgaactggag   180
tttctcttgt gagagttccc tcatctgaaa tcatgtatct gtctcacaaa tacaagcata   240
agtagaagat ttgttgaaga catagaaccc ttataaagaa ttattaacct ttataaacat   300
ttaaagtctt gtgagcacct gggaattagt ataataacaa tgttnatatt tttgatttac   360
attttgtaag gctataattg tatcttttaa gaaaacatac cttggatttc tatgttgaaa   420
tggagatttt taagagtttt aaccagctgc tgcagatata ttactcaaaa cagatatagc   480
gtataaagat atagtaaatg catctcctag agtaatattc acttaacaca ttggaaacta   540
ttattttta gatttgaata tnaatgttat tttttaaaca cttgttatga gttacttggg   600
attacatttt gaaatcagtt cattccatga tgcanattac tgggattaga ttaagaaaga   660
cggaaaa                                                             667
```

<210> SEQ ID NO 100

<211> LENGTH: 583
<212> TYPE: DNA
<213> ORGANISM: Homo sapiens
<220> FEATURE:
<221> NAME/KEY: modified_base
<222> LOCATION: (404)
<223> OTHER INFORMATION: Where n is a, c, g or t
<221> NAME/KEY: modified_base
<222> LOCATION: (506)
<223> OTHER INFORMATION: Where n is a, c, g or t
<221> NAME/KEY: modified_base
<222> LOCATION: (514)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (528)
<223> OTHER INFORMATION: Where n is a, c, g or t
<221> NAME/KEY: modified_base
<222> LOCATION: (538)
<223> OTHER INFORMATION: Where n is a, c, g or t
<221> NAME/KEY: modified_base
<222> LOCATION: (548)
<223> OTHER INFORMATION: Where n is a, c, g or t
<221> NAME/KEY: modified_base
<222> LOCATION: (556)
<223> OTHER INFORMATION: Where n is a, c, g or t
<221> NAME/KEY: modified_base
<222> LOCATION: (568)
<223> OTHER INFORMATION: Where n is a, c, g or t
<221> NAME/KEY: modified_base
<222> LOCATION: (569)
<223> OTHER INFORMATION: Where n is a, c, g or t

<400> SEQUENCE: 100

| | | | | | |
|---|---|---|---|---|---|
| gttttgtttg | taagatgatc | acagtcatgt | tacactgatc | taaaggacat | atatataacc | 60 |
| ctttaaaaaa | aaaatcactg | cctcattctt | atttcaagat | gaatttctat | acagactaga | 120 |
| tgttttctg | aagatcaatt | agacattttg | aaaatgattt | aaagtgtttt | ccttaatgtt | 180 |
| ctctgaaaac | aagtttcttt | tgtagtttta | accaaaaaag | tgccctttt | gtcactggat | 240 |
| tctcctagca | ttcatgattt | ttttttcata | caatgaaatt | aaaattgcta | aaatcatgga | 300 |
| ctggctttct | ggttggattt | caggtaagat | gtgtttaagg | ccagagcttt | tctcagtatt | 360 |
| tgattttttt | ccccaatatt | tgatttttta | aaaatataca | catnggtgct | gcatttatat | 420 |
| ctgctggttt | aaaattctgt | catatttcac | ttctagcctt | ttagttatgg | caaatcatat | 480 |
| tttactttta | cttaaagcat | ttggtnattt | ggantatctg | gttctannct | aaaaaaanta | 540 |
| attctatnaa | ttgaantttt | ggtactcnnc | catatttgga | tcc | | 583 |

<210> SEQ ID NO 101
<211> LENGTH: 592
<212> TYPE: DNA
<213> ORGANISM: Homo sapiens
<220> FEATURE:
<221> NAME/KEY: modified_base
<222> LOCATION: (218)
<223> OTHER INFORMATION: Where n is a, c, g or t
<221> NAME/KEY: modified_base
<222> LOCATION: (497)
<223> OTHER INFORMATION: Where n is a, c, g or t
<221> NAME/KEY: modified_base
<222> LOCATION: (502)
<223> OTHER INFORMATION: Where n is a, c, g or t
<221> NAME/KEY: modified_base
<222> LOCATION: (533)
<223> OTHER INFORMATION: Where n is a, c, g or t
<221> NAME/KEY: modified_base
<222> LOCATION: (544)
<223> OTHER INFORMATION: Where n is a, c, g or t
<221> NAME/KEY: modified_base

```
<222> LOCATION: (546)
<223> OTHER INFORMATION: Where n is a, c, g or t
<221> NAME/KEY: modified_base
<222> LOCATION: (548)
<223> OTHER INFORMATION: Where n is a, c, g or t
<221> NAME/KEY: modified_base
<222> LOCATION: (550)
<223> OTHER INFORMATION: Where n is a, c, g or t
<221> NAME/KEY: modified_base
<222> LOCATION: (555)
<223> OTHER INFORMATION: Where n is a, c, g or t

<400> SEQUENCE: 101
gtggagacgt acaaagagca gccgctcaag acacctggga agaaaaagaa aggcaagccc      60
gggaaacgca aggagcagga aaagaaaaaa cggcgaactc gctctgcctg gttagactct    120
ggagtgactg ggagtgggct agaaggggac cacctgtctg acacctccac aacgtcgctg    180
gagctcgatt cacggaggca ttgaaatttt cagcaganac cttccaagga catattgcag    240
gattctgtaa tagtgaacat atggaaagta ttagaaatat ttattgtctg taaatactgt    300
aaatgcattg gaataaaact gtctccccca ttgctctatg aaactgcaca ttggtcattg    360
tgaatatttt ttttttttgcc aaggctaatc caattattat tatcacattt accataattt    420
attttgtcca ttgatgtatt tattttgtaa atgtatcttg gtgctgctga atttctatat    480
tttttgtaca taatgcnttt anatatacct atcaagtttg ttgataaatg acncaatgaa    540
gtgncncnan ttggnggttg aatttaatga atgcctaatt ttattatccc aa             592

<210> SEQ ID NO 102
<211> LENGTH: 587
<212> TYPE: DNA
<213> ORGANISM: Homo sapiens
<220> FEATURE:
<221> NAME/KEY: modified_base
<222> LOCATION: (91)
<223> OTHER INFORMATION: Where n is a, c, g or t
<221> NAME/KEY: modified_base
<222> LOCATION: (131)
<223> OTHER INFORMATION: Where n is a, c, g or t
<221> NAME/KEY: modified_base
<222> LOCATION: (256)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (332)
<223> OTHER INFORMATION: Where n is a, c, g or t
<221> NAME/KEY: modified_base
<222> LOCATION: (392)
<223> OTHER INFORMATION: Where n is a, c, g or t
<221> NAME/KEY: modified_base
<222> LOCATION: (400)
<223> OTHER INFORMATION: Where n is a, c, g or t
<221> NAME/KEY: modified_base
<222> LOCATION: (403)
<223> OTHER INFORMATION: Where n is a, c, g or t
<221> NAME/KEY: modified_base
<222> LOCATION: (441)
<223> OTHER INFORMATION: Where n is a, c, g or t
<221> NAME/KEY: modified_base
<222> LOCATION: (496)
<223> OTHER INFORMATION: Where n is a, c, g or t
<221> NAME/KEY: modified_base
<222> LOCATION: (497)
<223> OTHER INFORMATION: Where n is a, c, g or t
<221> NAME/KEY: modified_base
<222> LOCATION: (499)
<223> OTHER INFORMATION: Where n is a, c, g or t
<221> NAME/KEY: modified_base
<222> LOCATION: (510)
<223> OTHER INFORMATION: Where n is a, c, g or t
```

<210> SEQ ID NO 102 (continued)

<221> NAME/KEY: modified_base
<222> LOCATION: (511)
<223> OTHER INFORMATION: Where n is a, c, g or t
<221> NAME/KEY: modified_base
<222> LOCATION: (518)
<223> OTHER INFORMATION: Where n is a, c, g or t
<221> NAME/KEY: modified_base
<222> LOCATION: (519)
<223> OTHER INFORMATION: Where n is a, c, g or t
<221> NAME/KEY: modified_base
<222> LOCATION: (539)
<223> OTHER INFORMATION: Where n is a, c, g or t
<221> NAME/KEY: modified_base
<222> LOCATION: (554)
<223> OTHER INFORMATION: Where n is a, c, g or t
<221> NAME/KEY: modified_base
<222> LOCATION: (560)
<223> OTHER INFORMATION: Where n is a, c, g or t
<221> NAME/KEY: modified_base
<222> LOCATION: (566)
<223> OTHER INFORMATION: Where n is a, c, g or t

<400> SEQUENCE: 102

```
cgtcctaagc acttagacta catcagggaa gaacacagac cacatccctg tcctcatgcg      60
gcttatgttt tctggaagaa agtggagacc nagtccttgg ctttagggct ccccggctgg     120
gggctgtgca ntccggtcag ggcgggaagg gaaatgcacc gctgcatgtg aacttacagc     180
ccaggcggat gccccttccc ttagcactac ctggcctcct gcatcccctc gcctcatgtt     240
cctcccacct tcaaanaatg aanaacccca tgggcccagc cccttgccct ggggaaccaa     300
ggcagccttc caaaactcag gggctgaagc anactattag ggcaggggct gactttgggt     360
gacactgccc attccctctc agggcagctc angtcacccn ggnctcttga acccagcctg     420
ttcctttgaa aaagggcaaa actgaaaagg gcttttccta naaaaagaaa aaccagggaa     480
ctttgccagg gcttcnntnt taccaaaacn ncttctcnng gattttttaat tccccattng    540
gcctccactt accngggggcn atgccccaaa attaanaatt tcccatc                  587
```

<210> SEQ ID NO 103
<211> LENGTH: 496
<212> TYPE: DNA
<213> ORGANISM: Homo sapiens
<220> FEATURE:
<221> NAME/KEY: modified_base
<222> LOCATION: (2)
<223> OTHER INFORMATION: Where n is a, c, g or t
<221> NAME/KEY: modified_base
<222> LOCATION: (17)
<223> OTHER INFORMATION: Where n is a, c, g or t
<221> NAME/KEY: modified_base
<222> LOCATION: (66)
<223> OTHER INFORMATION: Where n is a, c, g or t
<221> NAME/KEY: modified_base
<222> LOCATION: (74)
<223> OTHER INFORMATION: Where n is a, c, g or t
<221> NAME/KEY: modified_base
<222> LOCATION: (82)
<223> OTHER INFORMATION: Where n is a, c, g or t
<221> NAME/KEY: modified_base
<222> LOCATION: (119)
<223> OTHER INFORMATION: Where n is a, c, g or t
<221> NAME/KEY: modified_base
<222> LOCATION: (164)
<223> OTHER INFORMATION: Where n is a, c, g or t
<221> NAME/KEY: modified_base
<222> LOCATION: (166)
<223> OTHER INFORMATION: Where n is a, c, g or t
<221> NAME/KEY: modified_base
<222> LOCATION: (172)
<223> OTHER INFORMATION: Where n is a, c, g or t
<221> NAME/KEY: modified_base
<222> LOCATION: (200)

```
<223> OTHER INFORMATION: Where n is a, c, g or t
<221> NAME/KEY: modified_base
<222> LOCATION: (203)
<223> OTHER INFORMATION: Where n is a, c, g or t
<221> NAME/KEY: modified_base
<222> LOCATION: (228)
<223> OTHER INFORMATION: Where n is a, c, g or t
<221> NAME/KEY: modified_base
<222> LOCATION: (232)
<223> OTHER INFORMATION: Where n is a, c, g or t
<221> NAME/KEY: modified_base
<222> LOCATION: (271)
<223> OTHER INFORMATION: Where n is a, c, g or t
<221> NAME/KEY: modified_base
<222> LOCATION: (273)
<223> OTHER INFORMATION: Where n is a, c, g or t
<221> NAME/KEY: modified_base
<222> LOCATION: (415)
<223> OTHER INFORMATION: Where n is a, c, g or t
<221> NAME/KEY: modified_base
<222> LOCATION: (423)
<223> OTHER INFORMATION: Where n is a, c, g or t
<221> NAME/KEY: modified_base
<222> LOCATION: (445)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (473)
<223> OTHER INFORMATION: Where n is a, c, g or t

<400> SEQUENCE: 103
anaggactgg ccctacntgc tctctctcgt cctacctatc aatgcccaac atggcagaac      60
ctgcanccct tggncactgc anatggaaac ctctcagtgt cttgacatca ccctacccnt     120
gcggtgggtc tccaccacaa ccactttgac tctgtggtcc ctgnanggtg gnttctcctg    180
actggcagga tggaccttan ccnacatatc cctctgttcc ctctgctnag anaaagaatt    240
cccttaacat gatataatcc acccatgcaa ntngctactg gcccagctac catttaccat    300
ttgcctacag aatttcattc agtctacact ttggcattct ctctggcgat agagtgtggc    360
tgggctgacc gcaaaaggtg ccttacacac tggcccccac cctcaaccgt tgacncatca    420
gangcttgcc tcctccttct gattnncccc catgttggat atcagggtgc tcnagggatt    480
ggaaaagaaa caaaac                                                     496

<210> SEQ ID NO 104
<211> LENGTH: 575
<212> TYPE: DNA
<213> ORGANISM: Homo sapiens
<220> FEATURE:
<221> NAME/KEY: modified_base
<222> LOCATION: (18)
<223> OTHER INFORMATION: Where n is a, c, g or t
<221> NAME/KEY: modified_base
<222> LOCATION: (19)
<223> OTHER INFORMATION: Where n is a, c, g or t
<221> NAME/KEY: modified_base
<222> LOCATION: (45)
<223> OTHER INFORMATION: Where n is a, c, g or t
<221> NAME/KEY: modified_base
<222> LOCATION: (68)
<223> OTHER INFORMATION: Where n is a, c, g or t
<221> NAME/KEY: modified_base
<222> LOCATION: (77)
<223> OTHER INFORMATION: Where n is a, c, g or t
<221> NAME/KEY: modified_base
<222> LOCATION: (132)
<223> OTHER INFORMATION: Where n is a, c, g or t
<221> NAME/KEY: modified_base
<222> LOCATION: (155)
<223> OTHER INFORMATION: Where n is a, c, g or t
```

-continued

```
<221> NAME/KEY: modified_base
<222> LOCATION: (174)
<223> OTHER INFORMATION: Where n is a, c, g or t
<221> NAME/KEY: modified_base
<222> LOCATION: (218)
<223> OTHER INFORMATION: Where n is a, c, g or t
<221> NAME/KEY: modified_base
<222> LOCATION: (226)
<223> OTHER INFORMATION: Where n is a, c, g or t
<221> NAME/KEY: modified_base
<222> LOCATION: (238)
<223> OTHER INFORMATION: Where n is a, c, g or t
<221> NAME/KEY: modified_base
<222> LOCATION: (259)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (271)
<223> OTHER INFORMATION: Where n is a, c, g or t
<221> NAME/KEY: modified_base
<222> LOCATION: (273)
<223> OTHER INFORMATION: Where n is a, c, g or t
<221> NAME/KEY: modified_base
<222> LOCATION: (306)
<223> OTHER INFORMATION: Where n is a, c, g or t
<221> NAME/KEY: modified_base
<222> LOCATION: (323)
<223> OTHER INFORMATION: Where n is a, c, g or t
<221> NAME/KEY: modified_base
<222> LOCATION: (339)
<223> OTHER INFORMATION: Where n is a, c, g or t
<221> NAME/KEY: modified_base
<222> LOCATION: (363)
<223> OTHER INFORMATION: Where n is a, c, g or t
<221> NAME/KEY: modified_base
<222> LOCATION: (368)
<223> OTHER INFORMATION: Where n is a, c, g or t
<221> NAME/KEY: modified_base
<222> LOCATION: (370)
<223> OTHER INFORMATION: Where n is a, c, g or t
<221> NAME/KEY: modified_base
<222> LOCATION: (378)
<223> OTHER INFORMATION: Where n is a, c, g or t
<221> NAME/KEY: modified_base
<222> LOCATION: (381)
<223> OTHER INFORMATION: Where n is a, c, g or t
<221> NAME/KEY: modified_base
<222> LOCATION: (382)
<223> OTHER INFORMATION: Where n is a, c, g or t
<221> NAME/KEY: modified_base
<222> LOCATION: (436)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (459)
<223> OTHER INFORMATION: Where n is a, c, g or t
<221> NAME/KEY: modified_base
<222> LOCATION: (460)
<223> OTHER INFORMATION: Where n is a, c, g or t
<221> NAME/KEY: modified_base
<222> LOCATION: (466)
<223> OTHER INFORMATION: Where n is a, c, g or t
<221> NAME/KEY: modified_base
<222> LOCATION: (481)
<223> OTHER INFORMATION: Where n is a, c, g or t
<221> NAME/KEY: modified_base
<222> LOCATION: (485)
<223> OTHER INFORMATION: Where n is a, c, g or t
<221> NAME/KEY: modified_base
<222> LOCATION: (496)
<223> OTHER INFORMATION: Where n is a, c, g or t
<221> NAME/KEY: modified_base
<222> LOCATION: (503)
<223> OTHER INFORMATION: Where n is a, c, g or t
<221> NAME/KEY: modified_base
```

```
<222> LOCATION: (510)
<223> OTHER INFORMATION: Where n is a, c, g or t
<221> NAME/KEY: modified_base
<222> LOCATION: (512)
<223> OTHER INFORMATION: Where n is a, c, g or t
<221> NAME/KEY: modified_base
<222> LOCATION: (515)
<223> OTHER INFORMATION: Where n is a, c, g or t
<221> NAME/KEY: modified_base
<222> LOCATION: (528)
<223> OTHER INFORMATION: Where n is a, c, g or t
<221> NAME/KEY: modified_base
<222> LOCATION: (542)
<223> OTHER INFORMATION: Where n is a, c, g or t
<221> NAME/KEY: modified_base
<222> LOCATION: (552)
<223> OTHER INFORMATION: Where n is a, c, g or t

<400> SEQUENCE: 104
gcacctgctc tcaatccnnc tctcaccatg atcctccgcc tgcanaaact cctctgccaa      60
ctatggangt ggtttcnggg gtggctcttg ccaactggga agaagccgtg gtgtctctac     120
ctgttcaact cngtttgtgt ctgggggatc aactngggc tatggaagcg gctnaactgt      180
tgttttggtg aagggctgg taattggctt tgggaagtng cttatngaag ttggcctngg      240
gaagttgcta ttgaaagtng ccntggaagt ngntttggtg gggggttttg ctggtggcct     300
ttgttnaatt tgggtgcttt gtnaatgcg gcccctcnc ctgggcaatg aaaaaaatca       360
ccnatgcngn aaacctcnac nnaacagcct gggcttccct cacctcgaaa aagttgctc      420 cccccccaaa aaaggncaan ccctcaann tggaangttg aaaaaatcct cgaatgggga     480
ncccnaaaac aaaaanccc ccntttcccn gnaanggggg aaataccncc cccccactta     540
cnaaaaccct tntaaaaaac ccccgggaa aaaaa                                 575

<210> SEQ ID NO 105
<211> LENGTH: 619
<212> TYPE: DNA
<213> ORGANISM: Homo sapiens
<220> FEATURE:
<221> NAME/KEY: modified_base
<222> LOCATION: (260)
<223> OTHER INFORMATION: Where n is a, c, g or t
<221> NAME/KEY: modified_base
<222> LOCATION: (527)
<223> OTHER INFORMATION: Where n is a, c, g or t
<221> NAME/KEY: modified_base
<222> LOCATION: (560)
<223> OTHER INFORMATION: Where n is a, c, g or t
<221> NAME/KEY: modified_base
<222> LOCATION: (564)
<223> OTHER INFORMATION: Where n is a, c, g or t
<221> NAME/KEY: modified_base
<222> LOCATION: (566)
<223> OTHER INFORMATION: Where n is a, c, g or t
<221> NAME/KEY: modified_base
<222> LOCATION: (575)
<223> OTHER INFORMATION: Where n is a, c, g or t
<221> NAME/KEY: modified_base
<222> LOCATION: (599)
<223> OTHER INFORMATION: Where n is a, c, g or t

<400> SEQUENCE: 105
cactagtagg atagaaacac tgtgtcccga gagtaaggag agaagctact attgattaga      60
gcctaaccca ggttaactgc aagaagaggc gggatacttt cagctttcca tgtaactgta    120
tgcataaagc caatgtagtc cagtttctaa gatcatgttc caagctaact gaatcccact    180
tcaatacaca ctcatgaact cctgatggaa caataacagg cccaagcctg tggtatgatg    240
tgcacacttg ctagactcan aaaaaatact actctcataa atgggtggga gtattttggt    300
```

```
gacaacctac tttgcttggc tgagtgaagg aatgatattc atatattcat ttattccatg    360
gacatttagt tagtgctttt tatataccag gcatgatgct gagtgacact cttgtgtata    420
tttccaaatt tttgtacagt cgctgcacat atttgaaatc atatattaag acttccaaaa    480
aatgaagtcc ctggttttc atggcaactt gatcagtaaa ggattcncct ctgtttggta     540
cttaaaacat ctactatatn gttnanatga aattccttt ccccncctcc cgaaaaaana    600
aagtggtggg gaaaaaaaa                                                 619
```

```
<210> SEQ ID NO 106
<211> LENGTH: 506
<212> TYPE: DNA
<213> ORGANISM: Homo sapiens
<220> FEATURE:
<221> NAME/KEY: modified_base
<222> LOCATION: (8)
<223> OTHER INFORMATION: Where n is a, c, g or t
<221> NAME/KEY: modified_base
<222> LOCATION: (21)
<223> OTHER INFORMATION: Where n is a, c, g or t
<221> NAME/KEY: modified_base
<222> LOCATION: (31)
<223> OTHER INFORMATION: Where n is a, c, g or t
<221> NAME/KEY: modified_base
<222> LOCATION: (32)
<223> OTHER INFORMATION: Where n is a, c, g or t
<221> NAME/KEY: modified_base
<222> LOCATION: (58)
<223> OTHER INFORMATION: Where n is a, c, g or t
<221> NAME/KEY: modified_base
<222> LOCATION: (75)
<223> OTHER INFORMATION: Where n is a, c, g or t
<221> NAME/KEY: modified_base
<222> LOCATION: (89)
<223> OTHER INFORMATION: Where n is a, c, g or t
<221> NAME/KEY: modified_base
<222> LOCATION: (96)
<223> OTHER INFORMATION: Where n is a, c, g or t
<221> NAME/KEY: modified_base
<222> LOCATION: (99)
<223> OTHER INFORMATION: Where n is a, c, g or t
<221> NAME/KEY: modified_base
<222> LOCATION: (103)
<223> OTHER INFORMATION: Where n is a, c, g or t
<221> NAME/KEY: modified_base
<222> LOCATION: (122)
<223> OTHER INFORMATION: Where n is a, c, g or t
<221> NAME/KEY: modified_base
<222> LOCATION: (126)
<223> OTHER INFORMATION: Where n is a, c, g or t
<221> NAME/KEY: modified_base
<222> LOCATION: (147)
<223> OTHER INFORMATION: Where n is a, c, g or t
<221> NAME/KEY: modified_base
<222> LOCATION: (150)
<223> OTHER INFORMATION: Where n is a, c, g or t
<221> NAME/KEY: modified_base
<222> LOCATION: (158)
<223> OTHER INFORMATION: Where n is a, c, g or t
<221> NAME/KEY: modified_base
<222> LOCATION: (195)
<223> OTHER INFORMATION: Where n is a, c, g or t
<221> NAME/KEY: modified_base
<222> LOCATION: (210)
<223> OTHER INFORMATION: Where n is a, c, g or t
<221> NAME/KEY: modified_base
<222> LOCATION: (212)
<223> OTHER INFORMATION: Where n is a, c, g or t
<221> NAME/KEY: modified_base
<222> LOCATION: (219)
<223> OTHER INFORMATION: Where n is a, c, g or t
<221> NAME/KEY: modified_base
<222> LOCATION: (226)
<223> OTHER INFORMATION: Where n is a, c, g or t
```

<221> NAME/KEY: modified_base
<222> LOCATION: (246)
<223> OTHER INFORMATION: Where n is a, c, g or t
<221> NAME/KEY: modified_base
<222> LOCATION: (248)
<223> OTHER INFORMATION: Where n is a, c, g or t
<221> NAME/KEY: modified_base
<222> LOCATION: (249)
<223> OTHER INFORMATION: Where n is a, c, g or t
<221> NAME/KEY: modified_base
<222> LOCATION: (255)
<223> OTHER INFORMATION: Where n is a, c, g or t
<221> NAME/KEY: modified_base
<222> LOCATION: (258)
<223> OTHER INFORMATION: Where n is a, c, g or t
<221> NAME/KEY: modified_base
<222> LOCATION: (261)
<223> OTHER INFORMATION: Where n is a, c, g or t
<221> NAME/KEY: modified_base
<222> LOCATION: (263)
<223> OTHER INFORMATION: Where n is a, c, g or t
<221> NAME/KEY: modified_base
<222> LOCATION: (265)
<223> OTHER INFORMATION: Where n is a, c, g or t
<221> NAME/KEY: modified_base
<222> LOCATION: (275)
<223> OTHER INFORMATION: Where n is a, c, g or t
<221> NAME/KEY: modified_base
<222> LOCATION: (304)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (321)
<223> OTHER INFORMATION: Where n is a, c, g or t
<221> NAME/KEY: modified_base
<222> LOCATION: (331)
<223> OTHER INFORMATION: Where n is a, c, g or t
<221> NAME/KEY: modified_base
<222> LOCATION: (337)
<223> OTHER INFORMATION: Where n is a, c, g or t
<221> NAME/KEY: modified_base
<222> LOCATION: (340)
<223> OTHER INFORMATION: Where n is a, c, g or t
<221> NAME/KEY: modified_base
<222> LOCATION: (358)
<223> OTHER INFORMATION: Where n is a, c, g or t
<221> NAME/KEY: modified_base
<222> LOCATION: (371)
<223> OTHER INFORMATION: Where n is a, c, g or t
<221> NAME/KEY: modified_base
<222> LOCATION: (377)
<223> OTHER INFORMATION: Where n is a, c, g or t
<221> NAME/KEY: modified_base
<222> LOCATION: (380)
<223> OTHER INFORMATION: Where n is a, c, g or t
<221> NAME/KEY: modified_base
<222> LOCATION: (396)
<223> OTHER INFORMATION: Where n is a, c, g or t
<221> NAME/KEY: modified_base
<222> LOCATION: (450)
<223> OTHER INFORMATION: Where n is a, c, g or t
<221> NAME/KEY: modified_base
<222> LOCATION: (491)
<223> OTHER INFORMATION: Where n is a, c, g or t

<400> SEQUENCE: 106
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgccccngt gtcagaggct catattgtgt      180
tatgtaaatg gtatntcatt cgctactatn antcaattg aaatanggtc tttgggttat      240
gaatantnng cagcncanct nanangctgt ctgtngtatt cattgtggtc atagcacctc     300

```
acancattgt aacctcnatc nagtgagaca nactagnaan ttcctagtga tggctcanga    360
ttccaaatgg nctcatntcn aatgtttaaa agttanttaa gtgtaagaaa tacagactgg    420
atgttccacc aactagtacc tgtaatgacn ggcctgtccc aacacatctc ccttttccat    480
gactgtggta ncccgcatcg gaaaaa                                         506
```

<210> SEQ ID NO 107
<211> LENGTH: 452
<212> TYPE: DNA
<213> ORGANISM: Homo sapiens
<220> FEATURE:
<221> NAME/KEY: modified_base
<222> LOCATION: (289)
<223> OTHER INFORMATION: Where n is a, c, g or t
<221> NAME/KEY: modified_base
<222> LOCATION: (317)
<223> OTHER INFORMATION: Where n is a, c, g or t
<221> NAME/KEY: modified_base
<222> LOCATION: (378)
<223> OTHER INFORMATION: Where n is a, c, g or t
<400> SEQUENCE: 107

```
gttgagtctg tactaaacag taagatatct caatgaacca taaattcaac tttgtaaaaa    60
tcttttgaag catagataat attgtttggt aaatgtttct tttgtttggt aaatgtttct    120
tttaaagacc ctcctattct ataaaactct gcatgtagag gcttgtttac ctttctctct    180
ctaaggttta caataggagt ggtgatttga aaaatataaa attatgagat tggttttcct    240
gtggcataaa ttgcatcact gtatcatttt ctttttttaac cggtaagant ttcagtttgt    300
tggaaagtaa ctgtganaac ccagtttccc gtccatctcc cttagggact acccatagaa    360
catgaaaagg tccccacnga agcaagaaga taagtctttc atggctgctg gttgcttaaa    420
ccactttaaa accaaaaaat tccccttgga aa                                   452
```

<210> SEQ ID NO 108
<211> LENGTH: 502
<212> TYPE: DNA
<213> ORGANISM: Homo sapiens
<220> FEATURE:
<221> NAME/KEY: modified_base
<222> LOCATION: (22)
<223> OTHER INFORMATION: Where n is a, c, g or t
<221> NAME/KEY: modified_base
<222> LOCATION: (31)
<223> OTHER INFORMATION: Where n is a, c, g or t
<221> NAME/KEY: modified_base
<222> LOCATION: (126)
<223> OTHER INFORMATION: Where n is a, c, g or t
<221> NAME/KEY: modified_base
<222> LOCATION: (168)
<223> OTHER INFORMATION: Where n is a, c, g or t
<221> NAME/KEY: modified_base
<222> LOCATION: (183)
<223> OTHER INFORMATION: Where n is a, c, g or t
<221> NAME/KEY: modified_base
<222> LOCATION: (205)
<223> OTHER INFORMATION: Where n is a, c, g or t
<221> NAME/KEY: modified_base
<222> LOCATION: (219)
<223> OTHER INFORMATION: Where n is a, c, g or t
<221> NAME/KEY: modified_base
<222> LOCATION: (231)
<223> OTHER INFORMATION: Where n is a, c, g or t
<221> NAME/KEY: modified_base
<222> LOCATION: (236)
<223> OTHER INFORMATION: Where n is a, c, g or t
<221> NAME/KEY: modified_base
<222> LOCATION: (259)
<223> OTHER INFORMATION: Where n is a, c, g or t
<221> NAME/KEY: modified_base

```
<222> LOCATION: (283)
<223> OTHER INFORMATION: Where n is a, c, g or t
<221> NAME/KEY: modified_base
<222> LOCATION: (295)
<223> OTHER INFORMATION: Where n is a, c, g or t
<221> NAME/KEY: modified_base
<222> LOCATION: (296)
<223> OTHER INFORMATION: Where n is a, c, g or t
<221> NAME/KEY: modified_base
<222> LOCATION: (298)
<223> OTHER INFORMATION: Where n is a, c, g or t
<221> NAME/KEY: modified_base
<222> LOCATION: (301)
<223> OTHER INFORMATION: Where n is a, c, g or t
<221> NAME/KEY: modified_base
<222> LOCATION: (340)
<223> OTHER INFORMATION: Where n is a, c, g or t
<221> NAME/KEY: modified_base
<222> LOCATION: (354)
<223> OTHER INFORMATION: Where n is a, c, g or t
<221> NAME/KEY: modified_base
<222> LOCATION: (378)
<223> OTHER INFORMATION: Where n is a, c, g or t
<221> NAME/KEY: modified_base
<222> LOCATION: (383)
<223> OTHER INFORMATION: Where n is a, c, g or t
<221> NAME/KEY: modified_base
<222> LOCATION: (409)
<223> OTHER INFORMATION: Where n is a, c, g or t
<221> NAME/KEY: modified_base
<222> LOCATION: (433)
<223> OTHER INFORMATION: Where n is a, c, g or t
<221> NAME/KEY: modified_base
<222> LOCATION: (446)
<223> OTHER INFORMATION: Where n is a, c, g or t
<221> NAME/KEY: modified_base
<222> LOCATION: (455)
<223> OTHER INFORMATION: Where n is a, c, g or t
<221> NAME/KEY: modified_base
<222> LOCATION: (466)
<223> OTHER INFORMATION: Where n is a, c, g or t
<221> NAME/KEY: modified_base
<222> LOCATION: (488)
<223> OTHER INFORMATION: Where n is a, c, g or t

<400> SEQUENCE: 108
atcttcttcc cttaattagt tnttatttat ntattaaatt ttattgcatg tcctggcaaa      60
caaaaagaga ttgtagattg gcttctggct ccccaaaagc ccataacaga aagtaccaca     120
agaccncaac tgaagcttaa aaaatctatc acatgtataa tacctttnga agaacattaa    180
tanagcatat aaaacttta acatntgctt aatgttgtnc aattataaaa ntaatngaaa     240
aaaatgtccc tttaacatnc aatatcccac atagtgttat ttnaggggat taccnngnaa    300 naaaaaagg gtagaaggga tttaatgaaa actctgcttn ccatttctgt ttanaaacgt     360
ctccagaaca aaaacttntc aantctttca gctaaccgca tttgagctna ggccactcaa    420
aaactccatt agnccccactt tctaanggtc tctanagctt actaanccctt ttgacccctt  480 accctggnta ctcctgccct ca                                              502

<210> SEQ ID NO 109
<211> LENGTH: 1308
<212> TYPE: DNA
<213> ORGANISM: Homo sapiens

<400> SEQUENCE: 109
acccgaggtc tcgctaaaat catcatggat tcacttggcg ccgtcagcac tcgacttggg     60
tttgatcttt tcaaagagct gaagaaaaca aatgatggca acatcttctt ttcccctgtg    120
ggcatcttga ctgcaattgg catggtcctc ctggggaccc gaggagccac cgcttcccag    180
```

-continued

```
ttggaggagg tgtttcactc tgaaaaagag acgaagagct caagaataaa ggctgaagaa      240
aaagaggtga ttgagaacac agaagcagta catcaacaat tccaaaagtt tttgactgaa      300
ataagcaaac tcactaatga ttatgaactg aacataacca acaggctgtt tggagaaaaa      360
acatacctct tccttcaaaa atacttagat tatgttgaaa aatattatca tgcatctctg      420
gaacctgttg attttgtaaa tgcagccgat gaaagtcgaa agaagattaa ttcctgggtt      480
gaaagcaaaa caaatgaaaa aatcaaggac ttgttcccag atggctctat tagtagctct      540
accaagctgt tgctggtgaa catggtttat tttaaagggc aatgggacag ggagtttaag      600
aaagaaaata ctaaggaaga gaattttggg atgaataaga gcacaagtaa atctgtacag      660
atgatgacac agagccattc ctttagcttc actttcctgg aggacttgca ggccaaaatt      720
ctagggattc catataaaaa caacgaccta agcatgtttg tgcttctgcc caacgacatc      780
gatggcctgg agaagataat agataaaata agtcctgaga aattggtaga gtggactagt      840
ccagggcata tggaagaaag aaaggtgaat ctgcacttgc cccggtttga ggtggaggac      900
agttacgatc tagaggcggt cctggctgcc atggggatgg gcgatgcctt cagtgagcac      960
aaagccgact actcgggaat gtcgtcaggc tccggggttgt acgcccagaa gttcctgcac     1020
agttcctttg tggcagtaac tgaggaaggc accgaggctg cagctgccac tggcataggc     1080
tttactgtca catccgcccc aggtcatgaa atgttcact gcaatcatcc cttcctgttc      1140
ttcatcaggc acaatgaatc caacagcatc ctcttcttcg gcagattttc ttctccttaa     1200
gatgatcgtt gccatggcat tgctgctttt agcaaaaaac aactaccagt gttactcata     1260
tgattatgaa aatcgtccat tcttttaaat ggtggctcac ttgcattt                   1308
```

<210> SEQ ID NO 110
<211> LENGTH: 391
<212> TYPE: PRT
<213> ORGANISM: Homo sapiens

<400> SEQUENCE: 110

```
Met Asp Ser Leu Gly Ala Val Ser Thr Arg Leu Gly Phe Asp Leu Phe
 1               5                  10                  15
Lys Glu Leu Lys Lys Thr Asn Asp Gly Asn Ile Phe Phe Ser Pro Val
                20                  25                  30
Gly Ile Leu Thr Ala Ile Gly Met Val Leu Leu Gly Thr Arg Gly Ala
            35                  40                  45
Thr Ala Ser Gln Leu Glu Glu Val Phe His Ser Glu Lys Glu Thr Lys
        50                  55                  60
Ser Ser Arg Ile Lys Ala Glu Glu Lys Glu Val Ile Glu Asn Thr Glu
65                  70                  75                  80
Ala Val His Gln Gln Phe Gln Lys Phe Leu Thr Glu Ile Ser Lys Leu
                85                  90                  95
Thr Asn Asp Tyr Glu Leu Asn Ile Thr Asn Arg Leu Phe Gly Glu Lys
                100                 105                 110
Thr Tyr Leu Phe Leu Gln Lys Tyr Leu Asp Tyr Val Glu Lys Tyr Tyr
            115                 120                 125
His Ala Ser Leu Glu Pro Val Asp Phe Val Asn Ala Ala Asp Glu Ser
        130                 135                 140
Arg Lys Lys Ile Asn Ser Trp Val Glu Ser Lys Thr Asn Glu Lys Ile
145                 150                 155                 160
Lys Asp Leu Phe Pro Asp Gly Ser Ile Ser Ser Thr Lys Leu Val
                165                 170                 175
```

-continued

```
Leu Val Asn Met Val Tyr Phe Lys Gly Gln Trp Asp Arg Glu Phe Lys
            180                 185                 190
Lys Glu Asn Thr Lys Glu Lys Phe Trp Met Asn Lys Ser Thr Ser
        195                 200                 205
Lys Ser Val Gln Met Met Thr Gln Ser His Ser Phe Ser Phe Thr Phe
    210                 215                 220
Leu Glu Asp Leu Gln Ala Lys Ile Leu Gly Ile Pro Tyr Lys Asn Asn
225                 230                 235                 240
Asp Leu Ser Met Phe Val Leu Pro Asn Asp Ile Asp Gly Leu Glu
                245                 250                 255
Lys Ile Ile Asp Lys Ile Ser Pro Glu Lys Leu Val Glu Trp Thr Ser
                260                 265                 270
Pro Gly His Met Glu Glu Arg Lys Val Asn Leu His Leu Pro Arg Phe
            275                 280                 285
Glu Val Glu Asp Ser Tyr Asp Leu Glu Ala Val Leu Ala Ala Met Gly
        290                 295                 300
Met Gly Asp Ala Phe Ser Glu His Lys Ala Asp Tyr Ser Gly Met Ser
305                 310                 315                 320
Ser Gly Ser Gly Leu Tyr Ala Gln Lys Phe Leu His Ser Ser Phe Val
                325                 330                 335
Ala Val Thr Glu Glu Gly Thr Glu Ala Ala Ala Thr Gly Ile Gly
            340                 345                 350
Phe Thr Val Thr Ser Ala Pro Gly His Glu Asn Val His Cys Asn His
        355                 360                 365
Pro Phe Leu Phe Phe Ile Arg His Asn Glu Ser Asn Ser Ile Leu Phe
    370                 375                 380
Phe Gly Arg Phe Ser Ser Pro
385                 390

<210> SEQ ID NO 111
<211> LENGTH: 1419
<212> TYPE: DNA
<213> ORGANISM: Homo sapiens

<400> SEQUENCE: 111
ggagaactat aaattaagga tcccagctac ttaattgact tatgcttcct agttcgttgc     60
ccagccacca ccgtctctcc aaaaacccga ggtctcgcta aaatcatcat ggattcactt    120
ggcgccgtca gcactcgact tgggtttgat cttttcaaag agctgaagaa acaaatgat    180 ggcaacatct tcttttcccc tgtgggcatc ttgactgcaa ttggcatggt cctcctgggg    240
acccgaggag ccaccgcttc ccagttggag gaggtgtttc actctgaaaa agagacgaag    300
agctcaagaa taaaggctga agaaaaagag gtggtaagaa taaaggctga aggaaaagag    360
attgagaaca cagaagcagt acatcaacaa ttccaaaagt ttttgactga aataagcaaa    420
ctcactaatg attatgaact gaacataacc aacaggctgt ttggagaaaa acatacctc    480 ttccttcaaa aatacttaga ttatgttgaa aaatattatc atgcatctct ggaacctgtt    540
gattttgtaa atgcagccga tgaaagtcga agaagattaa ttcctgggt tgaaagcaaa    600 acaaatgaaa aaatcaagga cttgttccca gatggctcta ttagtagctc taccaagctg    660
gtgctggtga acatggttta ttttaagggg caatgggaca gggagtttaa gaaagaaaat    720
actaaggaag agaaattttg gatgaataag agcacaagta atctgtaca gatgatgaca    780 cagagccatt cctttagctt cactttcctg gaggacttgc aggccaaaat tctagggatt    840
ccatataaaa acaacgacct aagcatgttt gtgcttctgc ccaacgacat cgatggcctg    900
```

-continued

```
gagaagataa tagataaaat aagtcctgag aaattggtag agtggactag tccagggcat     960
atggaagaaa gaaggtgaaa tctgcacttg ccccggtttg aggtggagga cagttacgat    1020
ctagaggcgg tcctggctgc catggggatg ggcgatgcct tcagtgagca caaagccgac    1080
tactcgggaa tgtcgtcagg ctccgggttg tacgcccaga agttcctgca cagttccttt    1140
gtggcagtaa ctgaggaagg caccgaggct gcagctgcca ctggcatagg ctttactgtc    1200
acatccgccc caggtcatga aaatgttcac tgcaatcatc ccttcctgtt cttcatcagg    1260
cacaatgaat ccaacagcat cctcttcttc ggcagatttt cttctcctta agatgatcgt    1320
tgccatggca ttgctgcttt tagcaaaaaa caactaccag tgttactcat atgattatga    1380
aaatcgtcca ttcttttaaa tggtggctca cttgcattt                           1419
```

<210> SEQ ID NO 112
<211> LENGTH: 400
<212> TYPE: PRT
<213> ORGANISM: Homo sapiens

<400> SEQUENCE: 112

```
Met Asp Ser Leu Gly Ala Val Ser Thr Arg Leu Gly Phe Asp Leu Phe
  1               5                  10                  15

Lys Glu Leu Lys Lys Thr Asn Asp Gly Asn Ile Phe Phe Ser Pro Val
             20                  25                  30

Gly Ile Leu Thr Ala Ile Gly Met Val Leu Leu Gly Thr Arg Gly Ala
         35                  40                  45

Thr Ala Ser Gln Leu Glu Glu Val Phe His Ser Glu Lys Glu Thr Lys
     50                  55                  60

Ser Ser Arg Ile Lys Ala Glu Glu Lys Glu Val Val Arg Ile Lys Ala
 65                  70                  75                  80

Glu Gly Lys Glu Ile Glu Asn Thr Glu Ala Val His Gln Gln Phe Gln
                 85                  90                  95

Lys Phe Leu Thr Glu Ile Ser Lys Leu Thr Asn Asp Tyr Glu Leu Asn
            100                 105                 110

Ile Thr Asn Arg Leu Phe Gly Glu Lys Thr Tyr Leu Phe Leu Gln Lys
        115                 120                 125

Tyr Leu Asp Tyr Val Glu Lys Tyr Tyr His Ala Ser Leu Glu Pro Val
    130                 135                 140

Asp Phe Val Asn Ala Ala Asp Glu Ser Arg Lys Lys Ile Asn Ser Trp
145                 150                 155                 160

Val Glu Ser Lys Thr Asn Glu Lys Ile Lys Asp Leu Phe Pro Asp Gly
                165                 170                 175

Ser Ile Ser Ser Thr Lys Leu Val Leu Val Asn Met Val Tyr Phe
            180                 185                 190

Lys Gly Gln Trp Asp Arg Glu Phe Lys Lys Glu Asn Thr Lys Glu Glu
        195                 200                 205

Lys Phe Trp Met Asn Lys Ser Thr Ser Lys Ser Val Gln Met Met Thr
    210                 215                 220

Gln Ser His Ser Phe Ser Phe Thr Phe Leu Glu Asp Leu Gln Ala Lys
225                 230                 235                 240

Ile Leu Gly Ile Pro Tyr Lys Asn Asn Asp Leu Ser Met Phe Val Leu
                245                 250                 255

Leu Pro Asn Asp Ile Asp Gly Leu Glu Lys Ile Ile Asp Lys Ile Ser
            260                 265                 270

Pro Glu Lys Leu Val Glu Trp Thr Ser Pro Gly His Met Glu Glu Arg
```

```
            275                 280                 285
Lys Val Asn Leu His Leu Pro Arg Phe Glu Val Glu Asp Ser Tyr Asp
        290                 295                 300

Leu Glu Ala Val Leu Ala Ala Met Gly Met Gly Asp Ala Phe Ser Glu
305                 310                 315                 320

His Lys Ala Asp Tyr Ser Gly Met Ser Ser Gly Ser Gly Leu Tyr Ala
                325                 330                 335

Gln Lys Phe Leu His Ser Ser Phe Val Ala Val Thr Glu Glu Gly Thr
            340                 345                 350

Glu Ala Ala Ala Ala Thr Gly Ile Gly Phe Thr Val Thr Ser Ala Pro
        355                 360                 365

Gly His Glu Asn Val His Cys Asn His Pro Phe Leu Phe Phe Ile Arg
    370                 375                 380

His Asn Glu Ser Asn Ser Ile Leu Phe Phe Gly Arg Phe Ser Ser Pro
385                 390                 395                 400
```

<210> SEQ ID NO 113
<211> LENGTH: 957
<212> TYPE: DNA
<213> ORGANISM: Homo sapiens

<400> SEQUENCE: 113

```
ctcgaccttc tctgcacagc ggatgaaccc tgagcagctg aagaccagaa aagccactat    60
gactttctgc ttaattcagg agcttacagg attcttcaaa gagtgtgtcc agcatccttt   120
gaaacatgag ttcttaccag cagaagcaga cctttacccc accacctcag cttcaacagc   180
agcaggtgaa acaacccagc cagcctccac ctcaggaaat atttgttccc acaaccaagg   240
agccatgcca ctcaaaggtt ccacaacctg gaaacacaaa gattccagag ccaggctgta   300
ccaaggtccc tgagccaggc tgtaccaagg tccctgagcc aggttgtacc aaggtccctg   360
agccaggatg taccaaggtc cctgagccag gttgtaccaa ggtccctgag ccaggctaca   420
ccaaggtccc tgagccaggc agcatcaagg tccctgacca aggcttcatc aagtttcctg   480
agccaggtgc catcaaagtt cctgagcaag gatacaccaa agttcctgtg ccaggctaca   540
caaaggtacc agagccatgt ccttcaacgg tcactccagg cccagctcag cagaagacca   600
agcagaagta atttggtgca cagacaagcc cttgagaagc caaccaccag atgctggaca   660
ccctcttccc atctgttttct gtgtcttaat tgtctgtaga ccttgtaatc agtacattct   720
cacccccaagc catagtctct ctcttatttg tatcctaaaa atacggtact ataaagcttt   780
tgttcacaca cactctgaag aatcctgtaa gcccctgaat taagcagaaa gtcttcatgg   840
cttttctggt cttcggctgc tcagggttca tctgaagatt cgaatgaaaa gaaatgcatg   900
tttcctgctc tgccctcatt aaattgcttt taattccaaa aaaaaaaaaa aaaaaaa     957
```

<210> SEQ ID NO 114
<211> LENGTH: 161
<212> TYPE: PRT
<213> ORGANISM: Homo sapiens

<400> SEQUENCE: 114

```
Met Ser Ser Tyr Gln Gln Lys Gln Thr Phe Thr Pro Pro Gln Leu
1                5                  10                 15

Gln Gln Gln Gln Val Lys Gln Pro Ser Gln Pro Pro Gln Glu Ile
            20                 25                  30

Phe Val Pro Thr Thr Lys Glu Pro Cys His Ser Lys Val Pro Gln Pro
        35                 40                  45
```

-continued

```
Gly Asn Thr Lys Ile Pro Glu Pro Gly Cys Thr Lys Val Pro Glu Pro
    50                  55                  60

Gly Cys Thr Lys Val Pro Glu Pro Gly Cys Thr Lys Val Pro Glu Pro
65                  70                  75                  80

Gly Cys Thr Lys Val Pro Glu Pro Gly Cys Thr Lys Val Pro Glu Pro
                85                  90                  95

Gly Tyr Thr Lys Val Pro Glu Pro Gly Ser Ile Lys Val Pro Asp Gln
            100                 105                 110

Gly Phe Ile Lys Phe Pro Glu Pro Gly Ala Ile Lys Val Pro Glu Gln
        115                 120                 125

Gly Tyr Thr Lys Val Pro Val Pro Gly Tyr Thr Lys Val Pro Glu Pro
    130                 135                 140

Cys Pro Ser Thr Val Thr Pro Gly Pro Ala Gln Gln Lys Thr Lys Gln
145                 150                 155                 160

Lys
```

COMPOUNDS AND METHODS FOR THERAPY OF LUNG CANCER

REFERENCE TO RELATED APPLICATIONS

This application is a continuation-in-part of U.S. patent application No. 09/040,802, filed Mar. 18, 1998.

TECHNICAL FIELD

The present invention relates generally to compositions and methods for the treatment of lung cancer. The invention is more specifically related to nucleotide sequences that are preferentially expressed in lung tumor tissue, together with polypeptides encoded by such nucleotide sequences. The inventive nucleotide sequences and polypeptides may be used in vaccines and pharmaceutical compositions for the treatment of lung cancer.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compounds and methods for the therapy of lung cancer. In a first aspect, isolated DNA molecules encoding lung tumor polypeptides are provided, such DNA molecules comprising a nucleotide sequence selected from the group consisting of: (a) sequences provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111 and 113; (b) sequences complementary to a sequence provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111 and 113; and (b) sequences that hybridize to a sequence of (a) or (b) under moderately stringent conditions.

In a second aspect, isolated polypeptides are provided that comprise at least an immunogenic portion of a lung tumor protein or a variant thereof. In specific embodiments, such polypeptides comprise an amino acid sequence encoded by a DNA sequence comprising a nucleotide sequence selected from the group consisting of (a) sequences recited in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111 and 113; (b) sequences complementary to a sequence provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111 and 113; and (c) sequences that hybridize to a sequence of (a) or (b) under moderately stringent conditions.

In related aspects, expression vectors comprising the inventive DNA molecules, together with host cells transformed or transfected with such expression vectors are provided. In preferred embodiments, the host cells are selected from the group consisting of E. coli, yeast and mammalian cells.

In another aspect, fusion proteins comprising a first and a second inventive polypeptide or, alternatively, an inventive polypeptide and a known lung tumor antigen, are provided.

The present invention further provides pharmaceutical compositions comprising one or more of the above polypeptides, fusion proteins or DNA molecules and a physiologically acceptable carrier, together with vaccines comprising one or more such polypeptides, fusion proteins or DNA molecules in combination with an immune response enhancer.

In related aspects, the present invention provides methods for inhibiting the development of lung cancer in a patient, comprising administering to a patient an effective amount of at least one of the above pharmaceutical compositions and/or vaccines.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the therapy of lung cancer. The compositions described herein include polypeptides, fusion proteins and DNA molecules. Also included within the present invention are molecules (such as an antibody or fragment thereof) that bind to the inventive polypeptides. Such molecules are referred to herein as "binding agents."

In one aspect, the subject invention discloses polypeptides comprising an immunogenic portion of a human lung tumor protein, wherein the lung tumor protein includes an amino acid sequence encoded by a DNA molecule including a sequence selected from the group consisting of (a) nucleotide sequences recited in SEQ ID NO: 1–109, 111 and 113, (b) the complements of said nucleotide sequences, and (c) variants of such sequences. As used herein, the term "polypeptide" encompasses amino acid chains of any length, including full length proteins, wherein the amino acid residues are linked by covalent peptide bonds. Thus, a polypeptide comprising a portion of one of the above lung tumor proteins may consist entirely of the portion, or the portion may be present within a larger polypeptide that contains additional sequences. The additional sequences may be derived from the native protein or may be heterologous, and such sequences may (but need not) be immunoreactive and/or antigenic. As detailed below, such polypeptides may be isolated from lung tumor tissue or prepared by synthetic or recombinant means.

As used herein, an "immunogenic portion" of a lung tumor protein is a portion that is capable of eliciting an immune response in a patient inflicted with lung cancer and as such binds to antibodies present within sera from a lung cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies: A Laboratory Manual,* Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of lung cancer patients. Methods for preparing and identifying immunogenic portions of antigens of known sequence are well known in the art and include those summarized in Paul, *Fundamental Immunology,* $3^{rd}$ ed., Raven Press, 1993, pp. 243–247.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. The identity of polypeptides may be determined by comparing sequences using computer algorithms well known to those of skill in the art, such as Megalign, using default parameters.

For lung tumor polypeptides with immunoreactive properties, variants may, alternatively, be identified by modifying the amino acid sequence of one of the above polypeptides, and evaluating the immunoreactivity of the modified polypeptide. For lung tumor polypeptides useful for the generation of diagnostic binding agents, a variant may be identified by evaluating a modified polypeptide for the ability to generate antibodies that detect the presence or absence of lung cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants of the inventive polypeptides may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA,* 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. The identity of nucleotide sequences may be determined by comparing sequences using computer algorithms well known to those of skill in the art, such as Megalign, using default parameters. Such variant nucleotide sequences will generally hybridize to the recite nucleotide sequence under moderately stringent conditions. As used herein, "moderately stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The lung tumor polypeptides of the present invention, and DNA molecules encoding such polypeptides, may be isolated from lung tumor tissue using any of a variety of methods well known in the art. For example, DNA sequences corresponding to a gene (or a portion thereof) encoding one of the inventive lung tumor proteins may be isolated from a lung tumor cDNA library using a subtraction technique as described in detail below. Examples of such DNA sequences are provided in SEQ ID NO: 1–109, 111 and 113. Partial DNA sequences thus obtained may be used to design oligonucleotide primers for the amplification of full-length DNA sequences from a human genomic DNA library or from a lung tumor cDNA library in a polymerase chain reaction (PCR), using techniques well known in the art (see, for example, Mullis et al., *Cold Spring Harbor Symp. Quant. Biol.* 51:263, 1987; Erlich ed., *PCR Technology,* Stockton Press, NY, 1989). For this approach, sequence-specific primers may be designed based on the nucleotide sequences provided herein and may be purchased or synthesized.

Once a DNA sequence encoding a polypeptide is obtained, the polypeptide may be produced recombinantly by inserting the DNA sequence into an expression vector and expressing the polypeptide in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes the recombinant polypeptide. Suitable host cells include prokaryotes, yeast, insect and higher eukaryotic cells. Preferably, the host cells employed are *E. coli,* yeast or a mammalian cell line, such as COS or CHO cells. The DNA sequences expressed in this manner may encode naturally occurring polypeptides, portions of naturally occurring polypeptides, or other variants thereof. Supernatants from suitable host/vector systems which secrete the recombinant polypeptide may first be concentrated using a commercially available filter. The concentrate may then be applied to a suitable purification matrix, such as an affinity matrix or ion exchange resin. Finally, one or more reverse phase HPLC steps can be employed to further purify the recombinant polypeptide.

The lung tumor polypeptides disclosed herein may also be generated by synthetic means. In particular, synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known lung tumor antigen, together with variants of such fusion proteins. The fusion proteins of the present invention may (but need not) include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985, Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91 (1997)).

Polypeptides of the present invention that comprise an immunogenic portion of a lung tumor protein may generally be used for therapy of lung cancer, wherein the polypeptide stimulates the patient's own immune response to lung tumor cells. The present invention thus provides methods for using one or more of the compounds described herein (which may be polypeptides, DNA molecules or fusion proteins) for immunotherapy of lung cancer in a patient. As used herein, a "patient" refers to any warm-blooded animal, preferably a human. A patient may be afflicted with disease, or may be free of detectable disease. Accordingly, the compounds disclosed herein may be used to treat lung cancer or to inhibit the development of lung cancer. The compounds may be administered either prior to or following surgical removal of primary tumors and/or treatment by administration of radiotherapy and conventional chemotherapeutic drugs.

In these aspects, the inventive polypeptide is generally present within a pharmaceutical composition or a vaccine. Pharmaceutical compositions may comprise one or more polypeptides, each of which may contain one or more of the above sequences (or variants thereof), and a physiologically acceptable carrier. The vaccines may comprise one or more such polypeptides and a non-specific immune-response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of lung tumor antigens, either incorporated into a fusion protein as described above (i.e., a single polypeptide that contains multiple epitopes) or present within a separate polypeptide.

Alternatively, a pharmaceutical composition or vaccine may contain DNA encoding one or more of the above polypeptides and/or fusion proteins, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a lung cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science* 259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against lung tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of immune-response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of lung cancer. For example, cells of the immune system, such as T cells, may be isolated from the peripheral blood of a patient, using a commercially available cell separation system, such as CellPro Incorporated's (Bothell, WA) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides and fusion proteins of the present invention may also, or alternatively, be used to generate binding agents, such as antibodies or fragments thereof, that are capable of detecting metastatic human lung tumors. Binding agents of the present invention may generally be prepared using methods known to those of ordinary skill in the art, including the representative procedures described herein. Binding agents are capable of differentiating between patients with and without lung cancer, using the representative assays described herein. In other words, antibodies or other binding agents raised against a lung tumor protein, or a suitable portion thereof, will generate a signal indicating the presence of primary or metastatic lung cancer in at least about 20% of patients afflicted with the disease, and will generate a negative signal indicating the absence of the disease in at least about 90% of individuals without primary or metastatic lung cancer. Suitable portions of such lung tumor proteins are portions that are able to generate a binding agent that indicates the presence of primary or metastatic lung cancer in substantially all (i.e., at least about 80%, and preferably at least about 90%) of the patients for which lung cancer would be indicated using the full length protein, and that indicate the absence of lung cancer in substantially all of those samples that would be negative when tested with full length protein. The representative assays described below, such as the two-antibody sandwich assay, may generally be employed for evaluating the ability of a binding agent to detect metastatic human lung tumors.

The ability of a polypeptide prepared as described herein to generate antibodies capable of detecting primary or metastatic human lung tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic lung cancer for the presence of a polypeptide that binds to the generated antibodies. Such test assays may be performed, for example, using a representative procedure described below. Polypeptides that generate antibodies capable of detecting at least 20% of primary or metastatic lung tumors by such procedures are considered to be useful in assays for detecting primary or metastatic human lung tumors. Polypeptide specific antibodies may be used alone or in combination to improve sensitivity.

Polypeptides capable of detecting primary or metastatic human lung tumors may be used as markers for diagnosing lung cancer or for monitoring disease progression in patients. In one embodiment, lung cancer in a patient may be diagnosed by evaluating a biological sample obtained from the patient for the level of one or more of the above polypeptides, relative to a predetermined cut-off value. As used herein, suitable "biological samples" include blood, sera, urine and/or lung secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g, Harlow and Lane, *Antibodies: A Laboratory Manual,* Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of lung cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without lung cancer. In general, a sample generating a signal that is three standard deviations above the predetermined cut-off value is considered positive for lung cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for lung cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of lung cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of lung cancer. In this embodiment, assays as described above for the diagnosis of lung cancer may be performed over time, and the change in the level of reactive polypeptide(s) evaluated. For example, the assays may be performed every 24–72 hours for a period of 6 months to 1 year, and thereafter performed as needed. In general, lung cancer is progressing in those patients in whom the level of polypeptide detected by the binding agent increases over time. In contrast, lung cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual,* Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate lung tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify lung tumor-specific cDNA derived from a biological sample, wherein at least one of the oligonucleotide primers is specific for a DNA molecule encoding a lung tumor protein of the present invention. The presence of the amplified cDNA is then detected using techniques well known in the art, such as gel electrophoresis. Similarly, oligonucleotide probes specific for a DNA molecule encoding a lung tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 60%, preferably at least about 75% and more preferably at least about 90%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule comprising sequence selected from SEQ ID NO: 1–109, 111 and 113. Preferably, oligonucleotide probes for use in the inventive diagnostic methods comprise at least about 15 contiguous oligonucleotides of a DNA molecule comprising a sequence provided in SEQ ID NO: 1–109, 111 and 113. Techniques for both PCR based assays and hybridization assays are well known in the art (see, for example, Mullis et al. Ihid; Ehrlich, Ibid). Primers or probes may thus be used to detect lung tumor-specific sequences in biological samples, including blood, semen, lung tissue and/or lung tumor tissue.

The following Examples are offered by way of illustration and not by way of limitation.

EXAMPLES

Example 1

Isolation and Characterization of cDNA Sequences Encoding Lung Tumor Polypeptides This example illustrates the isolation of cDNA molecules encoding lung tumor-specific polypeptides from lung tumor cDNA libraries.

A. Isolation of cDNA Sequences from a Lung Squamous Cell Carcinoma Library

A human lung squamous cell carcinoma cDNA expression library was constructed from poly A+RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly A$^+$ RNA was then purified using an oligo dT cellulose column as described in Sambrook et al., *Molecular Cloning: A Laboratory Manual,* Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies, with 100% of clones having an insert and the average insert size being 2100 base pairs. The normal lung cDNA library contained $1.4 \times 10^6$ independent colonies, with 90% of clones having inserts and the average insert size being 1800 base pairs. For both libraries, sequence analysis showed that the majority of clones had a full length cDNA sequence and were synthesized from mRNA.

cDNA library subtraction was performed using the above lung squamous cell carcinoma and normal lung cDNA libraries, as described by Hara et al. (*Blood,* 84:189–199, 1994) with some modifications. Specifically, a lung squamous cell carcinoma-specific subtracted cDNA library was generated as follows. Normal tissue cDNA library (80 µg) was digested with BamHI and XhoI, followed by a filling-in reaction with DNA polymerase Klenow fragment. After phenol-chloroform extraction and ethanol precipitation, the DNA was dissolved in 133 µl of $H_2O$, heat-denatured and mixed with 133 µl (133 µg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 µl) was added and the biotinylation reaction was repeated. After extraction with butanol five times, the DNA was ethanol-precipitated and dissolved in 23 µl $H_2O$ to form the driver DNA.

To form the tracer DNA, 10 µg lung squamous cell carcinoma cDNA library was digested with NotI and SpeI, phenol chloroform extracted and passed through Chroma spin-400 columns (Clontech). Typically, 5 µg of cDNA was recovered after the sizing column. Following ethanol precipitation, the tracer DNA was dissolved in 5 µl $H_2O$. Tracer DNA was mixed with 15 µl driver DNA and 20 µl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 µl $H_2O$, mixed with 8 µl driver DNA and 20 µl of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK$^+$ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained $1.76 \times 10^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

B. Isolation of cDNA Sequences from a Lung Adenocarcinoma Library

A human lung adenocarcinoma cDNA expression library was constructed as described above. The library contained $3.2 \times 10^6$ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

Example 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 µg of total RNA with SuperScript II reverse transcriptase (BRL Life Technologies) at 42° C. for one hour. The cDNA was then amplified by PCR with gene-specific primers. To ensure the semi-quantitative nature of the RT-PCR, µ-actin was used as an internal control for each of the tissues examined. 1 µl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-I2-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lung squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99; that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Due to polymorphisms, the clone L531S appears to have two forms. A first determined full-length cDNA sequence for L531S is provided in SEQ ID NO: 109, with the corresponding predicted amino acid sequence being provided in SEQ ID NO: 110. A second determined full-length cDNA sequence for L531S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion.

Comparison of the sequences of L514S and L53 IS (SEQ ID NO: 87 and 88, 89 and 90, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114.

Example 4

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polypeptide comprising SEQ ID NO: 112.
2. A pharmaceutical composition capable of eliciting an immune response comprising the polypeptide of claim 1 and a physiologically acceptable carrier.
3. A composition comprising the polypeptide of claim 1 and a non-specific immune response enhancer.
4. The composition of claim 3 wherein the non-specific immune response enhancer is an adjuvant.
5. A fusion protein comprising a polypeptide according to claim 1.
6. A fusion protein comprising a polypeptide according to claim 1 and a known lung tumor antigen.
7. A pharmaceutical composition capable of eliciting an immune response comprising a fusion protein according to any one of claims 5–6 and a physiologically acceptable carrier.
8. A composition comprising a fusion protein according to any one of claims 5–6 and a non-specific immune response enhancer.
9. The composition of claim 8 wherein the non-specific immune response enhancer is an adjuvant.

* * * * *